United States Patent
Bitenc et al.

(10) Patent No.: US 11,530,453 B2
(45) Date of Patent: Dec. 20, 2022

(54) SYSTEMS AND METHODS FOR DETECTION OF MULTIPLE CANCER TYPES

(71) Applicant: Universal Diagnostics, S.L., Seville (ES)

(72) Inventors: Marko Bitenc, Ljubljana (SI); Kristi Kruusmaa, Ljubljana (SI); Juan Martinez-Barea, Seville (ES); Christian Hense, Seville (ES); Pol Sola de los Santos, Seville (ES); Pol Canal Noguer, Seville (ES); Marko Chersicola, Ljubljana (SI); Primož Knap, Ljubljana (SI)

(73) Assignee: Universal Diagnostics, S.L., Seville (ES)

( * ) Notice: Subject to any disclaimer, the term of this patent is extended or adjusted under 35 U.S.C. 154(b) by 0 days.

(21) Appl. No.: 17/027,194

(22) Filed: Sep. 21, 2020

(65) Prior Publication Data

US 2021/0404011 A1 Dec. 30, 2021

Related U.S. Application Data

(60) Provisional application No. 63/046,578, filed on Jun. 30, 2020.

(51) Int. Cl.
*C12Q 1/68* (2018.01)
*C12Q 1/6886* (2018.01)
*C12Q 1/686* (2018.01)

(52) U.S. Cl.
CPC .......... *C12Q 1/6886* (2013.01); *C12Q 1/686* (2013.01); *C12Q 2535/122* (2013.01); *C12Q 2600/154* (2013.01)

(58) Field of Classification Search
CPC ....................................................... C12Q 1/68
(Continued)

(56) References Cited

U.S. PATENT DOCUMENTS 6,265,171 B1 7/2001 Herman et al.
6,605,432 B1 8/2003 Huang
(Continued)

FOREIGN PATENT DOCUMENTS

EP 2481813 A1 8/2012
EP 2497834 A2 9/2012
(Continued)

OTHER PUBLICATIONS

Perakis et al, Advances in Circulating Tumor DNA Analysis, Adv Clin Chem. 2017;80:73-153. doi: 10.1016/bs.acc.2016.11.005. Epub Jan. 3, 2017.*
(Continued)

*Primary Examiner* — Aaron A Priest
(74) *Attorney, Agent, or Firm* — Choate, Hall & Stewart LLP; William R. Haulbrook; Samuel R. Polio

(57) ABSTRACT

The present disclosure provides, among other things, methods for colorectal cancer, breast cancer, lung cancer and/or pancreatic cancer detection (e.g., screening) and compositions related thereto. In various embodiments, the present disclosure provides methods for screening that include analysis of methylation status of one or more methylation biomarkers, and compositions related thereto. In various embodiments, the present disclosure provides methods for detection (e.g., screening) that include detecting (e.g., screening) methylation status of one or more methylation biomarkers in cfDNA, e.g., in ctDNA. In various embodiments, the present disclosure provides methods for screening that include detecting (e.g., screening) methylation status of one or more methylation biomarkers in cfDNA, e.g., in ctDNA, using MSRE-qPCR and/or using massively parallel sequencing (e.g., next-generation sequencing).

11 Claims, 10 Drawing Sheets

Specification includes a Sequence Listing.

US 11,530,453 B2

Page 2

(58) Field of Classification Search
USPC .......................................................... 435/6
See application file for complete search history.

(56) References Cited

U.S. PATENT DOCUMENTS

| | | |
|---|---|---|
| 6,812,339 B1 | 11/2004 | Venter et al. |
| 7,144,701 B2 | 12/2006 | Huang |
| 7,745,391 B2 | 6/2010 | Mintz et al. |
| 7,807,358 B1 | 10/2010 | Huang |
| 8,048,634 B2 | 11/2011 | Lai |
| 9,745,622 B2 | 8/2017 | An et al. |
| 9,850,523 B1 * | 12/2017 | Chudova ............... C12Q 1/6827 |
| 10,006,925 B2 | 6/2018 | Bitenc et al. |
| 10,301,680 B2 | 5/2019 | Ahlquist et al. |
| 10,392,666 B2 | 8/2019 | Lo et al. |
| 10,428,388 B2 | 10/2019 | An et al. |
| 11,001,898 B2 | 5/2021 | Bitenc et al. |
| 11,118,228 B2 | 9/2021 | Allawi et al. |
| 11,345,967 B2 | 5/2022 | Morris |
| 11,396,679 B2 | 7/2022 | Bitenc et al. |
| 2007/0237813 A1 * | 10/2007 | Misawa ................... A61P 35/00 536/24.1 |
| 2007/0298506 A1 | 12/2007 | Ordway et al. |
| 2010/0167940 A1 | 7/2010 | Feinberg |
| 2010/0240549 A1 | 9/2010 | Brown |
| 2010/0298158 A1 | 11/2010 | DePinho et al. |
| 2011/0318738 A1 | 12/2011 | Jones et al. |
| 2012/0289581 A1 | 11/2012 | Chang et al. |
| 2013/0012410 A1 | 1/2013 | Zou et al. |
| 2013/0085681 A1 * | 4/2013 | Deciu ..................... G16B 20/10 702/19 |
| 2013/0189684 A1 * | 7/2013 | Ehrich ................. C12Q 1/6886 435/6.11 |
| 2013/0288247 A1 | 10/2013 | Mori et al. |
| 2014/0128283 A1 | 5/2014 | Feinberg et al. |
| 2015/0011403 A1 | 1/2015 | Lo et al. |
| 2015/0072866 A1 | 3/2015 | Weisburg et al. |
| 2015/0152505 A1 | 6/2015 | Lapointe et al. |
| 2016/0333416 A1 | 11/2016 | Babiarz et al. |
| 2016/0355885 A1 * | 12/2016 | Weinhäusel ......... C12Q 1/6886 |
| 2017/0016048 A1 * | 1/2017 | Blauwkamp ......... C12Q 1/6806 |
| 2017/0101674 A1 * | 4/2017 | So ......................... C12Q 1/6874 |
| 2017/0335401 A1 | 11/2017 | Allawi et al. |
| 2017/0356051 A1 * | 12/2017 | Ishioka ................ C12Q 1/6886 |
| 2017/0369948 A1 | 12/2017 | Markowitz et al. |
| 2018/0051338 A1 * | 2/2018 | West ....................... G16B 20/10 |
| 2018/0119137 A1 | 5/2018 | Matsuguchi et al. |
| 2018/0148777 A1 | 5/2018 | Kirkizlar et al. |
| 2018/0245157 A1 | 8/2018 | Allawi et al. |
| 2018/0251859 A1 | 9/2018 | Ahlguist et al. |
| 2018/0258498 A1 | 9/2018 | Ahlquist et al. |
| 2018/0305765 A1 * | 10/2018 | Feber ..................... C12Q 1/686 |
| 2018/0363063 A1 * | 12/2018 | Guerrero-Preston .. A61B 34/10 |
| 2019/0025308 A1 * | 1/2019 | Cummings ............ G16H 50/20 |
| 2019/0032149 A1 | 1/2019 | Van Engeland et al. |
| 2019/0085406 A1 * | 3/2019 | Mortimer ............... G16H 50/30 |
| 2019/0112645 A1 * | 4/2019 | Woodhouse ......... C12Q 1/6883 |
| 2019/0161805 A1 * | 5/2019 | Ahlquist ................ G16H 50/20 |
| 2019/0256921 A1 | 8/2019 | Mueller et al. |
| 2019/0256924 A1 * | 8/2019 | Vogelstein ............. C12Q 1/686 |
| 2019/0352721 A1 | 11/2019 | Kusunoki et al. |
| 2020/0017916 A1 | 1/2020 | Ren |
| 2020/0157640 A1 | 5/2020 | Letourneur et al. |
| 2020/0340062 A1 | 10/2020 | Salhia |
| 2020/0377954 A1 | 12/2020 | Bitenc et al. |
| 2020/0377959 A1 | 12/2020 | Bitenc et al. |
| 2021/0139948 A1 | 5/2021 | Bitenc et al. |
| 2021/0230707 A1 | 7/2021 | Bitenc et al. |
| 2021/0277487 A1 | 9/2021 | Bitenc et al. |
| 2021/0324477 A1 | 10/2021 | Xiang et al. |
| 2021/0332440 A1 | 10/2021 | Kruusmaa et al. |
| 2021/0355542 A1 | 11/2021 | Bitenc et al. |
| 2021/0404010 A1 | 12/2021 | Bitenc et al. |
| 2022/0106644 A1 | 4/2022 | Taylor et al. |
| 2022/0136058 A1 | 5/2022 | Allawi et al. |
| 2022/0186323 A1 | 6/2022 | Mortimer et al. |
| 2022/0228221 A1 | 7/2022 | Curtis |

FOREIGN PATENT DOCUMENTS

| | | | |
|---|---|---|---|
| EP | 2886659 A1 | 6/2015 | |
| EP | 2899275 A1 | 7/2015 | |
| EP | 2977467 A2 | 1/2016 | |
| WO | WO-02/081749 A2 | 10/2002 | |
| WO | WO-2005/001142 A2 | 1/2005 | |
| WO | WO-2007/149269 A2 | 12/2007 | |
| WO | WO-2010/118559 A1 | 10/2010 | |
| WO | WO-2012/034170 A1 | 3/2012 | |
| WO | WO-2012/047899 A2 | 4/2012 | |
| WO | WO-2012/104642 A1 | 8/2012 | |
| WO | WO-2012/154979 A2 | 11/2012 | |
| WO | WO-2012/167145 A2 | 12/2012 | |
| WO | WO-2012/170715 A1 | 12/2012 | |
| WO | WO-2013/057581 A2 | 4/2013 | |
| WO | WO-2013/097868 A1 | 7/2013 | |
| WO | WO-2014/032227 A1 | 3/2014 | |
| WO | WO-2014062218 A1 * | 4/2014 | ........... C12Q 1/6886 |
| WO | WO-2015/116837 A1 | 8/2015 | |
| WO | WO-2015/153283 A1 | 10/2015 | |
| WO | WO-2015/153284 A1 | 10/2015 | |
| WO | WO-2015/159292 A2 | 10/2015 | |
| WO | WO-2016060278 A1 * | 4/2016 | ............... A61P 35/00 |
| WO | WO-2016/109782 A2 | 7/2016 | |
| WO | WO-2017/012592 A1 | 1/2017 | |
| WO | WO-2017/043497 A1 | 3/2017 | |
| WO | WO-2017/048932 A1 | 3/2017 | |
| WO | WO-2017/192221 A1 | 11/2017 | |
| WO | WO-2017201606 A1 * | 11/2017 | ........... C12Q 1/6827 |
| WO | WO-2017/212428 A1 | 12/2017 | |
| WO | WO-2018/087129 A1 | 5/2018 | |
| WO | WO-2018/119452 A2 | 6/2018 | |
| WO | WO-2018/140781 A1 | 8/2018 | |
| WO | WO-2018/195211 A1 | 10/2018 | |
| WO | WO-2018/209361 A2 | 11/2018 | |
| WO | WO-2019/068082 A1 | 4/2019 | |
| WO | WO-2019/175876 A2 | 9/2019 | |
| WO | WO-2020/069350 A1 | 4/2020 | |
| WO | WO-2020/232109 A1 | 11/2020 | |
| WO | WO-2020/239895 A2 | 12/2020 | |
| WO | WO-2020/239896 A1 | 12/2020 | |
| WO | WO-2021/016441 A1 | 1/2021 | |
| WO | WO-2021/041726 A1 | 3/2021 | |
| WO | WO-2021/216477 A1 | 10/2021 | |
| WO | WO-2022/002424 | 1/2022 | |
| WO | WO-2022/003572 A1 | 1/2022 | |

OTHER PUBLICATIONS

Kirkizlar et al., Detection of Clonal and Subclonal Copy-Number Variants in Cell-Free DNA from Patients with Breast Cancer Using a Massively Multiplexed PCR Methodology, Transl Oncol. Oct. 2015;8(5):407-416. doi: 10.1016/j.tranon.2015.08.004.*

Adalsteinsson et al, Scalable whole-exome sequencing of cell-free DNA reveals high concordance with metastatic tumors, Nature Communications vol. 8, Article No. 1324 (2017).*

Heidary et al, The dynamic range of circulating tumor DNA in metastatic breast cancer, The dynamic range of circulating tumor DNA in metastatic breast cancer, Breast Cancer Res. Aug. 9, 2014;16(4):421. doi: 10.1186/s13058-014-0421-y.*

Kukita et al., High-fidelity target sequencing of individual molecules identified using barcode sequences: de novo detection and absolute quantitation of mutations in plasma cell-free DNA from cancer patients, DNA Res. Aug. 2015; 22(4): 269-277, Published online Jun. 29, 2015.*

Lianidou, Detection and relevance of epigenetic markers on ctDNA: recent advances and future outlook, Mol Oncol. Jun. 2021; 15(6): 1683-1700. Published online May 14, 2021. doi: 10.1002/1878-0261.12978.*

Leary et al, Detection of chromosomal alterations in the circulation of cancer patients with whole-genome sequencing, Sci Transl Med.

(56) References Cited

OTHER PUBLICATIONS

Nov. 28, 2012;4(162):162ra154. doi: 10.1126/scitranslmed. 3004742.*
Aberle, D.R., et al., Reduced lung-cancer mortality with low-dose computed tomographic screening, National Lung Screening Trial Research Team, 365(5):395-409, (2011).
Adler, A. et al., Improving compliance to colorectal cancer screening using blood and stool based tests in patients refusing screening colonoscopy in Germany, BMC Gastroenterology, 14:183, (2014).
Andersson, I., et al., Mammographic screening and mortality from breast cancer: the Malmö mammographic screening trial, 297(6654): 943-8, (1988).
Beikircher, G. et al., Multiplexed and Sensitive DNA Methylation Testing Using Methylation-Sensitive Restriction Enzymes "MSRE-qPCR", DNA Methylation Protocols, Methods in Molecular Biology 1708:Ch21:407-424, (2018).
Bray, F. et al., Global Cancer Statistics 2018: GLOBOCAN Estimates of Incidence and Mortality Worldwide for 36 Cancers in 185 Countries, CA Cancer J Clin., 68:394-424, (2018).
Breast Cancer Screening (PDQ®)—Health Professional Version, <https://www.cancer.gov/types/breast/hp/breast-screening-pdq#section/all>. Retrieved on Jul. 17, 2020.
Calderwood, A. H. et al., Colon adenoma features and their impact on risk of future advanced adenomas and colorectal cancer, World Journal of Gastrointestinal Oncology, 8(12):826-834, (2016).
Capman, M. et al., MethyLight and Digital MethyLight, DNA Methylation Protocols, Methods in Molecular Biology, 1708:CH25:497-513, (2018).
Chang, C. P.-Y. et al., Elevated cell-free serum DNA detected in patients with myocardial infarction, Clinica Chimica Acta 327:95-101, (2003).
Chen, Y. et al., Tissue-independent and tissue-specific patterns of DNA methylation alteration in cancer, Epigenetics & Chromatin, 9:10, (2016).
Chiu, R. W. K. et al., Noninvasive prenatal diagnosis of fetal chromosomal aneuploidy by massively parallel genomic sequencing of DNA in maternal plasma, PNAS, 105(51):20458-20463, (2008).
Demissie, K., et al., Empirical comparison of the results of randomized controlled trials and case-control studies in evaluating the effectiveness of screening mammography, 51(2):81-91, (1998).
DOE Joint Genome Institute (AC012313; Mar. 2003), (2003).
DOE Joint Genome Institute (AC024563; Jul. 2002), (2002).
Esteller, M., CpG island hypermethylation and tumor suppressor genes: a booming present, a brighter future, Oncogene, 21:5427-5440, (2002).
Fackler, M. J. and Sukumar, S., Quantitation of DNA Methylation by Quantitative Multiplex Methylation-Specific PCR (QM-MSP) Assay, DNA Methylation Protocols, Methods in Molecular Biology, 1708:CH24:473-496, (2018).
Fan, C.H.. et al., Noninvasive diagnosis of fetal aneuploidy by shotgun sequencing DNA from maternal blood, Proceedings of The National Academy of Sciences, 105(42):16266-16271 (2008).
Frommer, M. et al., A genomic sequencing protocol that yields a positive display of 5-methylcytosine residues in individual DNA strands, Proc. Natl. Acad. Sci. USA, 89:1827-1831, (1992).
Galanopoulos, M., et. al., Abnormal DNA methylation as a cell-free circulating DNA biomarker for colorectal cancer detection: A review of literature, World Journal of Gastrointestinal Oncology, 9(4):142-152, (2017).
Galeazzi, M. et al., Dosage and characterization of circulating DNA: present usage and possible applications in systemic autoimmune disorders, Autoimmunity Reviews, 2:50-55, (2003).
Gasc, C. et al., Survey and Summary: Sequence capture by hybridization to explore modern and ancient genomic diversity in model and nonmodel organisms, Nucleic Acids Research, 44(10):4504-4518, (2016).
Gonzalgo, M. L. and Liang, G., Methylation-sensitive single-nucleotide primer extension (Ms-SNuPE) for quantitative measurement of DNA methylation, Nature Protocols, 2(8):1931-1936, (2007).

Hemmasi, G., et al., Prevalence of colorectal adenoma in an average-risk population aged 40-50 versus 50-60 years, European Journal of Cancer Prevention (ECP), pp. 1-5, (2014).
Herman, J. G. et al., Methylation-specific PCR: A novel PCR assay for methylation status of CpG islands, Proc. Natl. Acad. Sci. USA, 93:9821-9826, (1996).
Hussmann, D. and Hansen, L. L., Methylation-Sensitive High Resolution Melting (MS-HRM), DNA Methylation Protocols, Methods in Molecular Biology, 1708:CH28:551-571, (2018).
Imperiale, T. F. et al., Multitarget Stool DNA Testing for Colorectal-Cancer Screening, Correspondence to the Editor, The New England Journal of Medicine, doi:10.1056/NEJMc1405215, 371(2):184-188, (2014).
Imperiale, T. F. et al., Multitarget Stool DNA Testing for Colorectal-Cancer Screening, The New England Journal of Medicine, 370(14):1287-1297, (2014).
Ivanov, M. et al., In-solution hybrid capture of bisulfite-converted DNA for targeted bisulfite sequencing of 174 ADME genes, Nucleic Acids Research, 46(6):e72, 9 pages, (2013).
Karsenti, D. et al., Adenoma and advanced neoplasia detection rates increase from 45 years of age, World Journal of Gastroenterology, 25(4): 447-456 (2019).
Kok-Sin, T., et. al., Identification of diagnostic markers in colorectal cancer via integrative epigenomics and genomics data, Oncology Reports, 34:22-32, (2015).
Kordowski., F., et al., Aberrant DNA methylation of ADAMTS16 in colorectal and other epithlial cancers, BMC Cancer, 18(1):4, (2018).
Krueger, F. and Andrews, S.R., Bismark: a flexible aligner and methylation caller for Bisulfite-Seq applications, Bioinformatics, 27(11):1571-2, (2011).
Kruusmaa, K et. al., MSRE-qPCR for analysis of gene specific methylation can be accurately used for detection and validation of colorectal cancer-specific patterns, 4Bio Summit (Jan. 1, 2018). <www.universaldx.com/wp-content/uploads/2017/05/4Bio-poster-November-2018.pdf>. Retrieved on Aug. 19, 2020.
Kutsenko, A., et. al., NotI flanking sequences: a tool for gene discovery and verification of the human genome, Nucleic Acids Research, 30(14):3163-3170, (2002).
Laird, P. W., Applications of Next-Generation Sequencing: Principles and challenges of genomewide DNA methylation analysis, Nature Review, Genetics, 11:191-203, (2010).
Leon, S. A. et al., Free DNA in the Serum of Cancer Patients and the Effect of Therapy, Cancer Research, 37:646-650, (1977).
Liles, E. G. et al., Uptake of a colorectal cancer screening blood test is higher than of a fecal test offered in clinic: A randomized trial, Cancer Treatment and Research Communications, 10:27-31, (2017).
Liu, Y. et al., Methylation-sensitive enrichment of minor DNA alleles using a double-strand DNA-specific nuclease, Nucleic Acids Research, 45(6):e39, 11 pages, (2017).
Lowe, T., et. al., A Computer program for selection of oligonucleotide primers for polymerase chain reactions, Nucleic Acids Research. 18(7):1757-1761, (1990).
Masser, D. R. et al., Targeted DNA Methylation Analysis by Next-generation Sequencing, Jounarl of Visualized Experiments, www.jove.com, © Creative Commons Attribution—NonCommercial License, 96:52488, 11 pages, (2015).
Melnikov, A. A., et. al., MSRE-PCR for analysis of gene-specific DNA methylation, Nucleic Acids Research, 33(10): e93-e93, (2015).
Meyer, D. et al., Package 'e1071', Misc Functions of the Department of Statistics, Probability Theory Group (Formerly: E1071), TU Wien, HTTPS://cran.r-project.org/web/packages/e1071/index.html, 63 pages, (2019).
Nakamura, A. et al., Relationship between sodium excretion and pioglitazone-induced edema, Journal of Diabetes Investigation, 1(5):208-211, (2010).
Navarro, M. et al., Colorectal cancer population screening programs worldwide in 2016: An Update, World J Gastroenterol, 23(20):3632-3642, (2017).
O'Connell B., and Crockett S., The clinical impact of serrated colorectal polyps, Dove Press Journal, Clinical Epidemiology, 9: 113-125 (2017).

(56) References Cited

OTHER PUBLICATIONS

Oh, T. et al., Genome-Wide Identification and Validation of a Novel Methylation Biomarker, SDC2, for Blood-Based Detection of Colorectal Cancer, The Journal of Molecular Diagnostics, 15(4):498-507, (2013).

Potter, N. T. et al., Validation of a Real-Time PCR-Based Qualitative Assay for the Detection of Methylated SEPT9 DNA in Human Plasma, Clinical Chemistry, 60(9):1183-1191, (2014).

QIAamp® Circulating Nucleic Acid Handbook, For concentration and purification of free-circulating DNA, RNA, miRNA, and viral nucleic acids from human plasma, serum, urine, or other cell-free body fluids, Oct. 2019.

QIAamp® MinElute® ccfDNA Handbook, For concentration and purification of circulation cell-free DNA from plasma or serum, Jan. 2020.

Rahib, L., et. al., Projecting cancer incidence and deaths to 2030: the unexpected burden of thyroid, liver, and pancreas cancers in the United States, 74(11):2913-21, (2014).

Schwarzenbach, H. et al., Cell-free nucleic acids as biomarkers in cancer patients, Nature Reviews / Cancer, 11:426-437, (2011).

Shaukat, A. et al., Long-Term Mortality after Screening for Colorectal Cancer, The New England Journal of Medicine, 369(12):1106-1114, (2013).

Singh, K. E. et al., Colorectal Cancer Incidence Among Young Adults in California, Journal of Adolescent and Young Adult Oncology, 3(4):176-184, (2014).

Snyder, M.W. et al., Cell-free DNA Comprises an In vivo Nucleosome footprint that informs its Tissues-Of-Origin, Cell, 164: pp. 57-68, (2016).

Swarup, V. and Rajeswari, M.R., Circulating (cell-free) nucleic acids—A promising, non-invasive tool for early detection of several human diseases, FEBS Letters 581:795-799, (2007).

The Cancer Genome Atlas Program, <https://www.cancer.gov/about-nci/organization/ccg/research/structural-genomics/tcga>. Retrieved on Jul. 17, 2020.

Vainio, H., et al., IARC Handbooks of Cancer Prevention Programme Head: Harri Vainio. vol. 7: Breast Cancer Screening, pp. 1-236, (2002).

Van Der Vlugt, M. et al., Adherence to colorectal cancer screening: four rounds of faecal immunochemical test-based screening, British Journal of Cancer, 116(1):44-49, (2017).

Wittenberger, T. et al., DNA methylation markers for early detection of women's cancer: promise and challenges, Epigenomics, 6(3):311-327, (2014).

Yan, H., et. al., Identifying CpG sites with different differential methylation frequencies in colorectal cancer tissues based on individualized differential methylation analysis, Open Access Impact Journal, 29(8): 47356-47364, (2017).

Yang, Y., et. al., Indentification of regulatory role of DNA methylation in colon cancer gene expression via sytematic bioinformatics analysis, Medicine, 96(47):1-7, (2017).

Adusumalli, S. et al., Methodological aspects of whole-genome bisulfite sequencing analysis, Briefings in Bioinformatics, 16(3):369-379, (2014).

Blesa, J. R. et al., NRF-1 is the major transcription factor regulating the expression of the human TOMM34 gene, Biochemistry and Cell Biology, Biochem Cell Biol., 86(1):46-56, (2008).

International Search Report for PCT/EP2020/076226, 5 pages (dated Mar. 24, 2021).

Liu, W-B et al., TMEM196 acts as a novel functional tumour suppressor inactivated by DNA methylation and is a potential prognostic biomarker in lung cancer, Oncotarget, 6(25):21225-21239, (2015).

Margolin, G. et al., Robust Detection of DNA Hypermethylation of ZNF154 as a Pan-Cancer Locus with in Silico Modeling for Blood-Based Diagnostic Development, The Journal of Molecular Diagnostics, 18(2):283-298, (2016).

Mitchell, S. M. et al., A panel of genes methylated with high frequency in colorectal cancer, BMC Cancer, Biomed Central, London, GB, 14(1):54, 15 pages, (2014).

Written Opinion for PCT/EP2020/076226, 5 pages (dated Mar. 24, 2021).

Zhou, X. et al., Identification of epigenetic modulators in human breast cancer by integrated analysis of DNA methylation and RNA-Seq data, Epigenetics, 13(5):473-489, (2018).

Chen, J. et. al., DNA methylation biomakers in stool for early screening of colorectal cancer, Journal of Cancer, 10(21):5264-5271, (2019).

Chen, J.J., et. al., DNA methylation assay for colorectal carcinoma, Cancer Biology & Medicine, 14(1):42-49, (2017).

Lam, K. et al., DNA methylation based biomakers in colorectal cancer: A systematic review, Elsevier Science BV, Biochimica et Biophysica Acta 1866:106-1202 (2016).

Li, H. et. al., Identification of novel DNA methylation markers in colorectal cancer using MIRA-based microarrays, Oncology Reports, National Hellenic Research Foundation, 28(1):99-104, (2012).

Mitchell, S.M. et. al., A panel of genes methylated with high frequency in colorectal cancer, BMC cancer, Biomed Central, 14(1):54, (2014).

Bacolod, M. D. et al., Application of Multiplex Bisulfite PCR-eLigase Detection Reactione-Real-Time Quantitative PCR Assay in Interrogating Bioinformatically Identified, Blood-Based Methylation Markers for Colorectal Cancer, The Journal of Molecular Diagnostics, 22(7):886-900, (2020).

Genecards, ALKAL1 Gene—ALK and LTK Ligand 1, 18 pages, (2022).

Michels, K.B., The promises and challenges of epigenetic epidemiology, Exp. Gerontol., 45(4):297-301, (2010).

Petko, Z. et al., Aberrantly methylated CDKN2A, MGMT, and MLH1 in colon polyps and in fecal DNA from patients with colorectal polyps, Clin. Cancer Res., 11(3):1203-1209 (2005).

UCSC Genome Browser 1, CpG Island Info, Band 9p21.3, 2 pages, (2020).

UCSC Genome Browser 2, CpG Island Info, Band 8q11.23, 2 pages, (2020).

Zhang, S. et al., CRISPR/Cas9-mediated knockout of NSD1 suppresses the hepatocellular carcinoma development via the NSD1/H3/Wnt10b signaling pathway, Journal of Experimental and Clinical Cancer Research, 38(1):467, (2019).

Exner, R. et al., Potential of DNA methylation in rectal cancer as diagnostic and prognostic biomarkers, Br. J. Cancer, 113(7):1035-1045 (2015).

Pulverer, W. et al., The stem cell signature of CHH/CHG methylation is not present in 271 cancer associated 5'UTR gene regions, Biochimie, 94(11):2345-2352 (2012).

\* cited by examiner

SEQUENCE LISTING

<160> NUMBER OF SEQ ID NOS: 122

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tcgaacccat taattgggcc ata                                          23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccaaggagag aaccctgcca tcg                                          23

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttgtgcgcgt gcaaaggttc                                              20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagagcgccg gcaagagc                                                18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttagcgcagc gcagctggag                                              20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcccaagcct caccctcaca cag                                          23

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agagtagcca actttgggggg ttgct                                     25

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caggctgggc ggtctttgac                                            20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caagacctgg cgcatctttg c                                          21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tccgggctca agttgcaagg                                            20

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgaaagaaa tccgagccag ggtga                                      25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctctcagtcc cgccggctta ggta                                       24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgtgcgaag tctcctctag cgga                                       24

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtaaggggc agagcgaggg gt                                          22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cggcgcagcc tttctggttt                                             20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcctggggca ctctgttgca ct                                          22

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcgggaaggg agtacaactg acc                                         23

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccccactgcc gcatccttac                                             20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cccagtcctg gggcagctac a                                           21

```
<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgaaccatcc ctccgcgcca                                               20

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggcactgtac cgagcttgct gttct                                         25

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggggtagcgg gtgcttccag                                               20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ttgcaggctg gattaggatg c                                             21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcgaggcatc tgggcttcag                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggttttgttg ccccacgtcc                                               20
```

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
gcaagagacg cggacctgga gc				22

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ctcaggtttc caggcgcggc t				21

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ctcagatggg agcgcggcag gaa				23

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
ccccctccat gcagcaagc				19

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gcaggtagct tcacctggga gtcg				24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ggggtttgta aaccgaggcc agag				24

<210> SEQ ID NO 32

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gccggcagct gcttggtagt tg                                                  22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcaccgcggg ctacgccact                                                     20

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccatggcttc ctttctttgg caga                                                24

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggcaaattga ggccgagctg                                                     20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tccccaaagc gcagagacag a                                                   21

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cccggggatg ttttggtcgt                                                     20

<210> SEQ ID NO 38
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtaggaggcg cagggcaggt                                             20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggtggatcga aagcgccaaa                                             20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agcggctgaa attggtgcgc c                                           21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agatccggtg cgggtgacag                                             20

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gagctgaggt ctacgcggtc cc                                          22

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggctatgact tcgctgttgt cacc                                        24

<210> SEQ ID NO 44
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 44
gtctccagac tcgctgggaa ccac                                              24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
catctgtagg gtgcagggct gtcc                                              24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgtgttctgg ccggaagttg agtg                                              24

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tccgggaaac atagtcttta ggcgt                                             25

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccccacgcgt actcacaccg aag                                               23

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtcgcgcgtt tccctcccag                                                   20

<210> SEQ ID NO 50
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 50
ctgctcttac ccgccggaac cctg                                              24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tctgactggc attgaggaag gtcg                                              24

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccgcgtggtc tgggctctgt ag                                                22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cttcagagag cagccttccc gg                                                22

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
caacggaaac ttcccgcgct ac                                                22

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcatctatgc gggcatggtt actg                                              24

<210> SEQ ID NO 56
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 56
ctccagcagc gccgagaaac                                              20

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agaggatacc agcggcagac caca                                         24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cgctgcctcc actgtttcct ctca                                         24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gagggttgcc tcgatacttc ctca                                         24

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gctttcccag cccggtgttt                                              20

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ttccctgagg agtctgggga ggag                                         24

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 62
cgagccccac acagcacctt                                                 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cgtccctcag ccctcagcaa                                                 20

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cctttgcgtc cggctacgg                                                  19

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cctcgaccgt tccgggctta                                                 20

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tggcagtgta gctgcgagaa cc                                              22

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ctatgcagga acccgccgac cg                                              22

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 68
caagccacca cgcgggatta                                            20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ccagcgcggt ccacccattg                                            20

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggaactgacg gagccgaagg a                                          21

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cccctcccca aactctccta ttcca                                      25

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tatgcctcgg cgtggctaga gagg                                       24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cgaatgttca tcccgcgcgc agtt                                       24

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 74
gaacagcact cctccgcgca ctg                                               23

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gcgggtaaga gcaggagtgt g                                                 21

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gagggacctt agagcagagc gggc                                              24

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ttggggtcct ggtccttggc gc                                                22

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gaattccctc cacctccgcc ccac                                              24

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gaacgcggcg ccctctcact t                                                 21

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

```
ctcgccgggg gcttcgctac                                              20
```

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

```
cgtggacctg gctgaggagc tg                                           22
```

<210> SEQ ID NO 82
<211> LENGTH: 105
<212> TYPE: DNA
<213> ORGANISM: Homo sapiens

<400> SEQUENCE: 82

```
ccccctccat gcagcaagcg attctccgcg tccgaggcca gtttcctgga gggagaggcc   60
agtccccctt tgggcgcccg ccgccgtttc tcggcgctgc tggag                  105
```

<210> SEQ ID NO 83
<211> LENGTH: 93
<212> TYPE: DNA
<213> ORGANISM: Homo sapiens

<400> SEQUENCE: 83

```
gcaggtagct tcacctggga gtcgccgata ggaaggaggg aggggaccca gacgtgcctc   60
tgccctgcct gtggtctgcc gctggtatcc tct                               93
```

<210> SEQ ID NO 84
<211> LENGTH: 106
<212> TYPE: DNA
<213> ORGANISM: Homo sapiens

<400> SEQUENCE: 84

```
ggggtttgta aaccgaggcc agagtgtccc cgtgggccga gcgcactttt ttcttgtccg   60
ggtgcgctca gtcactggtg cctgagagga aacagtggag gcagcg                 106
```

<210> SEQ ID NO 85
<211> LENGTH: 129
<212> TYPE: DNA
<213> ORGANISM: Homo sapiens

<400> SEQUENCE: 85

```
gccggcagct gcttggtagt tgcgggggc gtgagggcgg tggcccagac caaccggctg    60
gcagcccagc tccgctccgc ccgcccctgc ctcggaccct gcgcctgagg aagtatcgag  120
gcaaccctc                                                          129
```

<210> SEQ ID NO 86
<211> LENGTH: 112
<212> TYPE: DNA
<213> ORGANISM: Homo sapiens

<400> SEQUENCE: 86

```
tcaccgcggg ctacgccact cccacccggc acacgcgaca cccgccgcgc gcaggctcct   60
gcttgcaggt ccggccgctg ctcgggccaa gtaaacaccg ggctgggaaa gc          112
```

```
<210> SEQ ID NO 87
<211> LENGTH: 110
<212> TYPE: DNA
<213> ORGANISM: Homo sapiens

<400> SEQUENCE: 87
ccatggcttc ctttctttgg cagagtcagg ctccagaagt ccgccttcct ccacaggcac      60
cctaatctgc cgtgcccttg cagcttctcc tccccagact cctcagggaa                110

<210> SEQ ID NO 88
<211> LENGTH: 107
<212> TYPE: DNA
<213> ORGANISM: Homo sapiens

<400> SEQUENCE: 88
ggcaaattga ggccgagctg acgagctccg gcgggtggac ctgacgtcac cgcggcccgg      60
gtcacctcac ccatggggct ccccaagaag gtgctgtgtg gggctcg                  107

<210> SEQ ID NO 89
<211> LENGTH: 118
<212> TYPE: DNA
<213> ORGANISM: Homo sapiens

<400> SEQUENCE: 89
ccccaaagcg cagagacaga caggatctgc caggacagcg cgcagggcgg ggcggggaca      60
ggcgcgccag gagcggggcg ggcttccagc cgctggtttt gctgagggct gagggacg      118

<210> SEQ ID NO 90
<211> LENGTH: 112
<212> TYPE: DNA
<213> ORGANISM: Homo sapiens

<400> SEQUENCE: 90
tcgaacccat taattgggcc ataaaaagtt ttatgagcct catttacata caatgctatg      60
ggctccacgc aatggcgcct ccgctccaat taaaaccaga aaggctgcgc cg            112

<210> SEQ ID NO 91
<211> LENGTH: 80
<212> TYPE: DNA
<213> ORGANISM: Homo sapiens

<400> SEQUENCE: 91
cccggggatg ttttggtcgt aggaggcgca gggcaggttg ccgtaggcgt cggcgcccag      60
gccgtagccg gacgcaaagg                                                  80

<210> SEQ ID NO 92
<211> LENGTH: 113
<212> TYPE: DNA
<213> ORGANISM: Homo sapiens

<400> SEQUENCE: 92
gtaggaggcg cagggcaggt tgccgtaggc gtcggcgccc aggccgtagc cggacgcaaa      60
ggggctctga taaggggggc tgttgacatt gtataagccc ggaacggtcg agg           113

<210> SEQ ID NO 93
<211> LENGTH: 90
<212> TYPE: DNA
<213> ORGANISM: Homo sapiens

<400> SEQUENCE: 93
```

```
ccaaggagag aaccctgcca tcgcgcctgg cccggcccag cccagcccct aggcaacctg    60
cgcccgccag tgcaacagag tgccccaggc                                    90
```

<210> SEQ ID NO 94
<211> LENGTH: 83
<212> TYPE: DNA
<213> ORGANISM: Homo sapiens

<400> SEQUENCE: 94

```
ggtggatcga aagcgccaaa aatcaatcag aaatcgtccc cgtagtttgt gcgcgtgcaa    60
aggttctcgc agctacactg cca                                           83
```

<210> SEQ ID NO 95
<211> LENGTH: 105
<212> TYPE: DNA
<213> ORGANISM: Homo sapiens

<400> SEQUENCE: 95

```
ttgtgcgcgt gcaaaggttc tcgcagctac actgccagaa tagaacgtgc tcctccgctt    60
ttataccccg gaaaaaggc gtggtcagtt gtactccctt cccgc                    105
```

<210> SEQ ID NO 96
<211> LENGTH: 104
<212> TYPE: DNA
<213> ORGANISM: Homo sapiens

<400> SEQUENCE: 96

```
agcggctgaa attggtgcgc cttgtgctgt ggtctgggtg tgtcccggag agggcgcgca    60
ggcgcctatg tctgtcgcgg ggcggtcggc gggttcctgc atag                   104
```

<210> SEQ ID NO 97
<211> LENGTH: 108
<212> TYPE: DNA
<213> ORGANISM: Homo sapiens

<400> SEQUENCE: 97

```
agatccggtg cgggtgacag ccggcgccac ccctgccccc atccctgtga aaagaggcg    60 actgcgcggc gaggggtccc cgtaccccta atcccgcgtg gtggcttg              108
```

<210> SEQ ID NO 98
<211> LENGTH: 92
<212> TYPE: DNA
<213> ORGANISM: Homo sapiens

<400> SEQUENCE: 98

```
gagctgaggt ctacgcggtc ccgctgcgga gcaggcgggg tgaggagctg cggtctgtga    60
gtcctctccc gccaatgggt ggaccgcgct gg                                  92
```

<210> SEQ ID NO 99
<211> LENGTH: 110
<212> TYPE: DNA
<213> ORGANISM: Homo sapiens

<400> SEQUENCE: 99

```
ggctatgact tcgctgttgt caccgagcgc cccgcccacc gcgttctccg acccgcggcc    60
ggcagggggc tcgcggcctc cgccaggcgt ccttcggctc cgtcagttcc             110
```

<210> SEQ ID NO 100
<211> LENGTH: 106

```
<210> SEQ ID NO 100
<211> LENGTH: 106
<212> TYPE: DNA
<213> ORGANISM: Homo sapiens

<400> SEQUENCE: 100
gtctccagac tcgctgggaa ccaccgcaaa gagggtgtgc aagagttgag gccctcacgt    60
cttgggaaag gagagtaggg gtggaatagg agagtttggg gagggg                  106

<210> SEQ ID NO 101
<211> LENGTH: 67
<212> TYPE: DNA
<213> ORGANISM: Homo sapiens

<400> SEQUENCE: 101
catctgtagg gtgcagggct gtcccggagc cttctgcccc cgccctctct agccacgccg    60
aggcata                                                             67

<210> SEQ ID NO 102
<211> LENGTH: 170
<212> TYPE: DNA
<213> ORGANISM: Homo sapiens

<400> SEQUENCE: 102
tgtgttctgg ccggaagttg agtggggccg cggggcctgc tgggaggtgt tgtcctcgga    60
aacgtcgctg gcgcggaggg atggttcggc gctttaggcg tctgtcacag acctatctgc   120
gggtcgcctt cacccagcat ctcagaaact gcgcgcggga tgaacattcg              170

<210> SEQ ID NO 103
<211> LENGTH: 120
<212> TYPE: DNA
<213> ORGANISM: Homo sapiens

<400> SEQUENCE: 103
tccgggaaac atagtcttta ggcgtaaagg cagcagcccg gccttgaagc cggatctcgc    60
gatgtttcag ggtgagccgg acgcaggcgt gcctgcgcag tgcgcggagg agtgctgttc   120

<210> SEQ ID NO 104
<211> LENGTH: 149
<212> TYPE: DNA
<213> ORGANISM: Homo sapiens

<400> SEQUENCE: 104
ccccacgcgt actcacaccg aaggctcagc cgtcgcgcgt ttccctccca ggccccagga    60
actagtaact agggacgctt ctggtctcta ggcgaggaga gggggagagc gcaatctttg   120
cgcctgcgca cactcctgct cttacccgc                                    149

<210> SEQ ID NO 105
<211> LENGTH: 118
<212> TYPE: DNA
<213> ORGANISM: Homo sapiens

<400> SEQUENCE: 105
gtcgcgcgtt tccctcccag gccccaggaa ctagtaacta gggacgcttc tggtctctag    60
gcgaggagag ggggagagcg caatctttgc gcctgcgcac actcctgctc ttacccgc    118

<210> SEQ ID NO 106
<211> LENGTH: 89
<212> TYPE: DNA
<213> ORGANISM: Homo sapiens
```

<400> SEQUENCE: 106
ctgctcttac ccgccggaac cctgggccac gcccggctcg cgtaatcacg cactgcgcag    60
gcaccgcccg ctctgctcta aggtccctc    89

<210> SEQ ID NO 107
<211> LENGTH: 147
<212> TYPE: DNA
<213> ORGANISM: Homo sapiens

<400> SEQUENCE: 107
tctgactggc attgaggaag gtcgcggggc ccgggtagag cgcgaagcag tcgtgctcga    60
cgcactggct gccacccggc tgcggctctg cgggtgcggg aaccccagg ccggccaggg    120 ccagcgcgcc aaggaccagg accccaa    147

<210> SEQ ID NO 108
<211> LENGTH: 80
<212> TYPE: DNA
<213> ORGANISM: Homo sapiens

<400> SEQUENCE: 108
ccgcgtggtc tgggctctgt agcgtcccag ctgagccggc gatatgcagc gcacttgtgg    60
ggcggaggtg gagggaattc    80

<210> SEQ ID NO 109
<211> LENGTH: 78
<212> TYPE: DNA
<213> ORGANISM: Homo sapiens

<400> SEQUENCE: 109
cttcagagag cagccttccc ggagcaccaa ctccgtgtcg ggagtgcaga aaccaacaag    60
tgagagggcg ccgcgttc    78

<210> SEQ ID NO 110
<211> LENGTH: 75
<212> TYPE: DNA
<213> ORGANISM: Homo sapiens

<400> SEQUENCE: 110
caacggaaac ttcccgcgct acggcggctc caacgggccg cttccgccgc attgcgtagc    60
gaagcccccg gcgag    75

<210> SEQ ID NO 111
<211> LENGTH: 99
<212> TYPE: DNA
<213> ORGANISM: Homo sapiens

<400> SEQUENCE: 111
gcatctatgc gggcatggtt actgcctctg gtgcccccg cagccgcgcg caggtaccgt    60
gcgacatcgc gatggcccag ctcctcagcc aggtccacg    99

<210> SEQ ID NO 112
<211> LENGTH: 84
<212> TYPE: DNA
<213> ORGANISM: Homo sapiens

<400> SEQUENCE: 112
cagagcgccg gcaagagctc ggtgctcgag aacttcgtgg gcaggtaagc gcgcagggcg    60
cggagtaagg atgcggcagt gggg    84

<210> SEQ ID NO 113
<211> LENGTH: 76
<212> TYPE: DNA
<213> ORGANISM: Homo sapiens

<400> SEQUENCE: 113
caggctgggc ggtctttgac cccccgcgcc tcccgcccac agccggagcc cggcagctgg    60
aagcacccgc taccccc                                                   76

<210> SEQ ID NO 114
<211> LENGTH: 81
<212> TYPE: DNA
<213> ORGANISM: Homo sapiens

<400> SEQUENCE: 114
caagacctgg cgcatctttg caaattacag ataattgtaa acgtccagat tatgataata    60
gcatcctaat ccagcctgca a                                              81

<210> SEQ ID NO 115
<211> LENGTH: 97
<212> TYPE: DNA
<213> ORGANISM: Homo sapiens

<400> SEQUENCE: 115
ttagcgcagc gcagctggag cagctgcgaa aattcaaggt gggtgcgccc gcgcccccat    60
ccagcgtcca ccaaagtgta gctgcccag gactggg                              97

<210> SEQ ID NO 116
<211> LENGTH: 111
<212> TYPE: DNA
<213> ORGANISM: Homo sapiens

<400> SEQUENCE: 116
tccgggctca agttgcaagg gggcgggccg ggccggaggt ggagtctccc gccaattgaa    60
gcctccgcta taaattgaac tccctgcact gctgaagccc agatgcctcg c             111

<210> SEQ ID NO 117
<211> LENGTH: 104
<212> TYPE: DNA
<213> ORGANISM: Homo sapiens

<400> SEQUENCE: 117
ccgaaagaaa tccgagccag ggtgagggtc tgagacgcaa ggagaatccc aggcaaggcg    60
ctcctgagaa aagatcccca cggcggacgt ggggcaacaa aacc                     104

<210> SEQ ID NO 118
<211> LENGTH: 120
<212> TYPE: DNA
<213> ORGANISM: Homo sapiens

<400> SEQUENCE: 118
gcccaagcct caccctcaca caggaaagca gatgtgttct ggccggaagt tgagtggggc    60
cgcggggcct gctgggaggt gttgtcctcg gaaacgtcgc tggcgcggag ggatggttcg    120

<210> SEQ ID NO 119
<211> LENGTH: 84
<212> TYPE: DNA
<213> ORGANISM: Homo sapiens

```
<400> SEQUENCE: 119
agagtagcca actttggggg ttgctgtgac gtttaaatga gcaagtacat gccagtctta      60
gaacagcaag ctcggtacag tgcc                                            84

<210> SEQ ID NO 120
<211> LENGTH: 77
<212> TYPE: DNA
<213> ORGANISM: Homo sapiens

<400> SEQUENCE: 120
ctctcagtcc cgccggctta ggtaacccag gtcgctgcgg taacgcagtg accgcgctcc      60
aggtccgcgt ctcttgc                                                    77

<210> SEQ ID NO 121
<211> LENGTH: 95
<212> TYPE: DNA
<213> ORGANISM: Homo sapiens

<400> SEQUENCE: 121
gcgtgcgaag tctcctctag cggagcggga ccggccgcgg cggtggatcg tggcggtccc      60
tgcacttctg ctccagccgc gcctggaaac ctgag                                95

<210> SEQ ID NO 122
<211> LENGTH: 87
<212> TYPE: DNA
<213> ORGANISM: Homo sapiens

<400> SEQUENCE: 122
cgtaaggggc agagcgaggg gtccggcatc actcgcgcgc tccggaaacc cgcgtgagcc      60
gctgttcctg ccgcgctccc atctgag                                         87
```

SYSTEMS AND METHODS FOR DETECTION OF MULTIPLE CANCER TYPES

CROSS REFERENCE

This application claims the benefit of and priority to U.S. Provisional App. No. 63/046,578 filed on Jun. 30, 2020, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 17, 2020, is named 2011722-0060_SL.txt and is 28,010 bytes in size.

BACKGROUND

It is estimated that 31.8% of incident cancer diagnoses and 35.3% of cancer-related deaths world-wide in 2018 are related to cancers of colon, pancreas, lung and breast (Bray F et al. C A Cancer J Clin. 2018 November; 68(6):394-424). Lung cancer is leading both in cancer incidence and mortality rates.

Projections for the most common cancer types for the years 2020 and 2030 based on changing demographics and the average annual percentage changes in incidence and death rates show that lung cancer will remain the top cancer diagnose with highest mortality rates (Rahib L et al. Cancer Res. 2014; 74(11):2913-2921). While pancreatic cancer is expected to surpass colorectal cancer and breast cancer in cancer mortality (Rahib L et al. Cancer Res. 2014; 74(11): 2913-2921). It is proposed that the advances in screening, prevention, and treatment can change cancer incidence and/or death rates, but accurate and/or non-invasive screening tools for early detection are missing for all of these cancer cases.

For example, although the screening programs are available for colorectal cancer, and the survival rates have gone up within the last 30 years, only about 40-44% of the cancers are detected in an early, localized stage due to low sensitivity of most of the screening programs. Additionally, the cancer incidence is increasing also among younger adults (Singh K E et al. J Adolesc Young Adult Oncol. 2014 Dec. 1; 3(4): 176-184), indicating the need to explore colorectal cancer screening beyond current recommendations.

The current practice for detecting lung cancer is based on a symptomatic diagnosis, where person with symptoms is referred to a specialist. Typically, bronchoscopy or computed tomography (CT) scan is performed for determination along with other imaging techniques, biopsy and/or surgery for final diagnosis. CT identifies millions of pulmonary nodules annually, with many undiagnosed as either malignant or benign. However, despite the 20% relative reduction in lung cancer related mortality shown by low dosage CT (LDCT) screening in the NLST (National Lung Screening Trial Research Team. N Engl J Med. 2011 Aug. 4; 365(5): 395-409), there are several caveats to its unrestricted use. It has a low specificity (e.g., high "false" positive rate, 39.1% of all participants in the LDCT arm had at least one positive screen while only 3.6% of those screened with LDCT had a confirmed diagnosis of lung cancer) and low sensitivity (e.g., only about 30% of current lung cancer patients in the US meet NLST criteria).

Mammography identifies millions of breast nodules annually. Mammographic screening has reduced death rates from breast cancer from randomized trials (International Agency for Research on Cancer IARC. IARC Handbooks of Cancer Prevention. Vol. 7: Breast Cancer Screening. World Health Organization, Lyon, 2002; Andersson I, Aspegren K, Janzon L, et al. BMJ. 1988; 297(6654):943-8; Demissie K, Mills O F and Rhoads G G. J Clin Epidemiol. 1998; 51(2):81-91). Although mammography may be effective in reducing breast cancer mortality in certain populations, but it can also pose harm to women who participate. Additionally, mammographic screening often involves false-positives (related to the specificity of the test), overdiagnosis (true-positives that will not become clinically significant), false-negatives (related to the sensitivity of the test), discomfort associated with the test, radiation risk and anxiety. In many cases, there is a need for additional diagnosis procedures such as ultrasound or eventually histopathological diagnosis by biopsy techniques (e.g., fine-needle aspiration which does not always provide a definitive diagnosis regarding what the lesion in your breast is). Furthermore, less than 5 per 1,000 women who were screened actually have the breast cancer. Therefore, even with a specificity of 90%, most abnormal mammograms are false-positives (National Cancer Institute http://www.cancer.gov/cancertopics/pdq/screening/breast/healthprofessional/page8). Consequently, there is an unmet need for a noninvasive clinical test that would lead to less false positive results.

Pancreatic cancer up to date does not have any efficient screening methods available, which contributes to its high mortality rates, as most patients are discovered in late stages. Therefore, it is essential to find a non-invasive and accurate screening method for this fast-rising cancer incidence disease.

Accordingly, there exists a need for methods, compositions, and systems that can provide for classification and/or diagnosis of cancers. In particular, there is a need for diagnosis and/or classification of cancers at an early stage.

SUMMARY

Cancerous DNA alterations and progression can be detected by measuring changes of circulating cell-free DNA. Cell-free DNA (cfDNA) is short, extracellular, fragmented double-stranded DNA found in human biofluids like plasma, serum and even urine. The presence of double-stranded cell-free DNA (cfDNA) in healthy human plasma has been noted since 1948 (Mandel P, Metais P. C R Seances Soc Biol Fil 142: 241-243). Under conditions such as pregnancy, autoimmune disorders, myocardial infarction, and cancer, the concentration of cfDNA in plasma is significantly increased (Chang C P et al. Clin Chim Acta 327: 95-101; Galeazzi M et al. Autoimmun Rev 2: 50-55; Chiu R W, et al. Proc Natl Acad Sci USA 105: 20458-20463; Leon S A et al. Cancer Res 37: 646-650). Circulating tumor DNA (ctDNA) is a portion of circulating DNA specifically derived from cancer cells. ctDNA is present both unbound and bound to leukocytes and erythrocytes (Swarup V et al. FEBS Lett. 2007; 5:795-799). Most tests for detecting tumor-derived cfDNA target characteristic genetic or epigenetic modifications, such as mutations in tumor-suppressor genes, activated oncogenes, hypermethylation or chromosomal disorders, to guarantee that cancer cells are indeed the source of the detected cfDNA (Schwarzenbach H, et al. Nat Rev Cancer. 2011; 5:426-437). As cfDNA has a half-life of about 2 hours in blood (e.g., it is removed and regenerated in the circulation in 2 hours), analysis of cfDNA and more importantly tumor DNA (ctDNA) at any given moment gives an accurate view over patient's pathological state at any given moment without contaminating the analysis with information over past diseases. Therefore, cfDNA analysis is a very promising tool for cancer screening and monitoring.

DNA methylation (DNAme) is an important epigenetic mark in diverse species. DNA methylation in vertebrates is characterized by the addition of a methyl or hydroxymethyl group to the C5 position of cytosine, which occurs mainly in the context of CG dinucleotides. DNA hypermethylation is known to be a major mechanism for inactivation of cancer-associated genes, including tumor suppressor genes, in CRC and in other human cancers. Aberrant DNA methylation in blood, stool and/or urine sample(s) may be a powerful biomarker for the early detection of cancer (Oh T et al. J Mol Diagn. 2013 July; 15(4):498-507; Wittenberger T et al. Epigenomics. 2014 June; 6(3):311-27).

The present disclosure provides, among other things, methods for detecting (e.g., screening for) multiple types of cancers—for example, colorectal cancer (e.g., stage I, II, III, and/or undifferentiated stage), breast cancer (e.g., stage I, II, III, and/or undifferentiated stage), lung cancer (e.g., stage I, II, III, and/or undifferentiated stage), and/or pancreatic cancer (e.g., stage I, II, III, and/or undifferentiated stage), as well as systems and compositions related thereto. In various embodiments, the present disclosure provides methods for classification of subjects as having or not having any of a set of different cancer types—such as colorectal cancer (e.g., stage I, II, III, and/or undifferentiated stage), breast cancer (e.g., stage I, II, III, and/or undifferentiated stage), lung cancer (e.g., stage I, II, III, and/or undifferentiated stage), and/or pancreatic cancer (e.g., stage I, II, III, and/or undifferentiated stage). In some embodiments, the type of cancer remains undifferentiated—e.g., the test only indicates that the subject has one or more of the multiple cancer types. In other embodiments, the test further identifies which of the set of cancer types the individual has.

In various embodiments, the present disclosure provides methods for screening for the multiple cancer types that include determination of methylation status (e.g., the number, frequency, or pattern of methylation) at one or more methylation sites found within one or more markers within a sample (e.g., a blood sample, a blood product sample, a stool sample, a colorectal tissue sample) from a subject (e.g., a human subject), and compositions related thereto. For example, markers may include a methylation locus, e.g., a differentially methylated region (DMR) of deoxyribonucleic acid (DNA) of a human subject. In various embodiments, the present disclosure provides methods for classifying a subject as having and/or not having any of the set of cancer types being tested for—e.g., colorectal cancer (e.g., stage I, II, III, and/or undifferentiated stage), breast cancer (e.g., stage I, II, III, and/or undifferentiated stage), lung cancer (e.g., stage I, II, III, and/or undifferentiated stage), and/or pancreatic cancer (e.g., stage I, II, III, and/or undifferentiated stage) by determining methylation status for each of one or more methylation loci in cfDNA (cell free DNA), e.g., in ctDNA (circulating tumor DNA). In various embodiments, the present disclosure provides methods for screening that include determining a methylation status for each of one or more methylation loci in cfDNA, e.g., in ctDNA, using, for example, massive parallel sequencing (e.g., next generation sequencing), e.g., sequencing-by-synthesis, real-time (e.g., single-molecule) sequencing, bead emulsion sequencing, nanopore sequencing, quantitative polymerase chain reaction (qPCR) (e.g., methylation sensitive restriction enzyme quantitative polymerase chain reaction, MSRE-qPCR). Various compositions and methods provided herein provide sensitivity and specificity sufficient for clinical application in screening for conditions, including but not limited to, colorectal cancer (e.g., stage I, II, III, and/or undifferentiated stage), breast cancer (e.g., stage I, II, III, and/or undifferentiated stage), lung cancer (e.g., stage I, II, III, and/or undifferentiated stage), and/or pancreatic cancer (e.g., stage I, II, III, and/or undifferentiated stage). Various compositions and methods provided herein are useful in colorectal cancer (e.g., stage I, II, III, and/or undifferentiated stage), breast cancer (e.g., stage I, II, III, and/or undifferentiated stage), lung cancer (e.g., stage I, II, III, and/or undifferentiated stage), and/or pancreatic cancer (e.g., stage I, II, III, and/or undifferentiated stage) screening by analysis of an accessible tissue sample of a subject, e.g., a tissue sample that is blood or a blood component (e.g., cfDNA, e.g., ctDNA), or stool.

In one aspect, the invention is directed to a method of screening for multiple cancer types in a human subject, the method comprising: determining a methylation status of each of at least three screening markers (e.g., 3, 4, 5, 6, 7, 8, 9, 10, 11, 12, 13, 14, 15, 16, 17, 18, 19, 20, 21, 22, 23, 24, 25, 26, 27, 28, 29, or 30 screening markers) identified in a sample obtained from the subject, and determining whether the subject has any one or more of the multiple cancer types based at least in part on the determined methylation status of each of the at least three screening markers, wherein each of the at least three screening markers is a methylation locus comprising at least a portion of (e.g., at least 50% of) a differentially methylated region (DMR) selected from the DMRs of Table 11 (e.g., corresponding to SEQ ID NOs 82-111) [e.g., wherein the methylation locus comprises at least 50/6 of the DMR and wherein the portion of the methylation locus that overlaps with the DMR has at least 98% similarity with the overlapping portion of the DMR].

In certain embodiments, the method comprises screening for two, three, or all four of (i)-(iv) as follows: (i) colorectal cancer (e.g., stage I, II, III, and/or undifferentiated stage), (ii) breast cancer (e.g., stage I, II, III, and/or undifferentiated stage), (iii) lung cancer (e.g., stage I, II, III, and/or undifferentiated stage), and (iv) pancreatic cancer (e.g., stage I, II, III, and/or undifferentiated stage), either with or without identifying which of those cancer types the subject has.

In certain embodiments, each methylation locus comprises at least one (e.g., at least 2, at least 3, at least 4, or more) CpG dinucleotide.

In certain embodiments the sample comprises a blood sample, a blood product sample, a stool sample, or a tissue sample.

In certain embodiments, the sample comprises DNA that is isolated from blood or plasma of the human subject. In certain embodiments, the DNA is cell-free DNA of the human subject.

In another aspect, the invention is directed to a method of screening for multiple cancer types in a human subject, the method comprising: determining a methylation status of each of at least three screening markers (e.g., 3, 4, 5, 6, 7, 8, 9, 10, 11, 12, 13, 14, 15, 16, or 17 screening markers) identified in a sample obtained from the subject, and determining whether the subject has any one or more of the multiple cancer types based at least in part on the determined methylation status of each of the at least three screening markers, wherein each of the at least three screening markers is a methylation locus comprising at least a portion of (e.g., at least 50% of) a differentially methylated region (DMR) selected from the DMRs listed in Table 10 (e.g., corresponding to SEQ ID NOs: 82, 84, 86, 87, 89, 90, 93, 94, 96, 99-101, 103, 107, 109, 110, 111) [e.g., wherein the methylation locus comprises at least 50% of the DMR and wherein the portion of the methylation locus that overlaps with the DMR has at least 98% similarity with the overlapping portion of the DMR].

In certain embodiments, the method comprises screening for two, three, or all four of (i)-(iv) as follows: (i) colorectal cancer (e.g., stage I, II, III, and/or undifferentiated stage), (ii) breast cancer (e.g., stage I, II, III, and/or undifferentiated stage), (iii) lung cancer (e.g., stage I, II, III, and/or undifferentiated stage), and (iv) pancreatic cancer (e.g., stage I, II, III, and/or undifferentiated stage), either with or without identifying which of those cancer types the subject has.

In certain embodiments, each methylation locus comprises at least one (e.g., at least 2, at least 3, at least 4, or more) CpG dinucleotide.

In certain embodiments, the sample comprises a blood sample, a blood product sample, a stool sample, or a tissue sample.

In certain embodiments, the sample comprises DNA that is isolated from blood or plasma of the human subject. In certain embodiments, the DNA is cell-free DNA of the human subject.

In another aspect, the invention is directed to a method of screening for multiple cancer types in a human subject, the method comprising: determining a methylation status of each of at least three screening markers (e.g., 3, 4, 5, 6, 7, 8, or 9 screening markers) identified in a sample obtained from the subject, and determining whether the subject has any one or more of the multiple cancer types based at least in part on the determined methylation status of each of the at least three screening markers, wherein each of the at least three screening markers is a methylation locus comprising at least a portion of (e.g., at least 50% of) a differentially methylated region (DMR) selected from the DMRs listed in Table 9 (e.g., corresponding to SEQ ID NOs: 84, 89, 92, 93, 96, 99, 100, 107, and 109) [e.g., wherein the methylation locus comprises at least 50% of the DMR and wherein the portion of the methylation locus that overlaps with the DMR has at least 98% similarity with the overlapping portion of the DMR].

In certain embodiments, the method comprises screening for two, three, or all four of (i)-(iv) as follows: (i) colorectal cancer (e.g., stage I, II, III, and/or undifferentiated stage), (ii) breast cancer (e.g., stage I, II, III, and/or undifferentiated stage), (iii) lung cancer (e.g., stage I, II, III, and/or undifferentiated stage), and (iv) pancreatic cancer (e.g., stage I, II, III, and/or undifferentiated stage), either with or without identifying which of those cancer types the subject has.

In certain embodiments, the method comprises treating the one or more cancer types based on the determined methylation status of each of the at least three screening markers.

In certain embodiments, the one or more marker(s) comprises at least one (e.g., at least 2, at least 3, at least 4, or more) CpG dinucleotide.

In certain embodiments, the sample comprises a blood sample, a blood product sample, a stool sample, or a tissue sample.

In certain embodiments, the sample comprises DNA that is isolated from blood or plasma of the human subject. In certain embodiments, the DNA is cell-free DNA of the human subject.

In certain embodiments, methylation status is determined using quantitative polymerase chain reaction (qPCR).

In certain embodiments, methylation status is determined using massively parallel sequencing (e.g., next-generation sequencing) [e.g., sequencing by—synthesis, real-time (e.g., single-molecule) sequencing, bead emulsion sequencing, nanopore sequencing, or the like].

In another aspect, the invention is directed to a method of screening for multiple cancer types in a human subject, the method comprising: determining a methylation status of each of at least three screening markers (e.g., 3, 4, or 5 screening markers) identified in a sample obtained from the subject, and determining whether the subject has any one or more of the multiple cancer types based at least in part on the determined methylation status of each of the at least three screening markers, wherein each of the at least three screening markers is a methylation locus comprising at least a portion of (e.g., at least 50% of) a differentially methylated region (DMR) selected from the DMRs listed in Table 8 (e.g., corresponding to SEQ ID NOs: 83, 92, 96, 99, and 107) [e.g., wherein the methylation locus comprises at least 50% of the DMR and wherein the portion of the methylation locus that overlaps with the DMR has at least 98% similarity with the overlapping portion of the DMR].

In certain embodiments, the method comprises screening for two, three, or all four of (i)-(iv) as follows: (i) colorectal cancer (e.g., stage I, II, III, and/or undifferentiated stage), (ii) breast cancer (e.g., stage I, II, III, and/or undifferentiated stage), (iii) lung cancer (e.g., stage I, II, III, and/or undifferentiated stage), and (iv) pancreatic cancer (e.g., stage I, II, III, and/or undifferentiated stage), either with or without identifying which of those cancer types the subject has].

In certain embodiments, each methylation locus comprises at least one (e.g., at least 2, at least 3, at least 4, or more) CpG dinucleotide.

In certain embodiments, the sample comprises a blood sample, a blood product sample, a stool sample, or a tissue sample.

In certain embodiments, sample comprises DNA that is isolated from blood or plasma of the human subject. In certain embodiments, the DNA is cell-free DNA of the human subject.

In certain embodiments, methylation status is determined using quantitative polymerase chain reaction (qPCR).

In certain embodiments, methylation status is determined using massively parallel sequencing (e.g., next-generation sequencing) [e.g., sequencing by—synthesis, real-time (e.g., single-molecule) sequencing, bead emulsion sequencing, nanopore sequencing, or the like].

In another aspect, the invention is directed to a method of screening for multiple cancer types in a human subject, the method comprising: determining a methylation status of each of a plurality of screening markers (e.g., 2 or 3 screening markers) identified in a sample obtained from the subject, and determining whether the subject has any one or more of the multiple cancer types based at least in part on the determined methylation status of each of the plurality of screening markers, wherein each of the plurality of screening markers is a methylation locus comprising at least a portion of (e.g., at least 50% of) a differentially methylated region (DMR) selected from the DMRs listed in Table 7 (e.g., corresponding to SEQ ID NOs 91, 96, and 108) [e.g., wherein the methylation locus comprises at least 50% of the DMR and wherein the portion of the methylation locus that overlaps with the DMR has at least 98% similarity with the overlapping portion of the DMR].

In certain embodiments, the method comprises screening for two, three, or all four of (i)-(iv) as follows: (i) colorectal cancer (e.g., stage I, II, III, and/or undifferentiated stage), (ii) breast cancer (e.g., stage I, II, III, and/or undifferentiated stage), (iii) lung cancer (e.g., stage I, II, III, and/or undifferentiated stage), and (iv) pancreatic cancer (e.g., stage I, II, III, and/or undifferentiated stage), either with or without identifying which of those cancer types the subject has.

In certain embodiments, the method comprises treating the one or more cancer types based on the determined methylation status of each of the plurality of screening markers.

In certain embodiments, each methylation locus comprises at least one (e.g., at least 2, at least 3, at least 4, or more) CpG dinucleotide.

In certain embodiments, the sample comprises a blood sample, a blood product sample, a stool sample, or a tissue sample.

In certain embodiments, the sample comprises DNA that is isolated from blood or plasma of the human subject. In certain embodiments, the DNA is cell-free DNA of the human subject.

In certain embodiments, methylation status is determined using quantitative polymerase chain reaction (qPCR).

In certain embodiments, methylation status is determined using massively parallel sequencing (e.g., next-generation sequencing) [e.g., sequencing by—synthesis, real-time (e.g., single-molecule) sequencing, bead emulsion sequencing, nanopore sequencing, or the like].

In another aspect, the invention is directed to a method of screening for multiple cancer types in a human subject, the method comprising: determining a methylation status of each of one or more of the following (e.g., 1, 2, or all 3) screening markers, in deoxyribonucleic acid (DNA) from a sample obtained from a human subject: (a) a methylation locus within gene HOXA7; (b) a methylation locus within gene JAM2: and (c) a methylation locus comprising at least a portion of (e.g., at least 50% of) chr10:100830555-100830658 (SEQ ID NO: 96) (e.g., at least 50% of chr10: 100830555-100830658 (SEQ ID NO: 96)) [wherein the methylation locus comprises at least 50% of chr10: 100830555-100830658 and wherein the portion of the methylation locus that overlaps with chr10: 100830555-100830658 has at least 98% similarity with the overlapping portion of chr10: 100830555-100830658]; and diagnosing (or otherwise identifying) cancer in the human subject based at least on said determined methylation status(es) of the one or more screening markers.

In certain embodiments, the method comprises determining a methylation status for a methylation locus within gene HOXA7, wherein the methylation locus within gene HOXA7 comprises at least a portion of (e.g., at least 50/c of) HOXA7 '273 [chr7:27156273-27156352](SEQ ID NO: 91) [wherein the methylation locus within gene HOXA7 comprises at least 50% of HOXA7 '273 and wherein the portion of the methylation locus that overlaps with HOXA7 has at least 98% similarity with the overlapping portion of HOXA7 '273].

In certain embodiments, the method comprises determining a methylation status for a methylation locus within gene JAM2, wherein the methylation locus within gene JAM2 comprises at least a portion of (e.g., at least 50% of) JAM2 '320 [chr21:25640320-25640399](SEQ ID NO: 108) [wherein the methylation locus within gene JAM2 comprises at least 50% of JAM2 '320 and wherein the portion of the methylation locus that overlaps with JAM2 has at least 98% similarity with the overlapping portion of JAM2 '320].

In certain embodiments, the method comprises determining a methylation status for a methylation locus within gene HOXA7 wherein the methylation locus within gene HOXA7 comprises at least one (e.g., at least 2, at least 3, at least 4, or more) CpG dinucleotide.

In certain embodiments, the method comprises determining a methylation status for a methylation locus within gene JAM2, wherein the methylation locus within gene JAM2 comprises at least one (e.g., at least 2, at least 3, at least 4, or more) CpG dinucleotide.

In certain embodiments, the method comprises screening for two, three, or all four of (i)-(iv) as follows: (i) colorectal cancer (e.g., stage I, II, III, and/or undifferentiated stage), (ii) breast cancer (e.g., stage I, II, III, and/or undifferentiated stage), (iii) lung cancer (e.g., stage I, II, III, and/or undifferentiated stage), and (iv) pancreatic cancer (e.g., stage I, II, III, and/or undifferentiated stage), either with or without identifying which of those cancer types the human subject has.

In certain embodiments, the sample comprises a blood sample, a blood product sample, a stool sample, or a tissue sample.

In certain embodiments, the sample comprises DNA that is isolated from blood or plasma of the human subject. In certain embodiments, the DNA is cell-free DNA of the human subject.

In certain embodiments, methylation status is determined using quantitative polymerase chain reaction (qPCR).

In certain embodiments, methylation status is determined using massively parallel sequencing (e.g., next-generation sequencing) [e.g., sequencing by—synthesis, real-time (e.g., single-molecule) sequencing, bead emulsion sequencing, nanopore sequencing, or the like].

In another aspect, the invention is directed to a method of screening for multiple cancer types in a human subject, the method comprising: determining a methylation status of each of one or more of the following (e.g., 1, 2, 3, 4, or all 5) screening markers, in deoxyribonucleic acid (DNA) from a sample obtained from a human subject: (a) a methylation locus within gene KLK10; (b) a methylation locus within gene HOXA7; (c) a methylation locus comprising at least a portion of chr10:100830555-100830658 (SEQ ID NO: 96) (e.g., at least 50% of chr10:100830555-100830658 (SEQ ID NO: 96) [wherein the methylation locus comprises at least 50% of chr10: 100830555-100830658 and wherein the portion of the methylation locus that overlaps with chr10: 100830555-100830658 has at least 98% similarity with the overlapping portion of chr10: 100830555-100830658]); (d) a methylation locus within gene TXNRD1; and (e) a methylation locus within gene THBD; and diagnosing (or otherwise identifying) cancer in the human subject based at least on said determined methylation status(es) of the one or more screening markers.

In certain embodiments, the method comprises determining a methylation status for a methylation locus within gene KLK10, wherein the methylation locus within gene KLK10 comprises least a portion of (e.g., at least 50% of) KLK10 '613 [chr19:51019613-51019705](SEQ ID NO: 83) [wherein the methylation locus within gene KLK10 comprises at least 50% of KLK10 '613 and wherein the portion of the methylation locus that overlaps with KLK10 has at least 98% similarity with the overlapping portion of KLK10 '613].

In certain embodiments, the method comprises determining a methylation status for a methylation locus within gene HOXA7, wherein the methylation locus within gene HOXA7 comprises at least a portion of (e.g., at least 50% of) HOXA7 '291 [chr7:27156291-27156403](SEQ ID NO: 92) [wherein the methylation locus within gene HOXA7 comprises at least 500 of HOXA7 '291 and wherein the portion of the methylation locus that overlaps with HOXA7 has at least 98% similarity with the overlapping portion of HOXA7 '291].

In certain embodiments, the method comprises determining a methylation status for a methylation locus within gene TXNRD1, wherein the methylation locus within gene TXNRD1 comprises at least a portion of (e.g., at least 50% of) TXNRD1 '675 [chr12:104215675-104215784] (SEQ ID NO: 99) [wherein the methylation locus within gene TXNRD1 comprises at least 50% of TXNRD1 '675 and wherein the portion of the methylation locus that overlaps with TXNRD1 has at least 98% similarity with the overlapping portion of TXNRD1 '675].

In certain embodiments, the method comprises determining a methylation status for a methylation locus within gene THBD, wherein the methylation locus within gene THBD comprises at least a portion of (e.g., at least 50%/c of) THBD '354 [chr20:23049354-23049500](SEQ ID NO: 107) [wherein the methylation locus within gene THBD comprises at least 50% of THBD '354 and wherein the portion of the methylation locus that overlaps with THBD has at least 98% similarity with the overlapping portion of THBD '354].

In certain embodiments, the method comprises screening for two, three, or all four of (i)-(iv) as follows: (i) colorectal cancer (e.g., stage I, II, III, and/or undifferentiated stage), (ii) breast cancer (e.g., stage I, II, III, and/or undifferentiated stage), (iii) lung cancer (e.g., stage I, II, III, and/or undifferentiated stage), and (iv) pancreatic cancer (e.g., stage I, II, III, and/or undifferentiated stage), either with or without identifying which of those cancer types the subject has.

In certain embodiments, the method comprises determining a methylation status for a methylation locus within gene KLK10, wherein the methylation locus within gene KLK10 comprises at least one (e.g., at least 2, at least 3, at least 4, or more) CpG dinucleotide.

In certain embodiments, the method comprises determining a methylation status for a methylation locus within gene HOXA7, wherein the methylation locus within gene HOXA7 comprises at least one (e.g., at least 2, at least 3, at least 4, or more) CpG dinucleotide.

In certain embodiments, the method comprises determining a methylation status for a methylation locus within gene TXNRD1, wherein the methylation locus within gene TXNRD1 comprises at least one (e.g., at least 2, at least 3, at least 4, or more) CpG dinucleotide.

In certain embodiments, the method comprises determining a methylation status for a methylation locus within gene THBD, wherein the methylation locus within gene THBD comprises at least one (e.g., at least 2, at least 3, at least 4, or more) CpG dinucleotide.

In certain embodiments, the sample comprises a blood sample, a blood product sample, a stool sample, or a tissue sample.

In certain embodiments, the sample comprises DNA that is isolated from blood or plasma of the human subject. In certain embodiments, the DNA is cell-free DNA of the human subject.

In certain embodiments, methylation status is determined using quantitative polymerase chain reaction (qPCR).

In certain embodiments, methylation status is determined using massively parallel sequencing (e.g., next-generation sequencing) [e.g., sequencing by—synthesis, real-time (e.g., single-molecule) sequencing, bead emulsion sequencing, nanopore sequencing, or the like].

In certain embodiments, the methods, further comprise, for a subject determined by the method to have one or more of the multiple cancer types, determining which of the multiple cancer types the subject has based at least in part on a determined methylation status of each of at least three cancer-differentiating markers (e.g., 3, 4, 5, 6, 7, 8, 9, 10, 11, 12, 13, or 14 markers) selected from the DMRs of Table 15 (e.g., corresponding to SEQ ID NOs: 90, 93, 95, 112-122), said at least three cancer-differentiating markers identified in a sample obtained from the subject (i.e., the same or a different sample as the sample obtained in the methods described herein).

In certain embodiments, the methods, further comprise, for a subject determined by the method to have one or more of the multiple cancer types, determining which of the multiple cancer types the subject has based at least in part on a determined methylation status of each of at least three cancer-differentiating markers (e.g., 3, 4, 5, 6, or 7 markers) selected from Table 13 (e.g., corresponding to SEQ ID NOs: 90, 93, 95, 112, 115, 118, and 119,
said at least three cancer-differentiating markers identified in a sample obtained from the subject (i.e., the same or a different sample as the sample obtained in the methods described herein).

In certain embodiments, the sample comprises DNA that is isolated from blood or plasma of the human subject. In certain embodiments, the DNA is cell-free DNA of the human subject.

In certain embodiments, methylation status is determined using quantitative polymerase chain reaction (qPCR).

In certain embodiments, methylation status is determined using methylation sensitive restriction enzyme quantitative polymerase chain reaction (MSRE-qPCR).

In certain embodiments, methylation status is determined using massively parallel sequencing (e.g., next-generation sequencing) [e.g., sequencing by—synthesis, real-time (e.g., single-molecule) sequencing, bead emulsion sequencing, nanopore sequencing, or the like].

In certain embodiments, each methylation locus is equal to or less than 5000 bp in length (e.g., 4,000 bp, 3,000 bp, 2,000 bp, 1,000 bp, 950 bp, 900 bp, 850 bp, 800 bp, 750 bp, 700 bp, 650 bp, 600 bp, 550 bp, 500 bp, 450 bp, 400 bp, 350 bp, 300 bp, 250 bp, 200 bp, or 150 bp or less) (e.g., and wherein each methylation locus is equal to or greater than 10 bp in length).

In another aspect, the invention is directed to a kit for use in a method as described herein, the kit comprising one or more oligonucleotide primer pairs for amplification of one or more corresponding methylation locus/loci.

In another aspect, the invention is directed to a diagnostic qPCR reaction for screening for multiple cancer types in a human subject (e.g., in a method described herein), the diagnostic qPCR reaction including: (a) human DNA, (b) a polymerase, and (c) one or more oligonucleotide primer pairs for amplification of one or more corresponding methylation locus/loci, and, optionally, at least one methylation sensitive restriction enzyme.

In certain embodiments, each of the one or more corresponding methylation loci each comprise at least one methylation sensitive restriction enzyme (MSRE) cleavage site (e.g., at least 2, 3, 4, 5, 6, 7, 8, 9, 10, 11, 12, 13, 14, or 15 MSRE cleavage sites).

In another aspect, the invention is directed to a kit for use in a method as described herein, the kit comprising one or more oligonucleotide capture baits (e.g., one or more biotinylated oligonucleotide probes) for capturing one or more corresponding methylation locus/loci (e.g., for hybridizing to the region/regions of interest).

In certain embodiments, the method comprises determining the methylation status of each of the one or more screening markers (e.g., and/or determining the methylation status of each of the one or more cancer-differentiating markers) using next generation sequencing (NGS).

In certain embodiments, the method comprises using one or more oligonucleotide capture baits (e.g., biotinylated oligonucleotide probes) that enrich for a target region to capture one or more corresponding methylation locus/loci (e.g., followed by library preparation and sequencing, e.g., wherein the sample is either bisulfite converted or enzymatically converted prior to capture).

In various aspects, methods as described herein may further comprise treatment of a cancer (e.g., colon cancer, pancreatic cancer, lung cancer, breast cancer) based on, at least, the methylation status of one or more methylation loci.

In certain embodiments, the method further comprises using one or more oligonucleotide capture baits (e.g., biotinylated oligonucleotide probes) that enrich for a target region to capture one or more corresponding methylation locus/loci (e.g., followed by library preparation and sequencing, e.g., wherein the sample is either bisulfite converted or enzymatically converted prior to capture). In various aspects, methods and compositions of the present invention can be used in combination with biomarkers known in the art, e.g., as disclosed in U.S. Pat. Nos. 10,006,925 and 63,011,970, which are herein incorporated by reference in their entirety.

DEFINITIONS

A or An: The articles "a" and "an" are used herein to refer to one or to more than one (i.e., to at least one) of the grammatical object of the article. By way of example, "an element" refers to one element or more than one element.

About: The term "about", when used herein in reference to a value, refers to a value that is similar, in context, to the referenced value. In general, those skilled in the art, familiar with the context, will appreciate the relevant degree of variance encompassed by "about" in that context. For example, in some embodiments, e.g., as set forth herein, the term "about" can encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or with a fraction of a percent, of the referred value.

Advanced Adenoma: As used herein, the term "advanced adenoma" typically refers to refer to cells that exhibit first indications of relatively abnormal, uncontrolled, and/or autonomous growth but are not yet classified as cancerous alterations. In the context of colon tissue, "advanced adenoma" refers to neoplastic growth that shows signs of high grade dysplasia, and/or size that is >=10 mm, and/or villious histological type, and/or serrated histological type with any type of dysplasia.

Administration: As used herein, the term "administration" typically refers to the administration of a composition to a subject or system, for example to achieve delivery of an agent that is, is included in, or is otherwise delivered by, the composition.

Agent: As used herein, the term "agent" refers to an entity (e.g., for example, a small molecule, peptide, polypeptide, nucleic acid, lipid, polysaccharide, complex, combination, mixture, system, or phenomenon such as heat, electric current, electric field, magnetic force, magnetic field, etc.).

Amelioration: As used herein, the term "amelioration" refers to the prevention, reduction, palliation, or improvement of a state of a subject. Amelioration includes, but does not require, complete recovery or complete prevention of a disease, disorder or condition.

Amplicon or amplicon molecule: As used herein, the term "amplicon" or "amplicon molecule" refers to a nucleic acid molecule generated by transcription from a template nucleic acid molecule, or a nucleic acid molecule having a sequence complementary thereto, or a double-stranded nucleic acid including any such nucleic acid molecule. Transcription can be initiated from a primer.

Amplification: As used herein, the term "amplification" refers to the use of a template nucleic acid molecule in combination with various reagents to generate further nucleic acid molecules from the template nucleic acid molecule, which further nucleic acid molecules may be identical to or similar to (e.g., at least 70% identical, e.g., at least 75%, 80%, 85%, 90%, 91%, 92%, 93%, 94%, 95%, 96%, 97%, 98%, 99%, or 100% identical to) a segment of the template nucleic acid molecule and/or a sequence complementary thereto.

Amplification reaction mixture: As used herein, the terms "amplification reaction mixture" or "amplification reaction" refer to a template nucleic acid molecule together with reagents sufficient for amplification of the template nucleic acid molecule.

Biological Sample: As used herein, the term "biological sample" typically refers to a sample obtained or derived from a biological source (e.g., a tissue or organism or cell culture) of interest, as described herein. In some embodiments, e.g., as set forth herein, a biological source is or includes an organism, such as an animal or human. In some embodiments, e.g., as set forth herein, a biological sample is or include biological tissue or fluid. In some embodiments, e.g., as set forth herein, a biological sample can be or include cells, tissue, or bodily fluid. In some embodiments, e.g., as set forth herein, a biological sample can be or include blood, blood cells, cell-free DNA, free floating nucleic acids, ascites, biopsy samples, surgical specimens, cell-containing body fluids, sputum, saliva, feces, urine, cerebrospinal fluid, peritoneal fluid, pleural fluid, lymph, gynecological fluids, secretions, excretions, skin swabs, vaginal swabs, oral swabs, nasal swabs, washings or lavages such as a ductal lavages or broncheoalveolar lavages, aspirates, scrapings, bone marrow. In some embodiments, e.g., as set forth herein, a biological sample is or includes cells obtained from a single subject or from a plurality of subjects. A sample can be a "primary sample" obtained directly from a biological source, or can be a "processed sample." A biological sample can also be referred to as a "sample."

Biomarker: As used herein, the term "biomarker," consistent with its use in the art, refers to a to an entity whose presence, level, or form, correlates with a particular biological event or state of interest, so that it is considered to be a "marker" of that event or state. Those of skill in the art will appreciate, for instance, in the context of a DNA biomarker, that a biomarker can be or include a locus (such as one or more methylation loci) and/or the status of a locus (e.g., the status of one or more methylation loci). To give but a few examples of biomarkers, in some embodiments, e.g., as set forth herein, a biomarker can be or include a marker for a particular disease, disorder or condition, or can be a marker for qualitative of quantitative probability that a particular disease, disorder or condition can develop, occur, or reoccur, e.g., in a subject. In some embodiments, e.g., as set forth herein, a biomarker can be or include a marker for a particular therapeutic outcome, or qualitative of quantitative probability thereof. Thus, in various embodiments, e.g., as set forth herein, a biomarker can be predictive, prognostic, and/or diagnostic, of the relevant biological event or state of interest. A biomarker can be an entity of any chemical class. For example, in some embodiments, e.g., as set forth herein, a biomarker can be or include a nucleic acid, a polypeptide, a lipid, a carbohydrate, a small molecule, an inorganic agent (e.g., a metal or ion), or a combination thereof. In some embodiments, e.g., as set forth herein, a biomarker is a cell surface marker. In some embodiments, e.g., as set forth herein, a biomarker is intracellular. In some embodiments, e.g., as set forth herein, a biomarker is found outside of cells (e.g., is secreted or is otherwise generated or present outside of cells, e.g., in a body fluid such as blood, urine, tears, saliva, cerebrospinal fluid, and the like). In some embodiments, e.g., as set forth herein, a biomarker is methylation status of a methylation locus. In some instances, e.g., as set forth herein, a biomarker may be referred to as a "marker."

To give but one example of a biomarker, in some embodiments e.g., as set forth herein, the term refers to expression of a product encoded by a gene, expression of which is characteristic of a particular tumor, tumor subclass, stage of tumor, etc. Alternatively or additionally, in some embodiments, e.g., as set forth herein, presence or level of a particular marker can correlate with activity (or activity level) of a particular signaling pathway, for example, of a signaling pathway the activity of which is characteristic of a particular class of tumors.

Those of skill in the art will appreciate that a biomarker may be individually determinative of a particular biological event or state of interest, or may represent or contribute to a determination of the statistical probability of a particular biological event or state of interest. Those of skill in the art will appreciate that markers may differ in their specificity and/or sensitivity as related to a particular biological event or state of interest.

Blood component: As used herein, the term "blood component" refers to any component of whole blood, including red blood cells, white blood cells, plasma, platelets, endothelial cells, mesothelial cells, epithelial cells, and cell-free DNA. Blood components also include the components of plasma, including proteins, metabolites, lipids, nucleic acids, and carbohydrates, and any other cells that can be present in blood, e.g., due to pregnancy, organ transplant, infection, injury, or disease.

Cancer: As used herein, the terms "cancer," "malignancy," "neoplasm," "tumor," and "carcinoma," are used interchangeably to refer to a disease, disorder, or condition in which cells exhibit or exhibited relatively abnormal, uncontrolled, and/or autonomous growth, so that they display or displayed an abnormally elevated proliferation rate and/or aberrant growth phenotype. In some embodiments, e.g., as set forth herein, a cancer can include one or more tumors. In some embodiments e.g., as set forth herein, a cancer can be or include cells that are precancerous (e.g., benign), malignant, pre-metastatic, metastatic, and/or non-metastatic. In some embodiments e.g., as set forth herein, a cancer can be or include a solid tumor. In some embodiments e.g., as set forth herein, a cancer can be or include a hematologic tumor. In general, examples of different types of cancers known in the art include, for example, colorectal cancer, hematopoietic cancers including leukemias, lymphomas (Hodgkin's and non-Hodgkin's), myelomas and myeloproliferative disorders: sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Chemotherapeutic agent: As used herein, the term "chemotherapeutic agent," consistent with its use in the art, refers to one or more agents known, or having characteristics known to, treat or contribute to the treatment of cancer. In particular, chemotherapeutic agents include pro-apoptotic, cytostatic, and/or cytotoxic agents. In some embodiments e.g., as set forth herein, a chemotherapeutic agent can be or include alkylating agents, anthracyclines, cytoskeletal disruptors (e.g., microtubule targeting moieties such as taxanes, maytansine, and analogs thereof, of), epothilones, histone deacetylase inhibitors HDACs), topoisomerase inhibitors (e.g., inhibitors of topoisomerase I and/or topoisomerase II), kinase inhibitors, nucleotide analogs or nucleotide precursor analogs, peptide antibiotics, platinum-based agents, retinoids, *vinca* alkaloids, and/or analogs that share a relevant anti-proliferative activity. In some particular embodiments e.g., as set forth herein, a chemotherapeutic agent can be or include of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g., DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, or a combination thereof. In some embodiments e.g., as set forth herein, a chemotherapeutic agent can be utilized in the context of an antibody-drug conjugate. In some embodiments e.g., as set forth herein, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments e.g., as set forth herein, a chemotherapeutic agent can be or comprise of farnesyl-thiosalicylic acid (FTS), 4-(4-Chloro-2-methylphenoxy)-N-hydroxybutanamide (CMH), estradiol (E2), tetramethoxystilbene (TMS), S-tocatrienol, salinomycin, or curcumin.

Combination therapy: As used herein, the term "combination therapy" refers to administration to a subject of to two or more agents or regimens such that the two or more agents or regimens together treat a disease, condition, or disorder of the subject. In some embodiments, e.g., as set forth herein, the two or more therapeutic agents or regimens can be administered simultaneously, sequentially, or in overlapping dosing regimens. Those of skill in the art will appreciate that combination therapy includes but does not require that the two agents or regimens be administered together in a single composition, nor at the same time.

Comparable: As used herein, the term "comparable" refers to members within sets of two or more conditions, circumstances, agents, entities, populations, etc., that may not be identical to one another but that are sufficiently similar to permit comparison there between, such that one of skill in the art will appreciate that conclusions can reasonably be drawn based on differences or similarities observed. In some embodiments, e.g., as sort forth herein, comparable sets of conditions, circumstances, agents, entities, populations, etc. are typically characterized by a plurality of substantially identical features and zero, one, or a plurality of differing features. Those of ordinary skill in the art will understand, in context, what degree of identity is required to render members of a set comparable. For example, those of ordinary skill in the art will appreciate that members of sets of conditions, circumstances, agents, entities, populations, etc., are comparable to one another when characterized by a sufficient number and type of substantially identical features to warrant a reasonable conclusion that differences observed can be attributed in whole or part to non-identical features thereof.

Detectable moiety: The term "detectable moiety" as used herein refers to any element, molecule, functional group, compound, fragment, or other moiety that is detectable. In some embodiments, e.g., as sort forth herein, a detectable moiety is provided or utilized alone. In some embodiments, e.g., as sort forth herein, a detectable moiety is provided and/or utilized in association with (e.g., joined to) another agent. Examples of detectable moieties include, but are not limited to, various ligands, radionuclides (e.g., $^{3}$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99m}$Tc, $^{177}$Lu, $^{89}$Zr etc.), fluorescent dyes, chemiluminescent agents, bioluminescent agents, spectrally resolvable inorganic fluorescent semiconductors nanocrystals (i.e., quantum dots), metal nanoparticles, nanoclusters, paramagnetic metal ions, enzymes, colorimetric labels, biotin, dioxigenin, haptens, and proteins for which antisera or monoclonal antibodies are available.

Diagnosis: As used herein, the term "Diagnosis" refers to determining whether, and/or the qualitative of quantitative probability that, a subject has or will develop a disease, disorder, condition, or state. For example, in diagnosis of cancer, diagnosis can include a determination regarding the risk, type, stage, malignancy, or other classification of a cancer. In some instances, e.g., as sort forth herein, a diagnosis can be or include a determination relating to prognosis and/or likely response to one or more general or particular therapeutic agents or regimens.

Diagnostic information: As used herein, the term "diagnostic information" refers to information useful in providing a diagnosis. Diagnostic information can include, without limitation, biomarker status information.

Differentially methylated: As used herein, the term "differentially methylated" describes a methylation site for which the methylation status differs between a first condition and a second condition. A methylation site that is differentially methylated can be referred to as a differentially methylated site. In some instances, e.g., as sort forth herein, a DMR is defined by the amplicon produced by amplification using oligonucleotide primers, e.g., a pair of oligonucleotide primers selected for amplification of the DMR or for amplification of a DNA region of interest present in the amplicon. In some instances, e.g., as sort forth herein, a DMR is defined as a DNA region amplified by a pair of oligonucleotide primers, including the region having the sequence of, or a sequence complementary to, the oligonucleotide primers. In some instances, e.g., as sort forth herein, a DMR is defined as a DNA region amplified by a pair of oligonucleotide primers, excluding the region having the sequence of, or a sequence complementary to, the oligonucleotide primers. As used herein, a specifically provided DMR can be unambiguously identified by the name of an associated gene followed by three digits of a starting position, such that, for example, a DMR starting at position 29921434 of ALK can be identified as ALK '434. As used herein, a specifically provided DMR can be unambiguously identified by the chromosome number followed by the starting and ending positions of a DMR. For example, a DMR identified in Table 1 may be identified as HOXA7 '916 or ch7:27155916-27156027.

Differentially methylated region: As used herein, the term "differentially methylated region" (DMR) refers to a DNA region that includes one or more differentially methylated sites. A DMR that includes a greater number or frequency of methylated sites under a selected condition of interest, such as a cancerous state, can be referred to as a hypermethylation DMR. A DMR that includes a smaller number or frequency of methylated sites under a selected condition of interest, such as a cancerous state, can be referred to as a hypomethylation DMR. A DMR that is a methylation biomarker for colorectal cancer can be referred to as a colorectal cancer DMR. In some instances, e.g., as set forth herein, a DMR can be a single nucleotide, which single nucleotide is a methylation site. In some instances, e.g., as set forth herein, a DMR has a length of at least 10, at least 15, at least 20, at least 30, at least 50, or at least 75 base pairs. In some instances, e.g., as set forth herein, a DMR has a length of equal to or less than 5000 bp, 4,000 bp, 3,000 bp, 2,000 bp, 1,000 bp, 950 bp, 900 bp, 850 bp, 800 bp, 750 bp, 700 bp, 650 bp, 600 bp, 550 bp, 500 bp, 450 bp, 400 bp, 350 bp, 300 bp, 250 bp, 200 bp, 150 bp, 100 bp, 50 bp, 40 bp, 30 bp, 20 bp, or 10 bp (e.g., where methylation status is determined using quantitative polymerase chain reaction (qPCR), e.g., methylation sensitive restriction enzyme quantitative polymerase chain reaction (MSRE-qPCR)). In some instances, e.g., as set forth herein, a DMR that is a methylation biomarker for advanced adenoma may also be useful in identification of colorectal cancer.

DNA region: As used herein, "DNA region" refers to any contiguous portion of a larger DNA molecule. Those of skill in the art will be familiar with techniques for determining whether a first DNA region and a second DNA region correspond, based, e.g., on sequence similarity (e.g, sequence identity or homology) of the first and second DNA regions and/or context (e.g., the sequence identity or homology of nucleic acids upstream and/or downstream of the first and second DNA regions).

Except as otherwise specified herein, sequences found in or relating to humans (e.g., that hybridize to human DNA) are found in, based on, and/or derived from the example representative human genome sequence commonly referred to, and known to those of skill in the art, as *Homo sapiens* (human) genome assembly GRCh38, hg38, and/or Genome Reference Consortium Human Build 38. Those of skill in the art will further appreciate that DNA regions of hg38 can be referred to by a known system including identification of particular nucleotide positions or ranges thereof in accordance with assigned numbering.

Dosing regimen: As used herein, the term "dosing regimen" can refer to a set of one or more same or different unit doses administered to a subject, typically including a plurality of unit doses administration of each of which is separated from administration of the others by a period of time. In various embodiments, e.g., as set forth herein, one or more or all unit doses of a dosing regimen may be the same or can vary (e.g., increase over time, decrease over time, or be adjusted in accordance with the subject and/or with a medical practitioner's determination). In various embodiments, e.g., as set forth herein, one or more or all of the periods of time between each dose may be the same or can vary (e.g., increase over time, decrease over time, or be adjusted in accordance with the subject and/or with a medical practitioner's determination). In some embodiments, e.g., as set forth herein, a given therapeutic agent has a recommended dosing regimen, which can involve one or more doses. Typically, at least one recommended dosing regimen of a marketed drug is known to those of skill in the art. In some embodiments, e.g., as set forth herein, a dosing regimen is correlated with a desired or beneficial outcome when administered across a relevant population (i.e., is a therapeutic dosing regimen).

Downstream: As used herein, the term "downstream" means that a first DNA region is closer, relative to a second DNA region, to the C-terminus of a nucleic acid that includes the first DNA region and the second DNA region.

Gene: As used herein, the term "gene" refers to a single DNA region, e.g., in a chromosome, that includes a coding sequence that encodes a product (e.g., an RNA product and/or a polypeptide product), together with all, some, or none of the DNA sequences that contribute to regulation of the expression of coding sequence. In some embodiments, e.g., as set forth herein, a gene includes one or more non-coding sequences. In some particular embodiments, e.g., as set forth herein, a gene includes exonic and intronic sequences. In some embodiments, e.g., as set forth herein, a gene includes one or more regulatory elements that, for example, can control or impact one or more aspects of gene expression (e.g., cell-type-specific expression, inducible expression, etc.). In some embodiments, e.g., as set forth herein, a gene includes a promoter. In some embodiments, e.g., as set forth herein, a gene includes one or both of a (i) DNA nucleotides extending a predetermined number of nucleotides upstream of the coding sequence and (ii) DNA nucleotides extending a predetermined number of nucleotides downstream of the coding sequence. In various embodiments, e.g., as set forth herein, the predetermined number of nucleotides can be 500 bp, 1 kb, 2 kb, 3 kb, 4 kb, 5 kb, 10 kb, 20 kb, 30 kb, 40 kb, 50 kb, 75 kb, or 100 kb.

Homology: As used herein, the term "homology" refers to the overall relatedness between polymeric molecules, e.g., between nucleic acid molecules (e.g., DNA molecules and/or RNA molecules) and/or between polypeptide molecules. Those of skill in the art will appreciate that homology can be defined, e.g., by a percent identity or by a percent homology (sequence similarity). In some embodiments, e.g., as set forth herein, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, e.g., as set forth herein, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Hybridize: As used herein, "hybridize" refers to the association of a first nucleic acid with a second nucleic acid to form a double-stranded structure, which association occurs through complementary pairing of nucleotides. Those of skill in the art will recognize that complementary sequences, among others, can hybridize. In various embodiments, e.g., as set forth herein, hybridization can occur, for example, between nucleotide sequences having at least 70% complementarity, e.g., at least 75%, 80%, 85%, 90%, 91%, 92%, 93%, 94%, 95%, 96%, 97%, 98%, 990, or 100% complementarity. Those of skill in the art will further appreciate that whether hybridization of a first nucleic acid and a second nucleic acid does or does not occur can dependence upon various reaction conditions. Conditions under which hybridization can occur are known in the art.

Hypomethylation: As used herein, the term "hypomethylation" refers to the state of a methylation locus having at least one fewer methylated nucleotides in a state of interest as compared to a reference state (e.g., at least one fewer methylated nucleotides in colorectal cancer than in a healthy control).

Hypermethylation: As used herein, the term "hypermethylation" refers to the state of a methylation locus having at least one more methylated nucleotide in a state of interest as compared to a reference state (e.g., at least one more methylated nucleotide in colorectal cancer than in a healthy control).

Identity, identical: As used herein, the terms "identity" and "identical" refers to the overall relatedness between polymeric molecules, e.g., between nucleic acid molecules (e.g., DNA molecules and/or RNA molecules) and/or between polypeptide molecules. Methods for the calculation of a percent identity as between two provided sequences are known in the art. Calculation of the percent identity of two nucleic acid or polypeptide sequences, for example, can be performed by aligning the two sequences (or the complement of one or both sequences) for optimal comparison purposes (e.g., gaps can be introduced in one or both of a first and a second sequences for optimal alignment and non-identical sequences can be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences and, optionally, taking into account the number of gaps and the length of each gap, which may need to be introduced for optimal alignment of the two sequences. The comparison of sequences and determination of percent identity between two sequences can be accomplished using a computational algorithm, such as BLAST (basic local alignment search tool).

Improved, increased, or reduced: As used herein, these terms, or grammatically comparable comparative terms, indicate values that are relative to a comparable reference measurement. For example, in some embodiments, e.g., as set forth herein, an assessed value achieved with an agent of interest may be "improved" relative to that obtained with a comparable reference agent or with no agent. Alternatively or additionally, in some embodiments, e.g., as set forth herein, an assessed value in a subject or system of interest may be "improved" relative to that obtained in the same subject or system under different conditions or at a different point in time (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc.). In some embodiments, e.g., as set forth herein, comparative terms refer to statistically relevant differences (e.g., differences of a prevalence and/or magnitude sufficient to achieve statistical relevance). Those of skill in the art will be aware, or will readily be able to determine, in a given context, a degree and/or prevalence of difference that is required or sufficient to achieve such statistical significance.

Methylation: As used herein, the term "methylation" includes methylation at any of (i) C5 position of cytosine; (ii) N4 position of cytosine; and (iii) the N6 position of adenine. Methylation also includes (iv) other types of nucleotide methylation. A nucleotide that is methylated can be referred to as a "methylated nucleotide" or "methylated nucleotide base." In certain embodiments, e.g., as set forth herein, methylation specifically refers to methylation of cytosine residues. In some instances, methylation specifically refers to methylation of cytosine residues present in CpG sites.

Methylation assay: As used herein, the term "methylation assay" refers to any technique that can be used to determine the methylation status of a methylation locus.

Methylation biomarker: As used herein, the term "methylation biomarker" refers to a biomarker that is or includes at least one methylation locus and/or the methylation status of at least one methylation locus, e.g., a hypermethylated locus. In particular, a methylation biomarker is a biomarker characterized by a change between a first state and a second state (e.g., between a cancerous state and a non-cancerous state) in methylation status of one or more nucleic acid loci.

Methylation locus: As used herein, the term "methylation locus" refers to a DNA region that includes at least one differentially methylated region. A methylation locus that includes a greater number or frequency of methylated sites under a selected condition of interest, such as a cancerous state, can be referred to as a hypermethylated locus. A methylation locus that includes a smaller number or frequency of methylated sites under a selected condition of interest, such as a cancerous state, can be referred to as a hypomethylated locus. In some instances, e.g., as set forth herein, a methylation locus has a length of at least 10, at least 15, at least 20, at least 30, at least 50, or at least 75 base pairs. In some instances, e.g., as set forth herein, a methylation locus has a length of less than 5000 bp, 4,000 bp, 3,000 bp, 2,000 bp, 1,000 bp, 950 bp, 900 bp, 850 bp, 800 bp, 750 bp, 700 bp, 650 bp, 600 bp, 550 bp, 500 bp, 450 bp, 400 bp, 350 bp, 300 bp, 250 bp, 200 bp, 150 bp, 100 bp, 50 bp, 40 bp, 30 bp, 20 bp, or 10 bp (e.g., where methylation status is determined using quantitative polymerase chain reaction (qPCR), e.g., methylation sensitive restriction enzyme quantitative polymerase chain reaction (MSRE-qPCR)).

Methylation site: As used herein, a methylation site refers to a nucleotide or nucleotide position that is methylated in at least one condition. In its methylated state, a methylation site can be referred to as a methylated site.

Methylation status: As used herein, "methylation status," "methylation state," or "methylation profile" refer to the number, frequency, or pattern of methylation at methylation sites within a methylation locus. Accordingly, a change in methylation status between a first state and a second state can be or include an increase in the number, frequency, or pattern of methylated sites, or can be or include a decrease in the number, frequency, or pattern of methylated sites. In various instances, a change in methylation status in a change in methylation value.

Methylation value: As used herein, the term "methylation value" refers to a numerical representation of a methylation status, e.g., in the form of number that represents the frequency or ratio of methylation of a methylation locus. In some instances, e.g., as set forth herein, a methylation value can be generated by a method that includes quantifying the amount of intact nucleic acid present in a sample following restriction digestion of the sample with a methylation dependent restriction enzyme. In some instances, e.g., as set forth herein, a methylation value can be generated by a method that includes comparing amplification profiles after bisulfite reaction of a sample. In some instances, e.g., as set forth herein, a methylation value can be generated by comparing sequences of bisulfite-treated and untreated nucleic acids. In some instances, e.g., as set forth herein, a methylation value is, includes, or is based on a quantitative PCR result.

Nucleic acid: As used herein, in its broadest sense, the term "nucleic acid" refers to any compound and/or substance that is or can be incorporated into an oligonucleotide chain. In some embodiments e.g., as set forth herein, a nucleic acid is a compound and/or substance that is or can be incorporated into an oligonucleotide chain via a phosphodiester linkage. As will be clear from context, in some embodiments e.g., as set forth herein, the term nucleic acid refers to an individual nucleic acid residue (e.g., a nucleotide and/or nucleoside), and in some embodiments e.g., as set forth herein refers to an polynucleotide chain comprising a plurality of individual nucleic acid residues. A nucleic acid can be or include DNA, RNA, or a combinations thereof. A nucleic acid can include natural nucleic acid residues, nucleic acid analogs, and/or synthetic residues. In some embodiments e.g., as set forth herein, a nucleic acid includes natural nucleotides (e.g., adenosine, thymidine, guanosine, cytidine, uridine, deoxyadenosine, deoxythymidine, deoxy guanosine, and deoxycytidine). In some embodiments e.g., as set forth herein, a nucleic acid is or includes of one or more nucleotide analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof).

In some embodiments e.g., as set forth herein, a nucleic acid has a nucleotide sequence that encodes a functional gene product such as an RNA or protein. In some embodiments e.g., as set forth herein, a nucleic acid includes one or more introns. In some embodiments e.g., as set forth herein, a nucleic acid includes one or more genes. In some embodiments e.g., as set forth herein, nucleic acids are prepared by one or more of isolation from a natural source, enzymatic synthesis by polymerization based on a complementary template (in vivo or in vitro), reproduction in a recombinant cell or system, and chemical synthesis.

In some embodiments e.g., as set forth herein, a nucleic acid analog differs from a nucleic acid in that it does not utilize a phosphodiester backbone. For example, in some embodiments e.g., as set forth herein, a nucleic acid can include one or more peptide nucleic acids, which are known in the art and have peptide bonds instead of phosphodiester bonds in the backbone. Alternatively or additionally, in some embodiments e.g., as set forth herein, a nucleic acid has one or more phosphorothioate and/or 5'-N-phosphoramidite linkages rather than phosphodiester bonds. In some embodiments e.g., as set forth herein, a nucleic acid comprises one or more modified sugars (e.g., 2'-fluororibose, ribose, 2'-deoxyribose, arabinose, and hexose) as compared with those in natural nucleic acids.

In some embodiments, e.g., as set forth herein, a nucleic acid is or includes at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues. In some embodiments, e.g., as set forth herein, a nucleic acid is partly or wholly single stranded, or partly or wholly double stranded.

Nucleic acid detection assay: As used herein, the term "nucleic acid detection assay" refers to any method of determining the nucleotide composition of a nucleic acid of interest. Nucleic acid detection assays include but are not limited to, DNA sequencing methods, polymerase chain reaction-based methods, probe hybridization methods, ligase chain reaction, etc.

Nucleotide: As used herein, the term "nucleotide" refers to a structural component, or building block, of polynucleotides, e.g., of DNA and/or RNA polymers. A nucleotide includes of a base (e.g., adenine, thymine, uracil, guanine, or cytosine) and a molecule of sugar and at least one phosphate group. As used herein, a nucleotide can be a methylated nucleotide or an un-methylated nucleotide. Those of skill in the art will appreciate that nucleic acid terminology, such as, as examples, "locus" or "nucleotide" can refer to both a locus or nucleotide of a single nucleic acid molecule and/or to the cumulative population of loci or nucleotides within a plurality of nucleic acids (e.g., a plurality of nucleic acids in a sample and/or representative of a subject) that are representative of the locus or nucleotide (e.g., having the same identical nucleic acid sequence and/or nucleic acid sequence context, or having a substantially identical nucleic acid sequence and/or nucleic acid context).

Oligonucleotide primer: As used herein, the term oligonucleotide primer, or primer, refers to a nucleic acid molecule used, capable of being used, or for use in, generating amplicons from a template nucleic acid molecule. Under transcription-permissive conditions (e.g., in the presence of nucleotides and a DNA polymerase, and at a suitable temperature and pH), an oligonucleotide primer can provide a point of initiation of transcription from a template to which the oligonucleotide primer hybridizes. Typically, an oligonucleotide primer is a single-stranded nucleic acid between 5 and 200 nucleotides in length. Those of skill in the art will appreciate that optimal primer length for generating amplicons from a template nucleic acid molecule can vary with conditions including temperature parameters, primer composition, and transcription or amplification method. A pair of oligonucleotide primers, as used herein, refers to a set of two oligonucleotide primers that are respectively complementary to a first strand and a second strand of a template double-stranded nucleic acid molecule. First and second members of a pair of oligonucleotide primers may be referred to as a "forward" oligonucleotide primer and a "reverse" oligonucleotide primer, respectively, with respect to a template nucleic acid strand, in that the forward oligonucleotide primer is capable of hybridizing with a nucleic acid strand complementary to the template nucleic acid strand, the reverse oligonucleotide primer is capable of hybridizing with the template nucleic acid strand, and the position of the forward oligonucleotide primer with respect to the template nucleic acid strand is 5' of the position of the reverse oligonucleotide primer sequence with respect to the template nucleic acid strand. It will be understood by those of skill in the art that the identification of a first and second oligonucleotide primer as forward and reverse oligonucleotide primers, respectively, is arbitrary inasmuch as these identifiers depend upon whether a given nucleic acid strand or its complement is utilized as a template nucleic acid molecule.

Overlapping: The term "overlapping" is used herein in reference to two regions of DNA, each of which contains a sub-sequence that is substantially identical to a sub-sequence of the same length in the other region (e.g., the two regions of DNA have a common sub-sequence). "Substantially identical" means that the two identically-long sub-sequences differ by fewer than a given number of base pairs. In certain instances, e.g., as set forth herein, each sub-sequence has a length of at least 20 base pairs that differ by fewer than 4, 3, 2, or 1 base pairs from each other (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 24 base pairs that differ by fewer than 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 50 base pairs that differ by fewer than 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 100 base pairs that differ by fewer than 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 200 base pairs that differ by fewer than 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 250 base pairs that differ by fewer than 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99/6 similarity, or at least 99.5% similarity). In certain instances, e.g., as set forth herein, each sub-sequence has a length of at least 300 base pairs that differ by fewer than 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 500 base pairs that differ by fewer than 100, 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, each sub-sequence has a length of at least 1000 base pairs that differ by fewer than 200, 100, 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances, e.g., as set forth herein, the subsequence of a first region of the two regions of DNA may comprise the entirety of the second region of the two regions of DNA (or vice versa) (e.g., the common sub-sequence may contain the whole of either or both regions). In certain embodiments, where a methylation locus has a sequence that comprises at least a portion of a DMR sequence listed herein (e.g., at least 20%, at least 30%, at least 40%, at least 50%, at least 60%, at least 70%, at least 80%, or at least 90% of the DMR sequence), the overlapping portion of the methylation locus has at least 95% similarity, at least 98% similarity, or at least 99% similarity with the overlapping portion of the DMR sequence (e.g., if the overlapping portion is 100 bp, the portion of the methylation locus that overlaps with the portion of the DMR differs by no more than 1 bp, no more than 2 bp, or no more than 5 bp). In certain embodiments, where a methylation locus has a sequence that comprises "at least a portion of" a DMR sequence listed herein, this means the methylation locus has a subsequence in common with the DMR sequence that has a consecutive series of bases that covers at least 20%, at least 30%, at least 40%, at least 50%, at least 60%, at least 70%, at least 80%, or at least 90% of the DMR sequence, e.g., wherein the subsequence in common differs by no more than 1 bp, no more than 2 bp, or no more than 5 bp). In certain embodiments, where a methylation locus has a sequence that comprises "at least a portion of" a DMR sequence listed herein, this means the methylation locus contains at least a portion of (e.g., at least 20%, at least 30%, at least 40%, at least 50%, at least 60%, at least 70%, at least 80%, or at least 90% of) the CpG dinucleotides corresponding to the CpG dinucleotides within the DMR sequence.

Pharmaceutical composition: As used herein, the term "pharmaceutical composition" refers to a composition in which an active agent is formulated together with one or more pharmaceutically acceptable carriers. In some embodiments, e.g., as set forth herein, the active agent is present in a unit dose amount appropriate for administration to a subject, e.g., in a therapeutic regimen that shows a statistically significant probability of achieving a predetermined therapeutic effect when administered to a relevant population. In some embodiments, e.g., as set forth herein, a pharmaceutical composition can be formulated for administration in a particular form (e.g., in a solid form or a liquid form), and/or can be specifically adapted for, for example: oral administration (for example, as a drenche (aqueous or non-aqueous solutions or suspensions), tablet, capsule, bolus, powder, granule, paste, etc., which can be formulated specifically for example for buccal, sublingual, or systemic absorption); parenteral administration (for example, by subcutaneous, intramuscular, intravenous or epidural injection as, for example, a sterile solution or suspension, or sustained-release formulation, etc.); topical application (for example, as a cream, ointment, patch or spray applied for example to skin, lungs, or oral cavity); intravaginal or intrarectal administration (for example, as a pessary, suppository, cream, or foam); ocular administration; nasal or pulmonary administration, etc.

Pharmaceutically acceptable: As used herein, the term "pharmaceutically acceptable," as applied to one or more, or all, component(s) for formulation of a composition as disclosed herein, means that each component must be compatible with the other ingredients of the composition and not deleterious to the recipient thereof.

Pharmaceutically acceptable carrier: As used herein, the term "pharmaceutically acceptable carrier" refers to a pharmaceutically-acceptable material, composition, or vehicle, such as a liquid or solid filler, diluent, excipient, or solvent encapsulating material, that facilitates formulation and/or modifies bioavailability of an agent, e.g., a pharmaceutical agent. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Polyposis syndromes: The terms "polyposis" and "polyposis syndrome", as used herein, refer to hereditary conditions that include, but are not limited to, familial adenomatous polyposis (FAP), hereditary nonpolyposis colorectal cancer (HNPCC)/Lynch syndrome, Gardner syndrome, Turcot syndrome, MUTYH polyposis, Peutz-Jeghers syndrome, Cowden disease, familial juvenile polyposis, and hyperplastic polyposis. In certain embodiments, polyposis includes serrated polyposis syndrome. Serrated polyposis is classified by a subject having 5 or more serrated polyps proximal to the sigmoid colon with two or more at least 10 mm in size, having a serrated polyp proximal to the sigmoid colon in the context of a family history of serrated polyposis, and/or having 20 or more serrated polyps throughout the colon.

Prevent or prevention: The terms "prevent" and "prevention," as used herein in connection with the occurrence of a disease, disorder, or condition, refers to reducing the risk of developing the disease, disorder, or condition; delaying onset of the disease, disorder, or condition; delaying onset of one or more characteristics or symptoms of the disease, disorder, or condition; and/or to reducing the frequency and/or severity of one or more characteristics or symptoms of the disease, disorder, or condition. Prevention can refer to prevention in a particular subject or to a statistical impact on a population of subjects. Prevention can be considered complete when onset of a disease, disorder, or condition has been delayed for a predefined period of time.

Probe: As used herein, the term "probe" refers to a single- or double-stranded nucleic acid molecule that is capable of hybridizing with a complementary target and includes a detectable moiety. In certain embodiments, e.g., as set forth herein, a probe is a restriction digest product or is a synthetically produced nucleic acid, e.g., a nucleic acid produced by recombination or amplification. In some instances, e.g., as set forth herein, a probe is a capture probe useful in detection, identification, and/or isolation of a target sequence, such as a gene sequence. In various instances, e.g., as set forth herein, a detectable moiety of probe can be, e.g., an enzyme (e.g., ELISA, as well as enzyme-based histochemical assays), fluorescent moiety, radioactive moiety, or moiety associated with a luminescence signal.

Prognosis: As used herein, the term "prognosis" refers to determining the qualitative of quantitative probability of at least one possible future outcome or event. As used herein, a prognosis can be a determination of the likely course of a disease, disorder, or condition such as cancer in a subject, a determination regarding the life expectancy of a subject, or a determination regarding response to therapy, e.g., to a particular therapy.

Prognostic information: As used herein, the term "prognostic information" refers to information useful in providing a prognosis. Prognostic information can include, without limitation, biomarker status information.

Promoter: As used herein, a "promoter" can refer to a DNA regulatory region that directly or indirectly (e.g., through promoter-bound proteins or substances) associates with an RNA polymerase and participates in initiation of transcription of a coding sequence.

Reference: As used herein describes a standard or control relative to which a comparison is performed. For example, in some embodiments, e.g., as set forth herein, an agent, subject, animal, individual, population, sample, sequence, or value of interest is compared with a reference or control agent, subject, animal, individual, population, sample, sequence, or value. In some embodiments, e.g., as set forth herein, a reference or characteristic thereof is tested and/or determined substantially simultaneously with the testing or determination of the characteristic in a sample of interest. In some embodiments, e.g., as set forth herein, a reference is a historical reference, optionally embodied in a tangible medium. Typically, as would be understood by those of skill in the art, a reference is determined or characterized under comparable conditions or circumstances to those under assessment, e.g., with regard to a sample. Those skilled in the art will appreciate when sufficient similarities are present to justify reliance on and/or comparison to a particular possible reference or control.

Risk: As used herein with respect to a disease, disorder, or condition, the term "risk" refers to the qualitative of quantitative probability (whether expressed as a percentage or otherwise) that a particular individual will develop the disease, disorder, or condition. In some embodiments, e.g., as set forth herein, risk is expressed as a percentage. In some embodiments, e.g., as set forth herein, a risk is a qualitative of quantitative probability that is equal to or greater than 0, 1, 2, 3, 4, 5, 6, 7, 8, 9, 10, 20, 30, 40, 50, 60, 70, 80, 90, or 100%. In some embodiments, e.g., as set forth herein, risk is expressed as a qualitative or quantitative level of risk relative to a reference risk or level or the risk of the same outcome attributed to a reference. In some embodiments, e.g., as set forth herein, relative risk is increased or decreased in comparison to the reference sample by a factor of 1.1, 1.2, 1.3, 1.4, 1.5, 1.6, 1.7, 1.8, 1.9, 2, 3, 4, 5, 6, 7, 8, 9, 10, or more.

Sample: As used herein, the term "sample" typically refers to an aliquot of material obtained or derived from a source of interest. In some embodiments, e.g., as set forth herein, a source of interest is a biological or environmental source. In some embodiments, e.g., as set forth herein, a sample is a "primary sample" obtained directly from a source of interest. In some embodiments, e.g., as set forth herein, as will be clear from context, the term "sample" refers to a preparation that is obtained by processing of a primary sample (e.g., by removing one or more components of and/or by adding one or more agents to a primary sample). Such a "processed sample" can include, for example cells, nucleic acids, or proteins extracted from a sample or obtained by subjecting a primary sample to techniques such as amplification or reverse transcription of nucleic acids, isolation and/or purification of certain components, etc.

In certain instances, e.g., as set forth herein, a processed sample can be a DNA sample that has been amplified (e.g., pre-amplified). Thus, in various instances, e.g., as set forth herein, an identified sample can refer to a primary form of the sample or to a processed form of the sample. In some instances, e.g., as set forth herein, a sample that is enzyme-digested DNA can refer to primary enzyme-digested DNA (the immediate product of enzyme digestion) or a further processed sample such as enzyme-digested DNA that has been subject to an amplification step (e.g., an intermediate amplification step, e.g., pre-amplification) and/or to a filtering step, purification step, or step that modifies the sample to facilitate a further step, e.g., in a process of determining methylation status (e.g., methylation status of a primary sample of DNA and/or of DNA as it existed in its original source context).

Screening: As used herein, the term "screening" refers to any method, technique, process, or undertaking intended to generate diagnostic information and/or prognostic information. Accordingly, those of skill in the art will appreciate that the term screening encompasses method, technique, process, or undertaking that determines whether an individual has, is likely to have or develop, or is at risk of having or developing a disease, disorder, or condition, e.g., colorectal cancer.

Specificity: As used herein, the "specificity" of a biomarker refers to the percentage of samples that are characterized by absence of the event or state of interest for which measurement of the biomarker accurately indicates absence of the event or state of interest (true negative rate). In various embodiments, e.g., as set forth herein, characterization of the negative samples is independent of the biomarker, and can be achieved by any relevant measure, e.g., any relevant measure known to those of skill in the art. Thus, specificity reflects the probability that the biomarker would detect the absence of the event or state of interest when measured in a sample not characterized that event or state of interest. In particular embodiments in which the event or state of interest is colorectal cancer, e.g., as set forth herein, specificity refers to the probability that a biomarker would detect the absence of colorectal cancer in a subject lacking colorectal cancer. Lack of colorectal cancer can be determined, e.g., by histology.

Sensitivity: As used herein, the "sensitivity" of a biomarker refers to the percentage of samples that are characterized by the presence of the event or state of interest for which measurement of the biomarker accurately indicates presence of the event or state of interest (true positive rate). In various embodiments, e.g., as set forth herein, characterization of the positive samples is independent of the biomarker, and can be achieved by any relevant measure, e.g., any relevant measure known to those of skill in the art. Thus, sensitivity reflects the probability that a biomarker would detect the presence of the event or state of interest when measured in a sample characterized by presence of that event or state of interest. In particular embodiments in which the event or state of interest is colorectal cancer, e.g., as set forth herein, sensitivity refers to the probability that a biomarker would detect the presence of colorectal cancer in a subject that has colorectal cancer. Presence of colorectal cancer can be determined, e.g., by histology.

Solid Tumor: As used herein, the term "solid tumor" refers to an abnormal mass of tissue including cancer cells. In various embodiments, e.g., as set forth herein, a solid tumor is or includes an abnormal mass of tissue that does not contain cysts or liquid areas. In some embodiments, e.g., as set forth herein, a solid tumor can be benign; in some embodiments, a solid tumor can be malignant. Examples of solid tumors include carcinomas, lymphomas, and sarcomas. In some embodiments, e.g., as set forth herein, solid tumors can be or include adrenal, bile duct, bladder, bone, brain, breast, cervix, colon, endometrium, esophagum, eye, gall bladder, gastrointestinal tract, kidney, larynx, liver, lung, nasal cavity, nasopharynx, oral cavity, ovary, penis, pituitary, prostate, retina, salivary gland, skin, small intestine, stomach, testis, thymus, thyroid, uterine, vaginal, and/or vulval tumors.

Stage of cancer: As used herein, the term "stage of cancer" refers to a qualitative or quantitative assessment of the level of advancement of a cancer. In some embodiments, e.g., as set forth herein, criteria used to determine the stage of a cancer can include, but are not limited to, one or more of where the cancer is located in a body, tumor size, whether the cancer has spread to lymph nodes, whether the cancer has spread to one or more different parts of the body, etc. In some embodiments, e.g., as set forth herein, cancer can be staged using the so-called TNM System, according to which T refers to the size and extent of the main tumor, usually called the primary tumor; N refers to the number of nearby lymph nodes that have cancer; and M refers to whether the cancer has metastasized. In some embodiments, e.g., as set forth herein, a cancer can be referred to as Stage 0 (abnormal cells are present but have not spread to nearby tissue, also called carcinoma in situ, or CIS; CIS is not cancer, but it can become cancer), Stage I-Ill (cancer is present; the higher the number, the larger the tumor and the more it has spread into nearby tissues), or Stage IV (the cancer has spread to distant parts of the body). In some embodiments, e.g., as set forth herein, a cancer can be assigned to a stage selected from the group consisting of: in situ (abnormal cells are present but have not spread to nearby tissue); localized (cancer is limited to the place where it started, with no sign that it has spread); regional (cancer has spread to nearby lymph nodes, tissues, or organs): distant (cancer has spread to distant parts of the body); and unknown (there is not enough information to identify cancer stage).

Susceptible to: An individual who is "susceptible to" a disease, disorder, or condition is at risk for developing the disease, disorder, or condition. In some embodiments, e.g., as set forth herein, an individual who is susceptible to a disease, disorder, or condition does not display any symptoms of the disease, disorder, or condition. In some embodiments, e.g., as set forth herein, an individual who is susceptible to a disease, disorder, or condition has not been diagnosed with the disease, disorder, and/or condition. In some embodiments, e.g., as set forth herein, an individual who is susceptible to a disease, disorder, or condition is an individual who has been exposed to conditions associated with, or presents a biomarker status (e.g., a methylation status) associated with, development of the disease, disorder, or condition. In some embodiments, e.g., as set forth herein, a risk of developing a disease, disorder, and/or condition is a population-based risk (e.g., family members of individuals suffering from the disease, disorder, or condition).

Subject: As used herein, the term "subject" refers to an organism, typically a mammal (e.g., a human). In some embodiments, e.g., as set forth herein, a subject is suffering from a disease, disorder or condition. In some embodiments, e.g., as set forth herein, a subject is susceptible to a disease, disorder, or condition. In some embodiments, e.g., as set forth herein, a subject displays one or more symptoms or characteristics of a disease, disorder or condition. In some embodiments, e.g., as set forth herein, a subject is not suffering from a disease, disorder or condition. In some embodiments, e.g., as set forth herein, a subject does not display any symptom or characteristic of a disease, disorder, or condition. In some embodiments, e.g., as set forth herein, a subject is someone with one or more features characteristic of susceptibility to or risk of a disease, disorder, or condition. In some embodiments, e.g., as set forth herein, a subject is a patient. In some embodiments, e.g., as set forth herein, a subject is an individual to whom diagnosis has been performed and/or to whom therapy has been administered. In some instances, e.g., as set forth herein, a human subject can be interchangeably referred to as an "individual."

Therapeutic agent: As used herein, the term "therapeutic agent" refers to any agent that elicits a desired pharmacological effect when administered to a subject. In some embodiments, e.g., as set forth herein, an agent is considered to be a therapeutic agent if it demonstrates a statistically significant effect across an appropriate population. In some embodiments, e.g., as set forth herein, the appropriate population can be a population of model organisms or a human population. In some embodiments, e.g., as set forth herein, an appropriate population can be defined by various criteria, such as a certain age group, gender, genetic background, preexisting clinical conditions, etc. In some embodiments, e.g., as set forth herein, a therapeutic agent is a substance that can be used for treatment of a disease, disorder, or condition. In some embodiments, e.g., as set forth herein, a therapeutic agent is an agent that has been or is required to be approved by a government agency before it can be marketed for administration to humans. In some embodiments, e.g., as set forth herein, a therapeutic agent is an agent for which a medical prescription is required for administration to humans.

Therapeutically effective amount: As used herein, the term "therapeutically effective amount" refers to an amount that produces a desired effect for which it is administered. In some embodiments, e.g., as set forth herein, the term refers to an amount that is sufficient, when administered to a population suffering from or susceptible to a disease, disorder, or condition, in accordance with a therapeutic dosing regimen, to treat the disease, disorder, or condition. Those of ordinary skill in the art will appreciate that the term therapeutically effective amount does not in fact require successful treatment be achieved in a particular individual. Rather, a therapeutically effective amount can be an amount that provides a particular desired pharmacological response in a significant number of subjects when administered to individuals in need of such treatment. In some embodiments, e.g., as set forth herein, reference to a therapeutically effective amount can be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent can be formulated and/or administered in a single dose. In some embodiments, e.g., as set forth herein, a therapeutically effective agent can be formulated and/or administered in a plurality of doses, for example, as part of a multi-dose dosing regimen.

Treatment: As used herein, the term "treatment" (also "treat" or "treating") refers to administration of a therapy that partially or completely alleviates, ameliorates, relieves, inhibits, delays onset of, reduces severity of, and/or reduces incidence of one or more symptoms, features, and/or causes of a particular disease, disorder, or condition, or is administered for the purpose of achieving any such result. In some embodiments, e.g., as set forth herein, such treatment can be of a subject who does not exhibit signs of the relevant disease, disorder, or condition and/or of a subject who exhibits only early signs of the disease, disorder, or condition. Alternatively or additionally, such treatment can be of a subject who exhibits one or more established signs of the relevant disease, disorder and/or condition. In some embodiments, e.g., as set forth herein, treatment can be of a subject who has been diagnosed as suffering from the relevant disease, disorder, and/or condition. In some embodiments, e.g., as set forth herein, treatment can be of a subject known to have one or more susceptibility factors that are statistically correlated with increased risk of development of the relevant disease, disorder, or condition. In various examples, treatment is of a cancer.

Upstream: As used herein, the term "upstream" means a first DNA region is closer, relative to a second DNA region, to the N-terminus of a nucleic acid that includes the first DNA region and the second DNA region.

Unit dose: As used herein, the term "unit dose" refers to an amount administered as a single dose and/or in a physically discrete unit of a pharmaceutical composition. In many embodiments, e.g., as set forth herein, a unit dose contains a predetermined quantity of an active agent. In some embodiments, e.g., as set forth herein, a unit dose contains an entire single dose of the agent. In some embodiments, e.g., as set forth herein, more than one unit dose is administered to achieve a total single dose. In some embodiments, e.g., as set forth herein, administration of multiple unit doses is required, or expected to be required, in order to achieve an intended effect. A unit dose can be, for example, a volume of liquid (e.g., an acceptable carrier) containing a predetermined quantity of one or more therapeutic moieties, a predetermined amount of one or more therapeutic moieties in solid form, a sustained release formulation or drug delivery device containing a predetermined amount of one or more therapeutic moieties, etc. It will be appreciated that a unit dose can be present in a formulation that includes any of a variety of components in addition to the therapeutic agent(s). For example, acceptable carriers (e.g., pharmaceutically acceptable carriers), diluents, stabilizers, buffers, preservatives, etc., can be included. It will be appreciated by those skilled in the art, in many embodiments, e.g., as set forth herein, a total appropriate daily dosage of a particular therapeutic agent can comprise a portion, or a plurality, of unit doses, and can be decided, for example, by a medical practitioner within the scope of sound medical judgment. In some embodiments, e.g., as set forth herein, the specific effective dose level for any particular subject or organism can depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Unmethylated: As used herein, the terms "unmethylated" and "non-methylated" are used interchangeable and mean that an identified DNA region includes no methylated nucleotides.

Variant: As used herein, the term "variant" refers to an entity that shows significant structural identity with a reference entity but differs structurally from the reference entity in the presence, absence, or level of one or more chemical moieties as compared with the reference entity. In some embodiments, e.g., as set forth herein, a variant also differs functionally from its reference entity. In general, whether a particular entity is properly considered to be a "variant" of a reference entity is based on its degree of structural identity with the reference entity. A variant can be a molecule comparable, but not identical to, a reference. For example, a variant nucleic acid can differ from a reference nucleic acid at one or more differences in nucleotide sequence. In some embodiments, e.g., as set forth herein, a variant nucleic acid shows an overall sequence identity with a reference nucleic acid that is at least 85%, 86%, 87%, 88%, 89%, 90%, 91%, 92%, 93%, 94%, 95%, 96%, 97%, or 99%. In many embodiments, e.g., as set forth herein, a nucleic acid of interest is considered to be a "variant" of a reference nucleic acid if the nucleic acid of interest has a sequence that is identical to that of the reference but for a small number of sequence alterations at particular positions. In some embodiments, e.g., as set forth herein, a variant has 10, 9, 8, 7, 6, 5, 4, 3, 2, or 1 substituted residues as compared with a reference. In some embodiments, e.g., as set forth herein, a variant has not more than 5, 4, 3, 2, or 1 residue additions, substitutions, or deletions as compared with the reference. In various embodiments, e.g., as set forth herein, the number of additions, substitutions, or deletions is fewer than about 25, about 20, about 19, about 18, about 17, about 16, about 15, about 14, about 13, about 10, about 9, about 8, about 7, about 6, and commonly are fewer than about 5, about 4, about 3, or about 2 residues.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which.

DETAILED DESCRIPTION

Figure 1A:
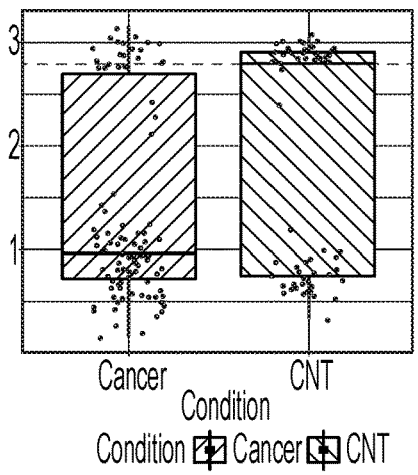
FIGS. 1A-DD show detection of methylated markers in plasma. dCt values are plotted for 30 markers for control samples (CNT) and cancer (colorectal, breast, lung, pancreatic) samples (Cancer).
Figure 1B:
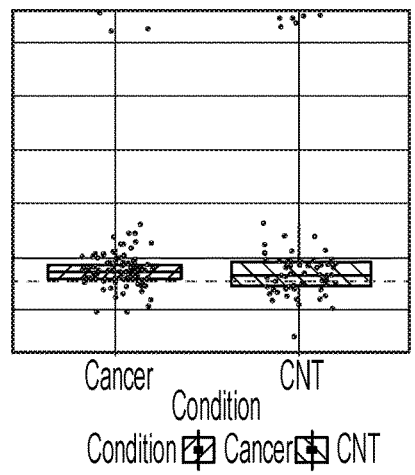
Figure 1C:
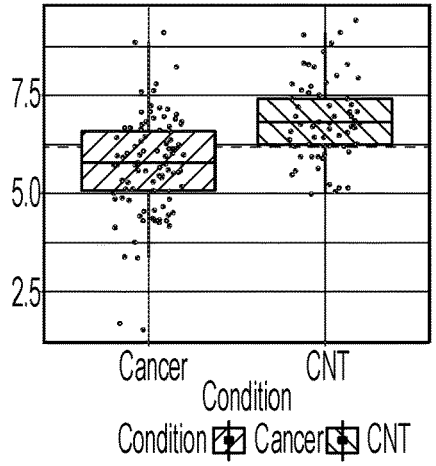
Figure 1D:
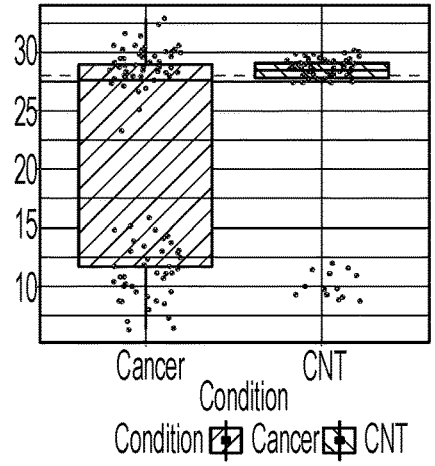
Figure 1E:
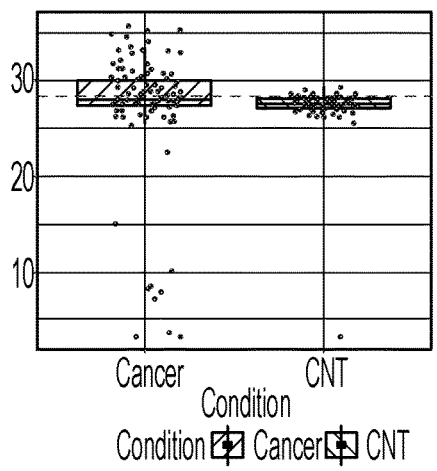
Figure 1F:
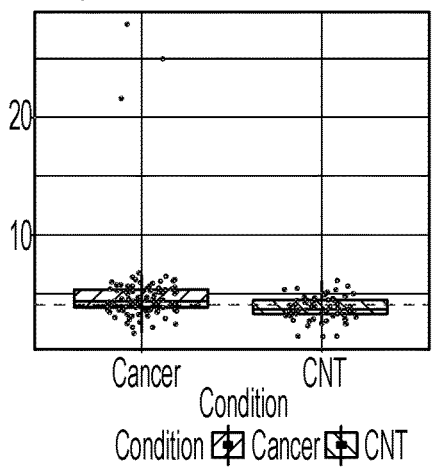
Figure 1G:
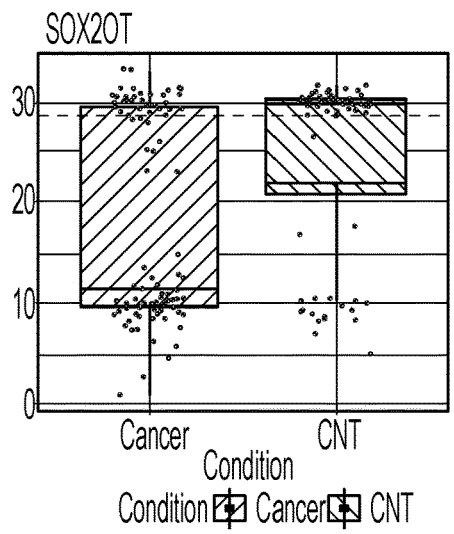
Figure 1H:
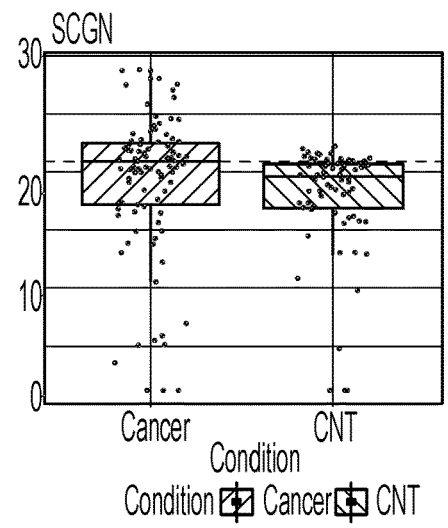
Figure 1I:
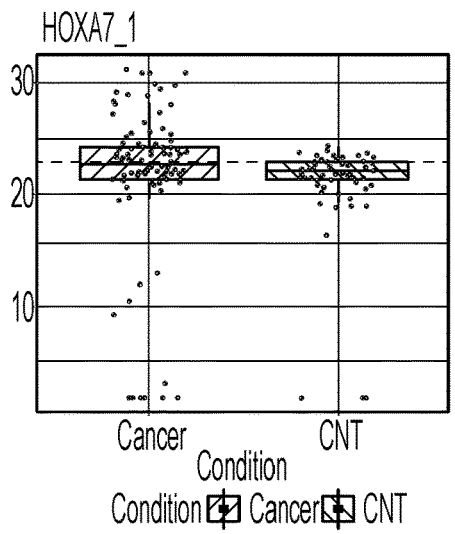
Figure 1J:
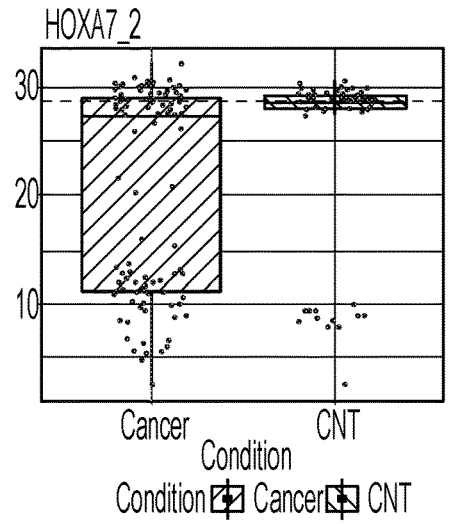
Figure 1K:
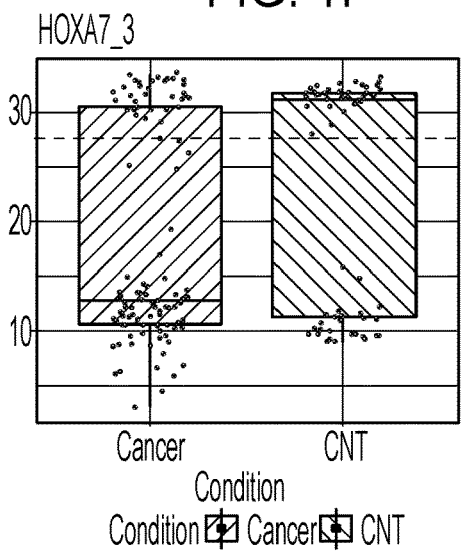
Figure 1L:
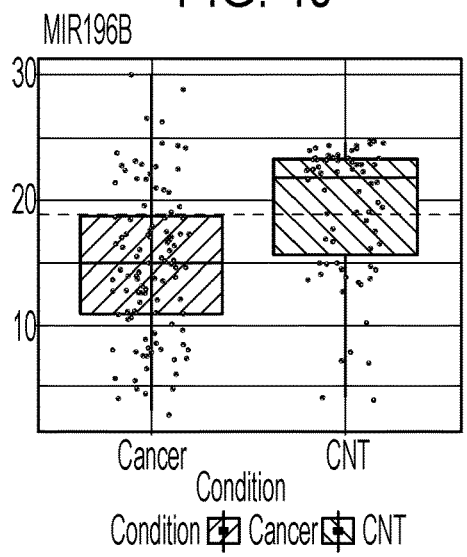
Figure 1M:
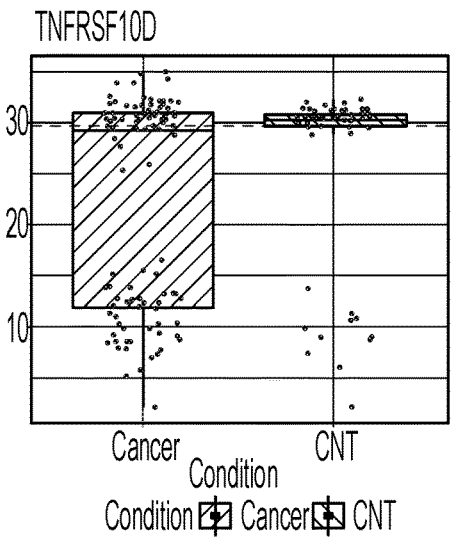
Figure 1N:
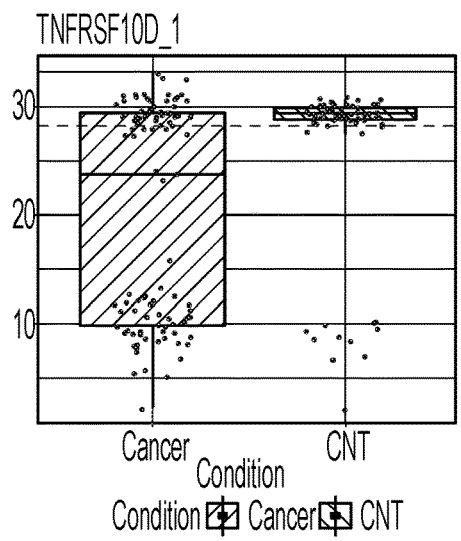
Figure 1O:
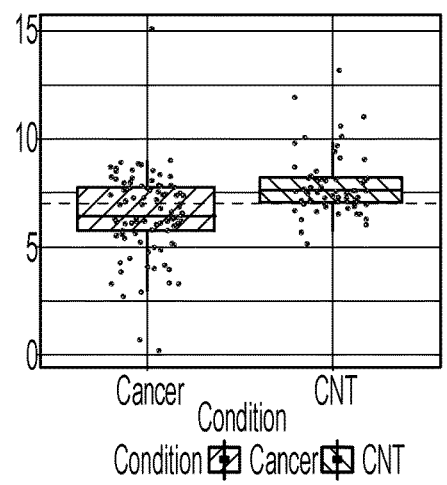
Figure 1P:
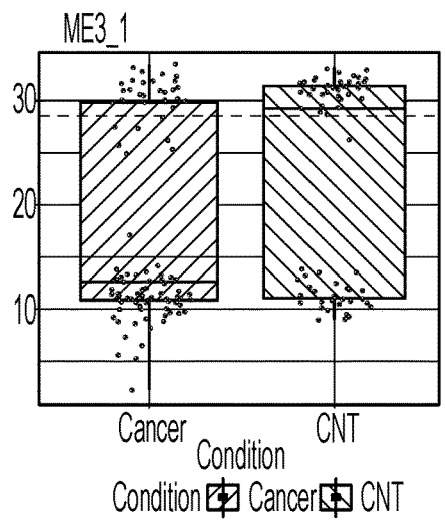
Figure 1Q:
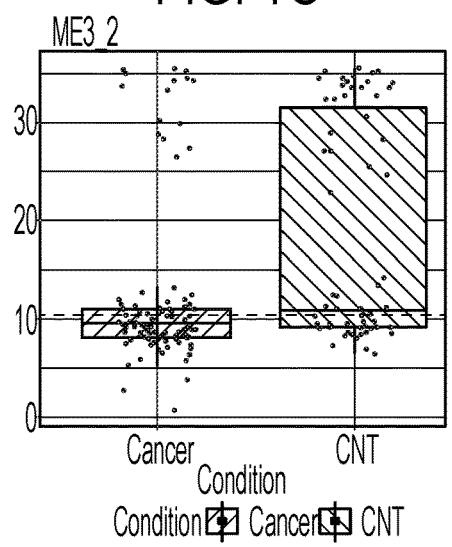
Figure 1R:
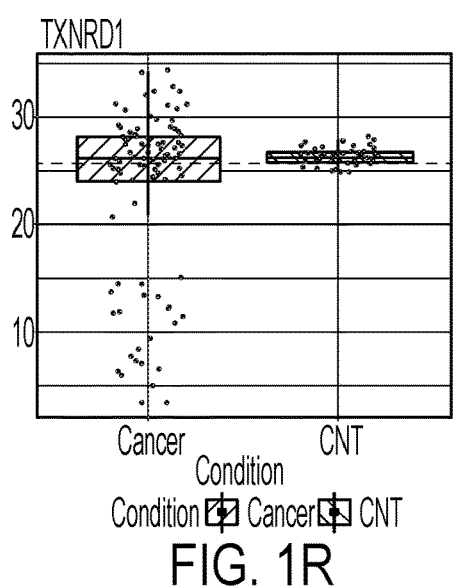
Figure 1S:
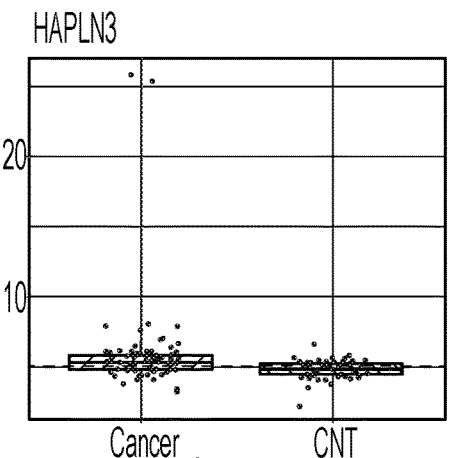
Figure 1T:
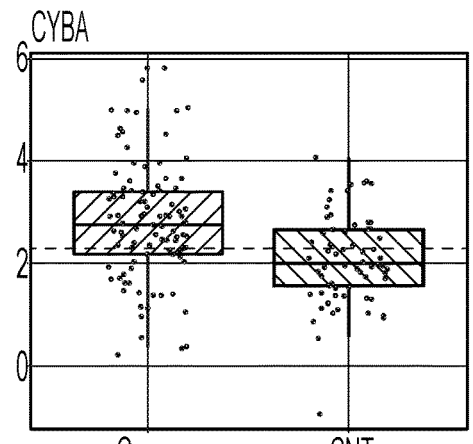
Figure 1U:
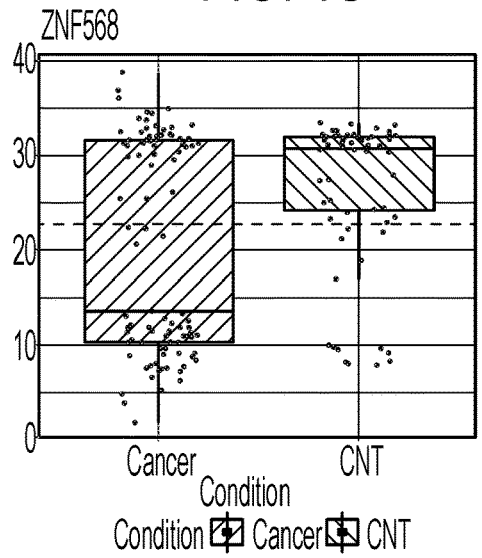
Figure 1V:
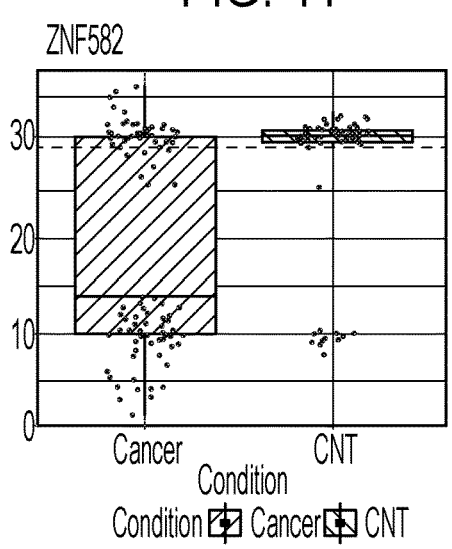
Figure 1W:
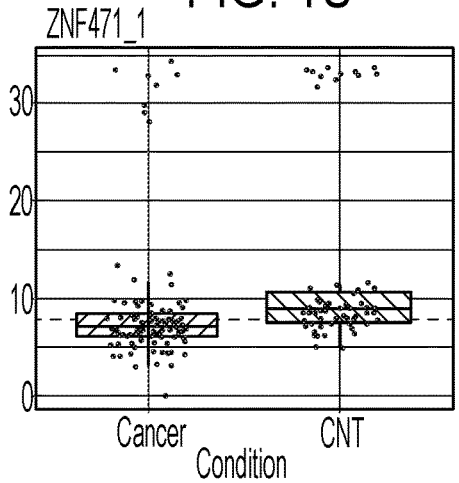
Figure 1X:
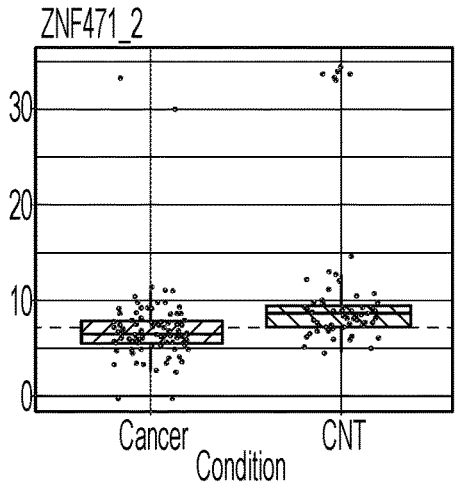
Figure 1Y:
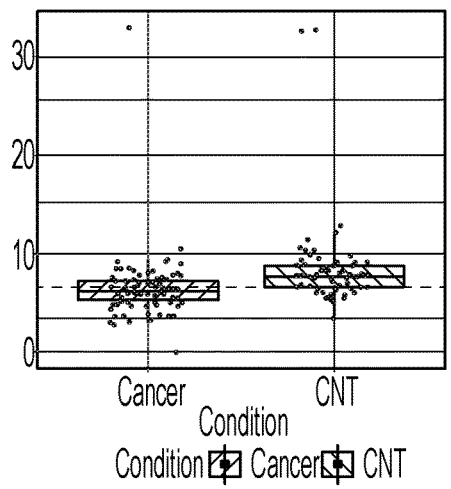
Figure 1Z:
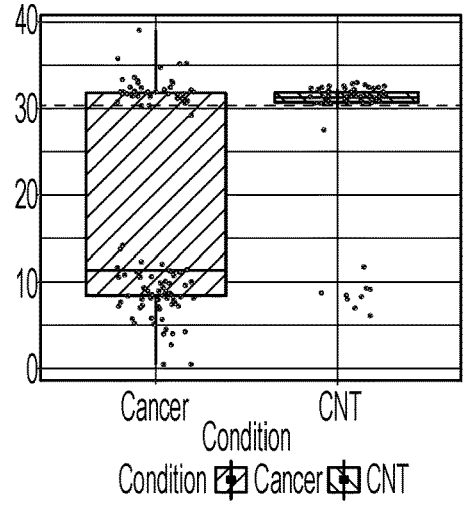
Figure 1A:
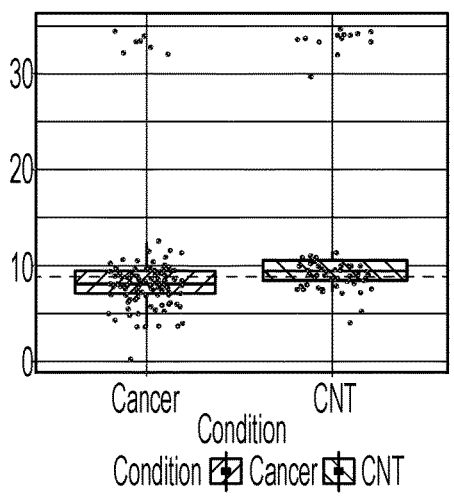
Figure 1B:
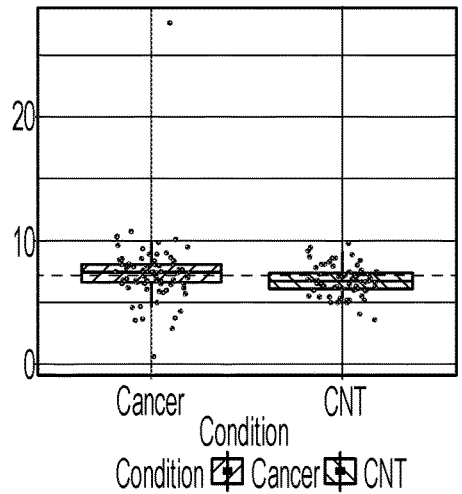
Figure 1C:
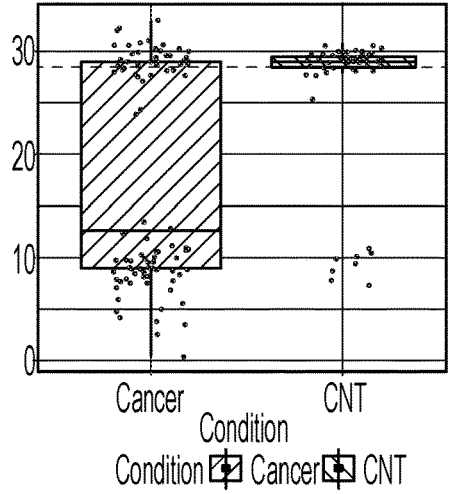
Figure 1D:
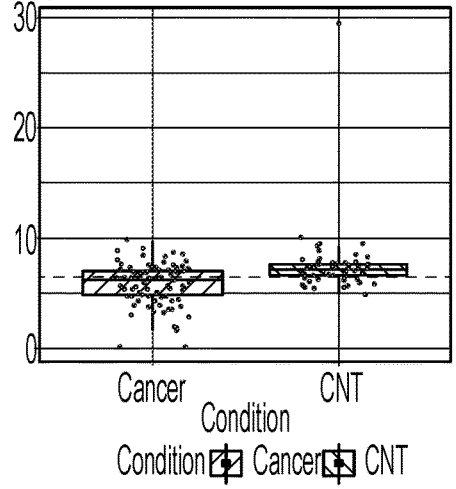

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

Screening for Multiple Cancer Types

There is a need for improved methods of detecting (e.g., screening for) colorectal cancer, breast cancer, lung cancer and/or pancreatic cancer. This includes a need for screening for early-stage cancer. Colorectal cancer, breast cancer, lung cancer and/or pancreatic cancer screening programs are often ineffective or unsatisfactory. Improved screens for colorectal cancer, breast cancer, lung cancer and/or pancreatic cancer improves diagnosis and reduces colorectal cancer, breast cancer, lung cancer and/or pancreatic cancer mortality.

DNA methylation (e.g., hypermethylation or hypomethylation) can activate or inactivate genes, including genes that impact development of colorectal cancer, breast cancer, lung cancer and/or pancreatic cancer. Thus, for example, hypermethylation can inactivate one or more genes that typically act to suppress cancer, causing or contributing to development of cancer in a sample or subject.

The present disclosure includes the discovery that determination of the methylation status of one or more methylation loci provided herein, and/or the methylation status of one or more DMRs provided herein, provides for detection of (e.g., screening for) colorectal cancer, breast cancer, lung cancer and/or pancreatic cancer. In certain embodiments, screening can classify a subject as having or not having one or more of colorectal cancer, breast cancer, lung cancer and/or pancreatic cancer with a high degree of sensitivity and/or specificity. The present disclosure provides compositions and methods including or relating to colorectal cancer, breast cancer, lung cancer and/or pancreatic cancer methylation biomarkers that, individually or in various panels comprising two or more methylation biomarkers, provide for screening of colorectal cancer, breast cancer, lung cancer and/or pancreatic cancer.

In various embodiments, a methylation biomarker of the present disclosure used for detection of colorectal cancer, breast cancer, lung cancer and/or pancreatic cancer is selected from a methylation locus that is or includes at least a portion of a DMR listed in Tables 1-4, 7-11 13 and 15. Tables 1-4, 7-11 13 and 15 list the region of DNA on which the DMR is found, which includes the chromosome number (chr), the start and end positions of the DMR on the chromosome, and genes (if any) that are known to be associated with the region. If no genes are currently known to be associated with the region, the term "NA" is listed in the Genes column.

TABLE 1

List of DMRs found to have significantly altered methylation pattern(s) in the blood and/or tissue of colorectal cancer, breast cancer, lung cancer and/or pancreatic cancer patients compared to controls.

| Gene | chr | start | end | width | genome |
|---|---|---|---|---|---|
| HOXA7 | 7 | 27155916 | 27156027 | 112 | hg38 |
| MIR196B | 7 | 27169630 | 27169719 | 90 | hg38 |
| TNFRSF10D | 8 | 23163995 | 23164099 | 105 | hg38 |
| DNM3 | 1 | 171841774 | 171841857 | 84 | hg38 |
| C1orf230 | 1 | 151721583 | 151721679 | 97 | hg38 |
| ZNF568 | 19 | 36916252 | 36916371 | 120 | hg38 |
| C9orf50 | 9 | 129620787 | 129620870 | 84 | hg38 |
| NA | 5 | 73436635 | 73436710 | 76 | hg38 |
| DLX6AS | 7 | 97014186 | 97014266 | 81 | hg38 |
| DIO3;MIR1247 | 14 | 101561395 | 101561505 | 111 | hg38 |
| GSG1L | 16 | 28063861 | 28063964 | 104 | hg38 |
| LONRF2 | 2 | 100322387 | 100322463 | 77 | hg38 |
| PCDH9 | 13 | 67231171 | 67231265 | 95 | hg38 |
| GFPT2 | 5 | 180353729 | 180353815 | 87 | hg38 |

TABLE 2

List of DMRs found to have significantly altered methylation pattern allowing for distinguishing between colorectal cancer, breast cancer, lung cancer and pancreatic cancer patients

| Gene | chr | start | end | width | genome |
|---|---|---|---|---|---|
| MAST1 | 19 | 12867716 | 12867820 | 105 | hg38 |
| KLK10 | 19 | 51019613 | 51019705 | 93 | hg38 |
| HOXD8 | 2 | 176129896 | 176130001 | 106 | hg38 |
| C2orf88 | 2 | 190180554 | 190180682 | 129 | hg38 |
| PREX1 | 20 | 48828337 | 48828448 | 112 | hg38 |
| AMOTL2 | 3 | 134364403 | 134364512 | 110 | hg38 |
| SOX2OT | 3 | 181719490 | 181719596 | 107 | hg38 |
| SCGN | 6 | 25652114 | 25652232 | 119 | hg38 |
| HOXA7 | 7 | 27155916 | 27156027 | 112 | hg38 |
| HOXA7 | 7 | 27156273 | 27156352 | 80 | hg38 |
| HOXA7 | 7 | 27156291 | 27156403 | 113 | hg38 |
| MIR196B | 7 | 27169630 | 27169719 | 90 | hg38 |
| TNFRSF10D | 8 | 23163949 | 23164031 | 83 | hg38 |
| TNFRSF10D | 8 | 23163995 | 23164099 | 105 | hg38 |
| NA | 10 | 100830555 | 100830658 | 104 | hg38 |
| ME3 | 11 | 86672189 | 86672296 | 108 | hg38 |
| ME3 | 11 | 86672338 | 86672429 | 92 | hg38 |
| TXNRD1 | 12 | 104215675 | 104215784 | 110 | hg38 |
| HAPLN3 | 15 | 88895676 | 88895781 | 106 | hg38 |
| CYBA | 16 | 88651139 | 88651205 | 67 | hg38 |
| ZNF568 | 19 | 36916284 | 36916453 | 170 | hg38 |
| ZNF582 | 19 | 56393606 | 56393725 | 120 | hg38 |
| ZNF471 | 19 | 56507527 | 56507675 | 149 | hg38 |
| ZNF471 | 19 | 56507558 | 56507675 | 118 | hg38 |
| ZNF471 | 19 | 56507662 | 56507750 | 89 | hg38 |
| THBD | 20 | 23049354 | 23049500 | 147 | hg38 |
| JAM2 | 21 | 25640320 | 25640399 | 80 | hg38 |
| SDC2 | 8 | 96493985 | 96494062 | 78 | hg38 |
| FGF14 | 13 | 102394577 | 102394651 | 75 | hg38 |
| CDKN2A | 9 | 21970919 | 21971017 | 99 | hg38 |

TABLE 3

Primer sequences for use with MSRE-qPCR method for DMRs in Table 1 (DMRs with general cancer detection power) (Table 3 discloses SEQ ID NOs 1-28, respectively, in order of columns)

| annotations | chr | start | end | primer_F | primer_R |
|---|---|---|---|---|---|
| HOXA7 | 7 | 27155916 | 27156027 | TCGAACCCATTAATTGGGCCATA (SEQ ID NO: 1) | CGGCGCAGCCTTTCTGGTTT (SEQ ID NO: 15) |
| MIR196B | 7 | 27169630 | 27169719 | CCAAGGAGAGAACCCTGCCATCG (SEQ ID NO: 2) | GCCTGGGGCACTCTGTTGCACT (SEQ ID NO: 16) |
| TNFRSF10D | 8 | 23163995 | 23164099 | TTGTGCGCGTGCAAAGGTTC (SEQ ID NO: 3) | GCGGGAAGGGAGTACAACTGAC (SEQ ID NO: 17) |
| DNM3 | 1 | 171841774 | 171841857 | CAGAGCGCCGGCAAGAGC (SEQ ID NO: 4) | CCCCACTGCCGCATCCTTAC (SEQ ID NO: 18) |
| C1orf230 | 1 | 151721583 | 151721679 | TTAGCGCAGCGCAGCTGGAG (SEQ ID NO: 5) | CCCAGTCCTGGGGCAGCTACA (SEQ ID NO: 19) |
| ZNF568 | 19 | 36916252 | 36916371 | GCCCAAGCCTCACCCTCACACAG (SEQ ID NO: 6) | CGAACCATCCCTCCGCGCCA (SEQ ID NO: 20) |
| C9orf50 | 9 | 129620787 | 129620870 | AGAGTAGCCAACTTTGGGGTTGCT (SEQ ID NO: 7) | GGCACTGTACCGAGCTTGCTGTTCT (SEQ ID NO: 21) |
| NA | 5 | 73436635 | 73436710 | CAGGCTGGGCGGTCTTTGAC (SEQ ID NO: 8) | GGGGTAGCGGGTGCTTCCAG (SEQ ID NO: 22) |
| DLX6-AS1 | 7 | 97014186 | 97014266 | CAAGACCTGGCGCATCTTTGC (SEQ ID NO: 9) | TTGCAGGCTGGATTAGGATGC (SEQ ID NO: 23) |
| DIO3OS, MIR1247 | 14 | 101561395 | 101561505 | TCCGGGCTCAAGTTGCAAGG (SEQ ID NO: 10) | GCGAGGCATCTGGGCTTCAG (SEQ ID NO: 24) |
| GSG1L | 16 | 28063861 | 28063964 | CCGAAAGAAATCCGAGCCAGGGTGA (SEQ ID NO: 11) | GGTTTTGTTGCCCCACGTCC (SEQ ID NO: 25) |
| LONRF2 | 2 | 100322387 | 100322463 | CTCTCAGTCCCGCCGGCTTAGGTA (SEQ ID NO: 12) | GCAAGAGACGCGGACCTGGAGC (SEQ ID NO: 26) |
| PCDH9 | 13 | 67231171 | 67231265 | GCGTGCGAAGTCTCCTCTAGCGGA (SEQ ID NO: 13) | CTCAGGTTTCCAGGCGCGGCT (SEQ ID NO: 27) |
| GFPT2 | 5 | 180353729 | 180353815 | CGTAAGGGGCAGAGCGAGGGT (SEQ ID NO: 14) | CTCAGATGGGAGCGCGGCAGGAA (SEQ ID NO: 28) |

TABLE 4

Primer sequences for use with MSRE-qPCR method for DMRs in Table 2 (DMRs with cancer location specific methylation signal) (Table 4 discloses SEQ ID NOS 29-36, 1, 37-38, 2, 39, 3, 40-63, 15, 64-65, 16, 66, 17, 67-75, 75 and 76-81, respectively, in order of columns)

| Gene | chr | start | end | primer_F | primer_R |
|---|---|---|---|---|---|
| MAST1 | 19 | 12867716 | 12867820 | CCCCCTCCATGCAGCAAGC (SEQ ID NO: 29) | CTCCAGCAGCGCCGAGAAAC (SEQ ID NO: 56) |

TABLE 4-continued

Primer sequences for use with MSRE-qPCR method for DMRs in Table 2 (DMRs with cancer location specific methylation signal) (Table 4 discloses SEQ ID NOS 29-36, 1, 37-38, 2, 39, 3, 40-63, 15, 64-65, 16, 66, 17, 67-75, 75 and 76-81, respectively, in order of columns)

| Gene | chr | start | end | primer_F | primer_R |
|---|---|---|---|---|---|
| KLK10 | 19 | 51019613 | 51019705 | GCAGGTAGCTTCACCTGGGAGTCG (SEQ ID NO: 30) | AGAGGATACCAGCGGCAGACCACA (SEQ ID NO: 57) |
| HOXD8 | 2 | 176129896 | 176130001 | GGGGTTTGTAAACCGAGGCCAGAG (SEQ ID NO: 31) | CGCTGCCTCCACTGTTTCCTCTCA (SEQ ID NO: 58) |
| C2orf88 | 2 | 190180554 | 190180682 | GCCGGCAGCTGCTTGGTAGTTG (SEQ ID NO: 32) | GAGGGTTGCCTCGATACTTCCTCA (SEQ ID NO: 59) |
| PREX1 | 20 | 48828337 | 48828448 | TCACCGCGGGCTACGCCACT (SEQ ID NO: 33) | GCTTTCCCAGCCCGGTGTTT (SEQ ID NO: 60) |
| AMOTL2 | 3 | 134364403 | 134364512 | CCATGGCTTCCTTTCTTTGGCAGA (SEQ ID NO: 34) | TTCCCTGAGGAGTCTGGGGAGGAG (SEQ ID NO: 61) |
| SOX2OT | 3 | 181719490 | 181719596 | GGCAAATTGAGGCCGAGCTG (SEQ ID NO: 35) | CGAGCCCCACACAGCACCTT (SEQ ID NO: 62) |
| SCGN | 6 | 25652114 | 25652232 | TCCCCAAAGCGCAGAGACAGA (SEQ ID NO: 36) | CGTCCCTCAGCCCTCAGCAA (SEQ ID NO: 63) |
| HOXA7 | 7 | 27155916 | 27156027 | TCGAACCCATTAATTGGGCCATA (SEQ ID NO: 1) | CGGCGCAGCCTTTCTGGTTT (SEQ ID NO: 15) |
| HOXA7 | 7 | 27156273 | 27156352 | CCCGGGGATGTTTTGGTCGT (SEQ ID NO: 37) | CCTTTGCGTCCGGCTACGG (SEQ ID NO: 64) |
| HOXA7 | 7 | 27156291 | 27156403 | GTAGGAGGCGCAGGGCAGGT (SEQ ID NO: 38) | CCTCGACCGTTCCGGGCTTA (SEQ ID NO: 65) |
| MIR196B | 7 | 27169630 | 27169719 | CCAAGGAGAGAACCCTGCCATCG (SEQ ID NO: 2) | GCCTGGGGCACTCTGTTGCACT (SEQ ID NO: 16) |
| TNFRSF10D | 8 | 23163949 | 23164031 | GGTGGATCGAAAGCGCCAAA (SEQ ID NO: 39) | TGGCAGTGTAGCTGCGAGAACC (SEQ ID NO: 66) |
| TNFRSF10D | 8 | 23163995 | 23164099 | TTGTGCGCGTGCAAAGGTTC (SEQ ID NO: 3) | GCGGGAAGGGAGTACAACTGACC (SEQ ID NO: 17) |
| NA | 10 | 100830555 | 100830658 | AGCGGCTGAAATTGGTGCGCC (SEQ ID NO: 40) | CTATGCAGGAACCCGCCGACCG (SEQ ID NO: 67) |
| ME3 | 11 | 86672189 | 86672296 | AGATCCGGTGCGGGTGACAG (SEQ ID NO: 41) | CAAGCCACCACGCGGGATTA (SEQ ID NO: 68) |
| ME3 | 11 | 86672338 | 86672429 | GAGCTGAGGTCTACGCGGTCCC (SEQ ID NO: 42) | CCAGCGCGGTCCACCCATTG (SEQ ID NO: 69) |
| TXNRD1 | 12 | 104215675 | 104215784 | GGCTATGACTTCGCTGTTGTCACC (SEQ ID NO: 43) | GGAACTGACGGAGCCGAAGGA (SEQ ID NO: 70) |
| HAPLN3 | 15 | 88895676 | 88895781 | GTCTCCAGACTCGCTGGGAACCAC (SEQ ID NO: 44) | CCCCTCCCCAAACTCTCCTATTCCA (SW ID NO: 71) |

TABLE 4-continued

Primer sequences for use with MSRE-qPCR method for DMRs in Table 2 (DMRs with cancer location specific methylation signal) (Table 4 discloses SEQ ID NOS 29-36, 1, 37-38, 2, 39, 3, 40-63, 15, 64-65, 16, 66, 17, 67-75, 75 and 76-81, respectively, in order of columns)

| Gene | chr | start | end | primer_F | primer_R |
|---|---|---|---|---|---|
| CYBA | 16 | 88651139 | 88651205 | CATCTGTAGGGT GCAGGGCTGTCC (SEQ ID NO: 45) | TATGCCTCGGCGTG GCTAGAGAGG (SEQ ID NO: 72) |
| ZNF568 | 19 | 36916284 | 36916453 | TGTGTTCTGGCC GGAAGTTGAGTG (SEQ ID NO: 46) | CGAATGTTCATCCC GCGCGCAGTT (SEQ ID NO: 73) |
| ZNF582 | 19 | 56393606 | 56393725 | TCCGGGAAACAT AGTCTTTAGGCG T (SEQ ID NO: 47) | GAACAGCACTCCTC CGCGCACTG (SEQ ID NO: 74) |
| ZNF471 | 19 | 56507527 | 56507675 | CCCCACGCGTAC TCACACCGAAG (SEQ ID NO: 48) | GCGGGTAAGAGCA GGAGTGTG (SEQ ID NO: 75) |
| ZNF471 | 19 | 56507558 | 56507675 | GTCGCGCGTTTC CCTCCCAG (SEQ ID NO: 49) | GCGGGTAAGAGCA GGAGTGTG (SEQ ID NO: 75) |
| ZNF471 | 19 | 56507662 | 56507750 | CTGCTCTTACCC GCCGGAACCCTG (SEQ ID NO: 50) | GAGGGACCTTAGA GCAGAGCGGGC (SEQ ID NO: 76) |
| THBD | 20 | 23049354 | 23049500 | TCTGACTGGCAT TGAGGAAGGTCG (SEQ ID NO: 51) | TTGGGGTCCTGGTC CTTGGCGC (SEQ ID NO: 77) |
| JAM2 | 21 | 25640320 | 25640399 | CCGCGTGGTCTG GGCTCTGTAG (SEQ ID NO: 52) | GAATTCCCTCCACC TCCGCCCCAC (SEQ ID NO: 78) |
| SDC2 | 8 | 96493985 | 96494062 | CTTCAGAGAGCA GCCTTCCCGG (SEQ ID NO: 53) | GAACGCGGCGCCC TCTCACTT (SEQ ID NO: 79) |
| FGF14 | 13 | 102394577 | 102394651 | CAACGGAAACTT CCCGCGCTAC (SEQ ID NO: 54) | CTCGCCGGGGCTT CGCTAC (SEQ ID NO: 80) |
| CDKN2A | 9 | 21970919 | 21971017 | GCATCTATGCGG GCATGGTTACTG (SEQ ID NO: 55) | CGTGGACCTGGCTG AGGAGCTG (SEQ ID NO: 81) |

For the avoidance of any doubt, any methylation biomarker provided herein can be, or be included in, among other things, a colorectal cancer, breast cancer, lung cancer and/or pancreatic cancer marker. Additionally, any methylation biomarker herein can be, or be included in, a colorectal cancer, breast cancer, lung cancer and/or pancreatic cancer methylation biomarker.

In some embodiments, said methylation biomarker can be or include a single methylation locus. In some embodiments, a methylation biomarker can be or include two or more methylation loci. In some embodiments, a methylation biomarker can be or include a single differentially methylated region (DMR) (e.g., (i) a DMR selected from those listed in Tables 1-2, 7-11 13 and 15, (ii) a DMR that encompasses a DMR selected from those listed in Tables 1-4, 7-11 13 and 15, (iii) a DMR that overlaps with one or more DMRs selected from those listed in Table 1, or (iv) a DMR that is a portion of a DMR selected from those listed in Tables 1-4, 7-11 13 and 15). In some embodiments, a methylation locus can be or include two or more DMRs (e.g., two, three, four, or more DMRs selected from those listed in Table 1, or two, three, four, or more DMRs, each of which overlap with and/or encompass a DMR selected from those listed in Tables 1-4, 7-11 13 and 15). In some embodiments, a methylation biomarker can be or include a single methylation site. In other embodiments, a methylation biomarker can be or include two or more methylation sites. In some embodiments, a methylation locus can include two or more DMRs and further include DNA regions adjacent to one or more of the included DMRs.

In some instances, a methylation locus is or includes a gene, such as a gene provided in Tables 1-4, 7-11, 13 and 15. In some instances a methylation locus is or includes a portion of a gene, e.g., a portion of a gene provided in Tables 1-4, 7-11, 13 and 15. In some instances, a methylation locus includes but is not limited to identified nucleic acid boundaries of a gene.

In some instances, a methylation locus is or includes a coding region of a gene, such as a coding region of a gene provided in Tables 1-4, 7-11, 13 and 15. In some instances a methylation locus is or includes a portion of the coding region of gene, e.g., a portion of the coding region a gene provided in Tables 1-4, 7-11, 13 and 15. In some instances, a methylation locus includes but is not limited to identified nucleic acid boundaries of a coding region of gene.

In some instances, a methylation locus is or includes a promoter and/or other regulatory region of a gene, such as a promoter and/or other regulatory region of a gene provided in Tables 1-4, 7-11, 13 and 15. In some instances, a methylation locus is or includes a portion of the promoter and/or regulatory region of a gene, e.g., a portion of promoter and/or regulatory region a gene provided in Tables 1-4, 7-11, 13 and 15. In some instances, a methylation locus includes but is not limited to identified nucleic acid boundaries of a promoter and/or other regulatory region of gene. In some embodiments a methylation locus is or includes a high CpG density promoter, or a portion thereof.

In some embodiments, a methylation locus is or includes non-coding sequence. In some embodiments, a methylation locus is or includes one or more exons, and/or one or more introns.

In some embodiments, a methylation locus includes a DNA region extending a predetermined number of nucleotides upstream of a coding sequence, and/or a DNA region extending a predetermined number of nucleotides downstream of a coding sequence. In various instances, a predetermined number of nucleotides upstream and/or downstream and be or include, e.g., 500 bp, 1 kb, 2 kb, 3 kb, 4 kb, 5 kb, 10 kb, 20 kb, 30 kb, 40 kb, 50 kb, 75 kb, or 100 kb. Those of skill in the art will appreciate that methylation biomarkers capable of impacting expression of a coding sequence may typically be within any of these distances of the coding sequence, upstream and/or downstream.

Those of skill in the art will appreciate that a methylation locus identified as a methylation biomarker need not necessarily be assayed in a single experiment, reaction, or amplicon. A single methylation locus identified as a colorectal cancer, breast cancer, lung cancer and/or pancreatic cancer methylation biomarker can be assayed, e.g., in a method including separate amplification (or providing oligonucleotide primers and conditions sufficient for amplification of) of one or more distinct or overlapping DNA regions within a methylation locus, e.g., one or more distinct or overlapping DMRs. Those of skill in the art will further appreciate that a methylation locus identified as a methylation biomarker need not be analyzed for methylation status of each nucleotide, nor each CpG, present within the methylation locus. Rather, a methylation locus that is a methylation biomarker may be analyzed, e.g., by analysis of a single DNA region within the methylation locus, e.g., by analysis of a single DMR within the methylation locus.

DMRs of the present disclosure can be a methylation locus or include a portion of a methylation locus. In some instances, a DMR is a DNA region with a methylation locus that is, e.g., 1 to 5,000 bp in length. In various embodiments, a DMR is a DNA region with a methylation locus that is equal to or less than 5000 bp, 4,000 bp, 3,000 bp, 2,000 bp, 1,000 bp, 950 bp, 900 bp, 850 bp, 800 bp, 750 bp, 700 bp, 650 bp, 600 bp, 550 bp, 500 bp, 450 bp, 400 bp, 350 bp, 300 bp, 250 bp, 200 bp, 150 bp, 100 bp, 50 bp, 40 bp, 30 bp, 20 bp, or 10 bp in length. In some instances, e.g., as set forth herein, a methylation locus has a length of at least 10, at least 15, at least 20, at least 30, at least 50, or at least 75 base pairs.

Methylation biomarkers, including without limitation methylation loci and DMRs provided herein, can include at least one methylation site that is a colorectal cancer, breast cancer, lung cancer and/or pancreatic cancer biomarker.

For clarity, those of skill in the art will appreciate that term methylation biomarker is used broadly, such that a methylation locus can be a methylation biomarker that includes one or more DMRs, each of which DMRs is also itself a methylation biomarker, and each of which DMRs can include one or more methylation sites, each of which methylation sites is also itself a methylation biomarker. Moreover, a methylation biomarker can include two or more methylation loci. Accordingly, status as a methylation biomarker does not turn on the contiguousness of nucleic acids included in a biomarker, but rather on the existence of a change in methylation status for included DNA region(s) between a first state and a second state, such as between colorectal cancer, breast cancer, lung cancer and/or pancreatic cancer, and controls.

As provided herein, a methylation locus can be any of one or more methylation loci each of which methylation loci is, includes, or is a portion of a gene (or specific DMR) identified in Table 1. In some embodiments, a colorectal cancer, breast cancer, lung cancer and/or pancreatic cancer methylation biomarker includes a single methylation locus that is, includes, or is a portion of a gene identified in Tables 1-4, 7-11, 13 and 15.

In some embodiments, a methylation biomarker includes two or more methylation loci, each of which is, includes, or is a portion of a gene identified in Tables 1-4, 7-11, 13 and 15. In some embodiments, a colorectal cancer, breast cancer, lung cancer and/or pancreatic cancer methylation biomarker includes a plurality of methylation loci, each of which is, includes, or is a portion of a gene identified in Tables 1-4, 7-11, 13 and 15.

In various embodiments, a methylation biomarker can be or include one or more individual nucleotides (e.g., a single individual cysteine residue in the context of CpG) or a plurality of individual cysteine residues (e.g., of a plurality of CpGs) present within one or more methylation loci (e.g., one or more DMRs) provided herein. Thus, in certain embodiments a methylation biomarker is or includes methylation status of a plurality of individual methylation sites.

In various embodiments, a methylation biomarker is, includes, or is characterized by change in methylation status that is a change in the methylation of one or more methylation sites within one or more methylation loci (e.g., one or more DMRs). In various embodiments, a methylation biomarker is or includes a change in methylation status that is a change in the number of methylated sites within one or more methylation loci (e.g., one or more DMRs). In various embodiments, a methylation biomarker is or includes a change in methylation status that is a change in the frequency of methylation sites within one or more methylation loci (e.g., one or more DMRs). In various embodiments, a methylation biomarker is or includes a change in methylation status that is a change in the pattern of methylation sites within one or more methylation loci (e.g., one or more DMRs).

In various embodiments, methylation status of one or more methylation loci (e.g., one or more DMRs) is expressed as a fraction or percentage of the one or more methylation loci (e.g., the one or more DMRs) present in a sample that are methylated, e.g., as a fraction of the number of individual DNA strands of DNA in a sample that are methylated at one or more particular methylation loci (e.g., one or more particular DMRs). Those of skill in the art will appreciate that, in some instances, the fraction or percentage of methylation can be calculated from the ratio of methylated DMRs to unmethylated DMRs for one or more analyzed DMRs, e.g., within a sample.

In various embodiments, methylation status of one or more methylation loci (e.g., one or more DMRs) is compared to a reference methylation status value and/or to methylation status of the one or more methylation loci (e.g., one or more DMRs) in a reference sample. In certain instances, a reference is a non-contemporaneous sample from the same source, e.g., a prior sample from the same source, e.g., from the same subject. In certain instances, a reference for the methylation status of one or more methylation loci (e.g., one or more DMRs) is the methylation status of the one or more methylation loci (e.g., one or more DMRs) in a sample (e.g., a sample from a subject), or a plurality of samples, known to represent a particular state (e.g., a cancer state or a non-cancer state). Thus, a reference can be or include one or more predetermined thresholds, which thresholds can be quantitative (e.g., a methylation value) or qualitative. Those of skill in the art will appreciate that a reference measurement is typically produced by measurement using a methodology identical to, similar to, or comparable to that by which the non-reference measurement was taken.

Cancers

In certain embodiments, methods and compositions of the present disclosure are useful for screening for colorectal cancer, breast cancer, lung cancer and/or pancreatic cancer. In other embodiments, the methods and compositions are useful for screening for other cancers. In general, examples of different types of cancers include, for example, colorectal cancer, hematopoietic cancers including leukemias, lymphomas (Hodgkin's and non-Hodgkin's), myelomas and myeloproliferative disorders: sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like. Cancers include cancers at any of the various possible stages known in the art, including, e.g., Stage 0, Stage I, Stage II, Stage III, and/or Stage IV. In certain instances, the present disclosure includes screening of early stage cancer.

Subjects and Samples

A sample analyzed using methods and compositions provided herein can be any biological sample and/or any sample including nucleic acids. In various particular embodiments, a sample analyzed using methods and compositions provided herein can be a sample from a mammal. In various particular embodiments, a sample analyzed using methods and compositions provided herein can be a sample from a human subject. In various particular embodiments, a sample analyzed using methods and compositions provided herein can be a sample from a mouse, rat, pig, horse, chicken, or cow.

In various instances, a human subject is a subject diagnosed or seeking diagnosis as having, diagnosed as or seeking diagnosis as at risk of having, and/or diagnosed as or seeking diagnosis as at immediate risk of having, colorectal cancer, breast cancer, lung cancer and/or pancreatic cancer. In various instances, a human subject is a subjected identified as a subject in need of screening for colorectal cancer, breast cancer, lung cancer and/or pancreatic cancer. In certain instances, a human subject is a subject identified as in need of colorectal cancer, breast cancer, lung cancer and/or pancreatic cancer screening by a medical practitioner. In various instances, a human subject is identified as in need of colorectal cancer, breast cancer, lung cancer and/or pancreatic cancer screening due to age, e.g., due to an age equal to or greater than 45 years, e.g., an age equal to or greater than 45, 50, 55, 60, 65, 70, 75, 80, 85, or 90 years, though in some instances a subject 18 years old or older may be identified as at risk and/or in need of screening for colorectal cancer, breast cancer, lung cancer and/or pancreatic cancer. In various instances, a human subject is identified as being high risk and/or in need of screening for a colorectal cancer, breast cancer, lung cancer and/or pancreatic cancer based on, without limitation, familial history, prior diagnoses, and/or an evaluation by a medical practitioner. In various instances, a human subject is a subject not diagnosed as having, not at risk of having, not at immediate risk of having, not diagnosed as having, and/or not seeking diagnosis for a cancer such as a colorectal cancer, breast cancer, lung cancer, pancreatic cancer, or any combination thereof.

A sample from a subject, e.g., a human or other mammalian subject, can be a sample of, e.g., blood, blood component (e.g., plasma, buffy coat), cfDNA (cell free DNA), ctDNA (circulating tumor DNA), stool, or advanced adenoma and/or colorectal tissue. In some particular embodiments, a sample is an excretion or bodily fluid of a subject (e.g., stool, blood, plasma, lymph, or urine of a subject) or a tissue sample of colorectal cancer, breast cancer, lung cancer and/or pancreatic cancer. A sample from a subject can be a cell or tissue sample, e.g., a cell or tissue sample that is of a cancer or includes cancer cells, e.g., of a tumor or of a metastatic tissue. In various embodiments, a sample from a subject, e.g., a human or other mammalian subject, can be obtained by biopsy (e.g., colonoscopy resection, fine needle aspiration or tissue biopsy) or surgery.

In various particular embodiments, a sample is a sample of cell-free DNA (cfDNA). cfDNA is typically found in biological fluids (e.g., plasma, serum, or urine) in short, double-stranded fragments. The concentration of cfDNA is typically low, but can significantly increase under particular conditions, including without limitation pregnancy, autoimmune disorder, myocardial infraction, and cancer. Circulating tumor DNA (ctDNA) is the component of circulating DNA specifically derived from cancer cells. ctDNA can be present in human fluids. For example in some instances, ctDNA can be found bound to and/or associated with leukocytes and erythrocytes. In some instances, ctDNA can be found not bound to and/or associated with leukocytes and erythrocytes. Various tests for detection of tumor-derived cfDNA are based on detection of genetic or epigenetic modifications that are characteristic of cancer (e.g., of a relevant cancer). Genetic or epigenetic modifications characteristic of cancer can include, without limitation, oncogenic or cancer-associated mutations in tumor-suppressor genes, activated oncogenes, hypermethylation, and/or chromosomal disorders. Detection of genetic or epigenetic modifications characteristic of cancer or pre-cancer can confirm that detected cfDNA is ctDNA.

cfDNA and ctDNA provide a real-time or nearly real-time metric of the methylation status of a source tissue. cfDNA and ctDNA have a half-life in blood of about 2 hours, such that a sample taken at a given time provides a relatively timely reflection of the status of a source tissue.

Various methods of isolating nucleic acids from a sample (e.g., of isolating cfDNA from blood or plasma) are known in the art. Nucleic acids can be isolated, e.g., without limitation, standard DNA purification techniques, by direct gene capture (e.g., by clarification of a sample to remove assay-inhibiting agents and capturing a target nucleic acid, if present, from the clarified sample with a capture agent to produce a capture complex, and isolating the capture complex to recover the target nucleic acid).

Methods of Measuring Methylation Status

Methylation status can be measured by a variety of methods known in the art and/or by methods provided herein. Those of skill in the art will appreciate that a method for measuring methylation status can generally be applied to samples from any source and of any kind, and will further be aware of processing steps available to modify a sample into a form suitable for measurement by a given methodology. Methods of measuring methylation status include, without limitation, methods including whole genome bisulfite sequencing, targeted bisulfite sequencing, targeted enzymatic methylation sequencing, methylation-status-specific polymerase chain reaction (PCR), methods including mass spectrometry, methylation arrays, methods including methylation-specific nucleases, methods including mass-based separation, methods including target-specific capture, and methods including methylation-specific oligonucleotide primers. Certain particular assays for methylation utilize a bisulfite reagent (e.g., hydrogen sulfite ions) or enzymatic conversion reagents (e.g., Tet methylcytosine dioxygenase 2).

Bisulfite reagents can include, among other things, bisulfite, disulfite, hydrogen sulfite, or combinations thereof, which reagents can be useful in distinguishing methylated and unmethylated nucleic acids. Bisulfite interacts differently with cytosine and 5-methylcytosine. In typical bisulfite-based methods, contacting of DNA with bisulfite deaminates unmethylated cytosine to uracil, while methylated cytosine remains unaffected; methylated cytosines, but not unmethylated cytosines, are selectively retained. Thus, in a bisulfite processed sample, uracil residues stand in place of, and thus provide an identifying signal for, unmethylated cytosine residues, while remaining (methylated) cytosine residues thus provide an identifying signal for methylated cytosine residues. Bisulfite processed samples can be analyzed, e.g., by next generation sequencing (NGS).

Enzymatic conversion reagents can include Tet methylcytosine dioxygenase 2 (TET2). TET2 oxidizes 5-methylcytosine and thus protects it from the consecutive deamination by APOBEC. APOBEC deaminates unmethylated cytosine to uracile, while oxidizes 5-mthylcytosine remains unaffected. Thus, in a TET2 processed sample, uracil residues stand in place of, and thus provide an identifying signal for, unmethylated cytosine residues, while remaining (methylated) cytosine residues thus provide an identifying signal for methylated cytosine residues. TET2 processed samples can be analyzed, e.g., by next generation sequencing (NGS).

Methods of measuring methylation status can include, without limitation, massively parallel sequencing (e.g., next-generation sequencing) to determine methylation state, e.g., sequencing by—synthesis, real-time (e.g., single-molecule) sequencing, bead emulsion sequencing, nanopore sequencing, or other sequencing techniques known in the art. In some embodiments, a method of measuring methylation status can include whole-genome sequencing, e.g., measuring whole genome methylation status from bisulfite or enzymatically treated material with base-pair resolution.

In some embodiments, methods of measuring methylation status include, without limitation, targeted bisulfite sequencing, targeted enzymatic methylation sequencing, and reduced representation bisulfite sequencing e.g., utilizing use of restriction enzymes to measure methylation status of high CpG content regions from bisulfite or enzymatically treated material with base-pair resolution.

In some embodiments, a method of measuring methylation status can include targeted sequencing e.g., measuring methylation status of pre-selected genomic location from bisulfite or enzymatically treated material with base-pair resolution.

In some embodiments, the pre-selection (capture) of regions of interest can be done by complementary in vitro synthesized oligonucleotide sequences (either baits, primers or probes).

In some embodiments, a method for measuring methylation status can include Illumina Methylation Assays e.g., measuring over 850,000 methylation sites quantitatively across a genome at single-nucleotide resolution.

Various methylation assay procedures can be used in conjunction with bisulfite treatment to determine methylation status of a target sequence such as a DMR. Such assays can include, among others, Methylation-Specific Restriction Enzyme qPCR, sequencing of bisulfite-treated nucleic acid, PCR (e.g., with sequence-specific amplification), Methylation Specific Nuclease-assisted Minor-allele Enrichment PCR, and Methylation-Sensitive High Resolution Melting. In some embodiments, DMRs are amplified from a bisulfite-treated DNA sample and a DNA sequencing library is prepared for sequencing according to, e.g., an Illumina protocol or transpose-based Nextera XT protocol. In certain embodiments, high-throughput and/or next-generation sequencing techniques are used to achieve base-pair level resolution of DNA sequence, permitting analysis of methylation status.

Another method, that can be used for methylation detection includes PCR amplification with methylation-specific oligonucleotide primers (MSP methods), e.g., as applied to bisulfite-treated sample (see, e.g., Herman 1992 Proc. Natl. Acad. Sci. USA 93: 9821-9826, which is herein incorporated by reference with respect to methods of determining methylation status). Use of methylation-status-specific oligonucleotide primers for amplification of bisulfite-treated DNA allows differentiation between methylated and unmethylated nucleic acids. Oligonucleotide primer pairs for use in MSP methods include at least one oligonucleotide primer capable of hybridizing with sequence that includes a methylation site, e.g., a CpG. An oligonucleotide primer that includes a T residue at a position complementary to a cytosine residue will selectively hybridize to templates in which the cytosine was unmethylated prior to bisulfite treatment, while an oligonucleotide primer that includes a G residue at a position complementary to a cytosine residue will selectively hybridize to templates in which the cytosine was methylated cytosine prior to bisulfite treatment. MSP results can be obtained with or without sequencing amplicons, e.g., using gel electrophoresis. MSP (methylation-specific PCR) allows for highly sensitive detection (detection level of 0.1% of the alleles, with full specificity) of locus-specific DNA methylation, using PCR amplification of bisulfite-converted DNA.

Another method that can be used to determine methylation status after bisulfite treatment of a sample is Methylation-Sensitive High Resolution Melting (MS-HRM) PCR (see, e.g., Hussmann 2018 Methods Mol Biol. 1708:551-571, which is herein incorporated by reference with respect to methods of determining methylation status). MS-HRM is an in-tube, PCR-based method to detect methylation levels at specific loci of interest based on hybridization melting. Bisulfite treatment of the DNA prior to performing MS-HRM ensures a different base composition between methylated and unmethylated DNA, which is used to separate the resulting amplicons by high resolution melting. A unique primer design facilitates a high sensitivity of the assays enabling detection of down to 0.1-1% methylated alleles in an unmethylated background. Oligonucleotide primers for MS-HRM assays are designed to be complementary to the methylated allele, and a specific annealing temperature enables these primers to anneal both to the methylated and the unmethylated alleles thereby increasing the sensitivity of the assays.

Another method that can be used to determine methylation status after bisulfite treatment of a sample is Quantitative Multiplex Methylation-Specific PCR (QM-MSP). QM-MSP uses methylation specific primers for sensitive quantification of DNA methylation (see, e.g., Fackler 2018 Methods Mol Biol. 1708:473-496, which is herein incorporated by reference with respect to methods of determining methylation status). QM-MSP is a two-step PCR approach, where in the first step, one pair of gene-specific primers (forward and reverse) amplifies the methylated and unmethylated copies of the same gene simultaneously and in multiplex, in one PCR reaction. This methylation-independent amplification step produces amplicons of up to $10^9$ copies per μL after 36 cycles of PCR. In the second step, the amplicons of the first reaction are quantified with a standard curve using real-time PCR and two independent fluorophores to detect methylated/unmethylated DNA of each gene in the same well (e.g., 6FAM and VIC). One methylated copy is detectable in 100,000 reference gene copies.

Another method that can be used to determine methylation status after bisulfite treatment of a sample is Methylation Specific Nuclease-assisted Minor-allele Enrichment (MS-NaME) (see, e.g., Liu 2017 Nucleic Acids Res. 45(6): e39, which is herein incorporated by reference with respect to methods of determining methylation status). Ms-NaME is based on selective hybridization of probes to target sequences in the presence of DNA nuclease specific to double-stranded (ds) DNA (DSN), such that hybridization results in regions of double-stranded DNA that are subsequently digested by the DSN. Thus, oligonucleotide probes targeting unmethylated sequences generate local double stranded regions resulting to digestion of unmethylated targets; oligonucleotide probes capable of hybridizing to methylated sequences generate local double-stranded regions that result in digestion of methylated targets, leaving methylated targets intact. Moreover, oligonucleotide probes can direct DSN activity to multiple targets in bisulfite-treated DNA, simultaneously. Subsequent amplification can enrich non-digested sequences. Ms-NaME can be used, either independently or in combination with other techniques provided herein.

Another method that can be used to determine methylation status after bisulfite treatment of a sample is Methylation-sensitive Single Nucleotide Primer Extension (Ms-SNuPE™) (see, e.g., Gonzalgo 2007 Nat Protoc. 2(8):1931-6, which is herein incorporated by reference with respect to methods of determining methylation status). In Ms-SNuPE, strand-specific PCR is performed to generate a DNA template for quantitative methylation analysis using Ms-SNuPE. SNuPE is then performed with oligonucleotide(s) designed to hybridize immediately upstream of the CpG site(s) being interrogated. Reaction products can be electrophoresed on polyacrylamide gels for visualization and quantitation by phosphor-image analysis. Amplicons can also carry a directly or indirectly detectable labels such as a fluorescent label, radionuclide, or a detachable molecule fragment or other entity having a mass that can be distinguished by mass spectrometry. Detection may be carried out and/or visualized by means of, e.g., matrix assisted laser desorption/ionization mass spectrometry (MALDI) or using electron spray mass spectrometry (ESI).

Certain methods that can be used to determine methylation status after bisulfite treatment of a sample utilize a first oligonucleotide primer, a second oligonucleotide primer, and an oligonucleotide probe in an amplification-based method. For instance, the oligonucleotide primers and probe can be used in a method of real-time polymerase chain reaction (PCR) or droplet digital PCR (ddPCR). In various instances, the first oligonucleotide primer, the second oligonucleotide primer, and/or the oligonucleotide probe selectively hybridize methylated DNA and/or unmethylated DNA, such that amplification or probe signal indicate methylation status of a sample.

Other bisulfite-based methods for detecting methylation status (e.g., the presence of level of 5-methylcytosine) are disclosed, e.g., in Frommer (1992 Proc Natl Acad Sci USA. 1; 89(5):1827-31, which is herein incorporated by reference with respect to methods of determining methylation status).

In certain MSRE-qPCR embodiments, the amount of total DNA is measured in an aliquot of sample in native (e.g., undigested) form using, e.g., real-time PCR or digital PCR.

Various amplification technologies can be used alone or in conjunction with other techniques described herein for detection of methylation status. Those of skill in the art, having reviewed the present specification, will understand how to combine various amplification technologies known in the art and/or described herein together with various other technologies for methylation status determination known in the art and/or provided herein. Amplification technologies include, without limitation, PCR, e.g., quantitative PCR (qPCR), real-time PCR, and/or digital PCR. Those of skill in the art will appreciate that polymerase amplification can multiplex amplification of multiple targets in a single reaction. PCR amplicons are typically 100 to 2000 base pairs in length. In various instances, an amplification technology is sufficient to determine methylations status.

Digital PCR (dPCR) based methods involve dividing and distributing a sample across wells of a plate with 96-, 384-, or more wells, or in individual emulsion droplets (ddPCR) e.g., using a microfluidic device, such that some wells include one or more copies of template and others include no copies of template. Thus, the average number of template molecules per well is less than one prior to amplification. The number of wells in which amplification of template occurs provides a measure of template concentration. If the sample has been contacted with MSRE, the number of wells in which amplification of template occurs provides a measure of the concentration of methylated template.

In various embodiments a fluorescence-based real-time PCR assay, such as MethyLight™, can be used to measure methylation status (see, e.g., Campan 2018 Methods Mol Biol. 1708:497-513, which is herein incorporated by reference with respect to methods of determining methylation status). MethyLight is a quantitative, fluorescence-based, real-time PCR method to sensitively detect and quantify DNA methylation of candidate regions of the genome. MethyLight is uniquely suited for detecting low-frequency methylated DNA regions against a high background of unmethylated DNA, as it combines methylation-specific priming with methylation-specific fluorescent probing. Additionally, MethyLight can be combined with Digital PCR, for the highly sensitive detection of individual methylated molecules, with use in disease detection and screening.

Real-time PCR-based methods for use in determining methylation status typically include a step of generating a standard curve for unmethylated DNA based on analysis of external standards. A standard curve can be constructed from at least two points and can permit comparison of a real-time Ct value for digested DNA and/or a real-time Ct value for undigested DNA to known quantitative standards. In particular instances, sample Ct values can be determined for MSRE-digested and/or undigested samples or sample aliquots, and the genomic equivalents of DNA can be calculated from the standard curve. Ct values of MSRE-digested and undigested DNA can be evaluated to identify amplicons digested (e.g., efficiently digested; e.g., yielding a Ct value of 45). Amplicons not amplified under either digested or undigested conditions can also be identified. Corrected Ct values for amplicons of interest can then be directly compared across conditions to establish relative differences in methylation status between conditions. Alternatively or additionally, delta-difference between the Ct values of digested and undigested DNA can be used to establish relative differences in methylation status between conditions.

In certain particular embodiments, whole genome bisulfite sequencing among other techniques, can be used to determine the methylation status of a colorectal cancer, breast cancer, lung cancer and/or pancreatic cancer methylation biomarker that is or includes a single methylation locus. In certain particular embodiments, whole genome bisulfite sequencing, among other techniques, can be used to determine the methylation status of a methylation biomarker that is or includes two or more methylation loci.

Those of skill in the art will further appreciate that methods, reagents, and protocols for whole genome bisulfite sequencing are well-known in the art. Unlike traditional whole genome sequencing, whole genome bisulfite sequencing is able to detect the methylation status of the cytosine nucleotide, due to deamination treatment with bisulfite reagent.

Those of skill in the art will appreciate that in embodiments in which a plurality of methylation loci (e.g., a plurality of DMRs) are analyzed for methylation status in a method of screening for colorectal cancer, breast cancer, lung cancer and/or pancreatic cancer provided herein, methylation status of each methylation locus can be measured or represented in any of a variety of forms, and the methylation statuses of a plurality of methylation loci (preferably each measured and/or represented in a same, similar, or comparable manner) be together or cumulatively analyzed or represented in any of a variety of forms. In various embodiments, methylation status of each methylation locus can be measured as methylation portion. In various embodiments, methylation status of each methylation locus can be represented as the percentage value of methylated reads from total sequencing reads compared against reference sample. In various embodiments, methylation status of each methylation locus can be represented as a qualitative comparison to a reference, e.g., by identification of each methylation locus as hypermethylated or hypomethylated.

In some embodiments in which a single methylation locus is analyzed, hypermethylation of the single methylation locus constitutes a diagnosis that a subject is suffering from or possibly suffering from a condition (e.g., colorectal cancer, breast cancer, lung cancer and/or pancreatic cancer), while absence of hypermethylation of the single methylation locus constitutes a diagnosis that the subject is likely not suffering from a condition. In some embodiments, hypermethylation of a single methylation locus (e.g., a single DMR) of a plurality of analyzed methylation loci constitutes a diagnosis that a subject is suffering from or possibly suffering from the condition, while the absence of hypermethylation at any methylation locus of a plurality of analyzed methylation loci constitutes a diagnosis that a subject is likely not suffering from the condition. In some embodiments, hypermethylation of a determined percentage (e.g., a predetermined percentage) of methylation loci (e.g., at least 10% (e.g., at least 10%, at least 20%, at least 30%, at least 40%, at least 50%, at least 60%, at least 70%, at least 80%, at least 90%, or 100%)) of a plurality of analyzed methylation loci constitutes a diagnosis that a subject is suffering from or possibly suffering from the condition, while the absence of hypermethylation of a determined percentage (e.g., a predetermined percentage) of methylation loci (e.g., at least 10% (e.g., at least 10%, at least 20%, at least 30%, at least 40%, at least 50%, at least 60%, at least 70%, at least 80%, at least 90%, or 100%)) of a plurality of analyzed methylation loci constitutes a diagnosis that a subject is not likely suffering from the condition. In some embodiments, hypermethylation of a determined number (e.g., a predetermined number) of methylation loci (e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 DMRs) of a plurality of analyzed methylation loci (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 DMRs) constitutes a diagnosis that a subject is suffering from or possibly suffering from the condition, while the absence of hypermethylation of a determined number (e.g., a predetermined number) of methylation loci (e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 DMRs) of a plurality of analyzed methylation loci (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 DMRs) constitutes a diagnosis that a subject is not likely suffering from the condition.

In some embodiments, methylation status of a plurality of methylation loci (e.g., a plurality of DMRs) is measured qualitatively or quantitatively and the measurement for each of the plurality of methylation loci are combined to provide a diagnosis. In some embodiments, the qualitative of quantitatively measured methylation status of each of a plurality of methylation loci is individually weighted, and weighted values are combined to provide a single value that can be comparative to a reference in order to provide a diagnosis.

Applications

Methods and compositions of the present disclosure can be used in any of a variety of applications. For example, methods and compositions of the present disclosure can be used to screen, or aid in screening for a colorectal cancer, breast cancer, lung cancer and/or pancreatic cancer. In various instances, screening using methods and compositions of the present disclosure can detect any stage of colorectal cancer, breast cancer, lung cancer and/or pancreatic cancer, including without limitation early-stage cancer. In some embodiments, screening using methods and compositions of the present disclosure is applied to individuals 45 years of age or older, e.g., 45, 50, 55, 60, 65, 70, 75, 80, 85, or 90 years or older. In some embodiments, screening using methods and compositions of the present disclosure is applied to individuals 20 years of age or older, e.g., 20, 25, 30, 35, 40, 45, 50, 55, 60, 65, 70, 75, 80, 85, or 90 years or older. In some embodiments, screening using methods and compositions of the present disclosure is applied to individuals 20 to 50 years of age, e.g., 20 to 30 years of age, 20 to 40 years of age, 20 to 50 years of age, 30 to 40 years of age, 30 to 50 years of age, or 40 to 50 years of age. In various embodiments, screening using methods and compositions of the present disclosure is applied to individuals experiencing abdominal pain or discomfort, e.g., experiencing undiagnosed or incompletely diagnosed abdominal pain or discomfort. In various embodiments, screening using methods and compositions of the present disclosure is applied to individuals experiencing no symptoms likely to be associated with a colorectal cancer, breast cancer, lung cancer and/or pancreatic cancer. Thus, in certain embodiments, screening using methods and compositions of the present disclosure is fully or partially preventative or prophylactic, at least with respect to later or non-early stages of cancer.

In various embodiments, colorectal cancer, breast cancer, lung cancer and/or pancreatic cancer screening using methods and compositions of the present disclosure can be applied to an asymptomatic human subject. As used herein, a subject can be referred to as "asymptomatic" if the subject does not report, and/or demonstrate by non-invasively observable indicia (e.g., without one, several, or all of device-based probing, tissue sample analysis, bodily fluid analysis, surgery, or colorectal cancer, breast cancer, lung cancer and/or pancreatic cancer screening), sufficient characteristics of the condition to support a medically reasonable suspicion that the subject is likely suffering from the condition. Detection of a colorectal cancer, breast cancer, lung cancer and/or pancreatic cancer is particularly likely in asymptomatic individuals screened in accordance with methods and compositions of the present disclosure.

Those of skill in the art will appreciate that regular, preventative, and/or prophylactic screening for a colorectal cancer, breast cancer, lung cancer and/or pancreatic cancer improves diagnosis. As noted above, early stage cancers include, according to at least one system of cancer staging, Stages 0 to II C of cancer. Thus, the present disclosure provides, among other things, methods and compositions particularly useful for the diagnosis and treatment of colorectal cancer, breast cancer, lung cancer and/or pancreatic cancer. Generally, and particularly in embodiments in which screening in accordance with the present disclosure is carried out annually, and/or in which a subject is asymptomatic at time of screening, methods and compositions of the present invention are especially likely to detect early stage cancer.

In various embodiments, colorectal cancer, breast cancer, lung cancer and/or pancreatic cancer screening in accordance with the present disclosure is performed once for a given subject or multiple times for a given subject. In various embodiments, colorectal cancer, breast cancer, lung cancer and/or pancreatic cancer screening in accordance with the present disclosure is performed on a regular basis, e.g., every six months, annually, every two years, every three years, every four years, every five years, or every ten years.

In various embodiments, screening using methods and compositions disclosed herein will provide a diagnosis of a condition (e.g., a type or class of a colorectal cancer, breast cancer, lung cancer and/or pancreatic cancer). In other instances, screening for colorectal cancer, breast cancer, lung cancer and/or pancreatic cancer using methods and compositions disclosed herein will be indicative of having one or more conditions, but not definitive for diagnosis of a particular condition. For example, screening may be used to classify a subject as having one or more conditions or combination of conditions including, but not limited to, colorectal cancer, breast cancer, lung cancer and/or pancreatic cancer. Screening may also be used to classify a subject as having a colorectal cancer, breast cancer, lung cancer and/or pancreatic cancer without identifying which condition the subject has. In various instances, screening using methods and compositions of the present disclosure can be followed by a further diagnosis-confirmatory assay, which further assay can confirm, support, undermine, or reject a diagnosis resulting from prior screening, e.g., screening in accordance with the present disclosure.

As used herein, a diagnosis-confirmatory assay can be a colorectal cancer, breast cancer, lung cancer and/or pancreatic cancer assay that provides a diagnosis recognized as definitive by medical practitioners, e.g., a colonoscopy-based diagnosed, or a colorectal cancer assay that substantially increases or decreases the likelihood that a prior diagnosis was correct, e.g., a diagnosis resulting from screening in accordance with the present disclosure. Diagnosis-confirmatory assays could include existing screening technologies, which are generally in need of improvement with respect to one or more of sensitivity, specificity, and non-invasiveness, particularly in the detection of early stage cancers.

In some instances, a diagnosis-confirmatory assay is a test that is or includes a visual or structural inspection of subject tissues, e.g., by colonoscopy. In some embodiments, colonoscopy includes or is followed by histological analysis. Visual and/or structural assays for cancer can include inspection of the structure of the colon and/or rectum for any abnormal tissues and/or structures. Visual and/or structural inspection can be conducted, for example, by use of a scope via the rectum or by CT-scan. In some instances, a diagnosis-confirmatory assay is a colonoscopy, e.g., including or followed by histological analysis. According to some reports, colonoscopy is currently the predominant and/or most relied upon diagnosis-confirmatory assay.

Another visual and/or structural diagnosis confirmatory assay based on computer tomography (CT) is CT colonography, sometimes referred to as virtual colonoscopy. A CT scan utilizes numerous x-ray images of the colon and/or rectum to produce dimensional representations of the colon. Although useful as a diagnosis-confirmatory assay, some reports suggest that CT colonography is not sufficient for replacement of colonoscopy, at least in part because a medical practitioner has not physically accessed the subject's colon to obtain tissue for histological analysis.

Another diagnosis-confirmatory assay can be a sigmoidoscopy. In sigmoidoscopy, a sigmoidoscope is used via the rectum to image portions of the colon and/or rectum. According to some reports, sigmoidoscopy is not widely used.

In some instances, a diagnosis-confirmatory assay is a stool-based assay. Typically, stool-based assays, when used in place of visual or structural inspection, are recommended to be utilized at a greater frequency than would be required if using visual or structural inspection. In some instances, a diagnosis-confirmatory assay is a guiac-based fecal occult blood test or a fecal immunochemical test (gFOBTs/FITs) (see, e.g., Navarro 2017 World J Gastroenterol. 23(20): 3632-3642, which is herein incorporated by reference with respect to colorectal cancer assays). FOBTs and FITs are sometimes used for diagnosis of colorectal cancer (see, e.g., Nakamura 2010 J Diabetes Investig. October 19; 1(5):208-11, which is herein incorporated by reference with respect to colorectal cancer assays). FIT is based on detection of occult blood in stool, the presence of which is often indicative of colorectal cancer but is often not in sufficient volume to permit identification by the unaided eye. For example, in a typical FIT, the test utilizes hemoglobin-specific reagent to test for occult blood in a stool sample. In various instances, FIT kits are suitable for use by individuals in their own homes. When used in the absence of other diagnosis-confirmatory assays, FIT may be recommended for use on an annual basis. FIT is generally not relied upon to provide sufficient diagnostic information for conclusive diagnosis of colorectal cancer.

Diagnosis-confirmatory assays also include gFOBT, which is designed to detect occult blood in stool by chemical reaction. Like FIT, when used in the absence of other diagnosis-confirmatory assays, gFOBT may be recommended for use on an annual basis. gFOBT is generally not relied upon to provide sufficient diagnostic information for conclusive diagnosis of colorectal cancer.

Diagnosis-confirmatory assays can also include stool DNA testing. Stool DNA testing for colorectal cancer can be designed to identify DNA sequences characteristic of cancer in stool samples. When used in the absence of other diagnosis-confirmatory assays, stool DNA testing may be recommended for use every three years. Stool DNA testing is generally not relied upon to provide sufficient diagnostic information for conclusive diagnosis of colorectal cancer.

One particular screening technology is a stool-based screening test (Cologuard® (Exact Sciences Corporation, Madison, Wis., United States), which combines an FIT assay with analysis of DNA for abnormal modifications, such as mutation and methylation. The Cologuard® test demonstrates improved sensitivity as compared to FIT assay alone, but can be clinically impracticable or ineffective due to low compliance rates, which low compliance rates are at least in part due to subject dislike of using stool-based assays (see, e.g., doi: 10.1056/NEJMc1405215 (e.g., 2014 N Engl J Med. 371(2):184-188)). The Cologuard® test appears to leave almost half of the eligible population out of the screening programs (see, e.g., van der Vlugt 2017 Br J Cancer. 116(1):44-49). Use of screening as provided herein, e.g., by a blood-based analysis, would increase the number of individuals electing to screen for colorectal cancer (see, e.g., Adler 2014 BMC Gastroenterol. 14:183; Liles 2017 Cancer Treatment and Research Communications 10: 27-31). To present knowledge, only one existing screening technology for colorectal cancer, Epiprocolon, is FDA-approved and CE-IVD marked and is blood-based. Epiprocolon is based on hypermethylation of SEPT9 gene. The Epiprocolon test suffers from low accuracy for colorectal cancer detection with sensitivity of 68% and advanced adenoma sensitivity of only 22% (see, e.g., Potter 2014 Clin Chem. 60(9):1183-91). There is need in the art for, among other things, a non-invasive colorectal cancer screen that will likely achieve high subject adherence with high and/or improved specificity and/or sensitivity.

In various embodiments, screening in accordance with methods and compositions of the present disclosure reduces colorectal cancer, breast cancer, lung cancer and/or pancreatic cancer mortality, e.g., by early colorectal cancer diagnosis. Data supports that colorectal cancer screening reduces colorectal cancer mortality, which effect persisted for over 30 years (see, e.g., Shaukat 2013 N Engl J Med. 369(12): 1106-14). Moreover, colorectal cancer is particularly difficult to treat at least in part because colorectal cancer, absent timely screening, may not be detected until cancer is past early stages. For at least this reason, treatment of colorectal cancer is often unsuccessful. To maximize population-wide improvement of colorectal cancer outcomes, utilization of screening in accordance with the present disclosure can be paired with, e.g., recruitment of eligible subjects to ensure widespread screening.

In various embodiments, screening of colorectal cancer, breast cancer, lung cancer and/or pancreatic cancer including one or more methods and/or compositions disclosed herein is followed by treatment of colorectal cancer, breast cancer, lung cancer and/or pancreatic cancer, e.g., treatment of early stage cancer. In various embodiments, treatment of colorectal cancer, colorectal cancer, breast cancer, lung cancer and/or pancreatic cancer, e.g., early stage cancer, includes administration of a therapeutic regimen including one or more of surgery, radiation therapy, and chemotherapy. In various embodiments, treatment of colorectal cancer, breast cancer, lung cancer and/or pancreatic cancer, e.g., early stage cancer, includes administration of a therapeutic regimen.

In various embodiments, treatment of colorectal cancer, breast cancer, lung cancer and/or pancreatic cancer includes treatment of early stage cancer by surgical removal of cancerous tissue.

In various embodiments, treatment of colorectal cancer, breast cancer, lung cancer and/or pancreatic cancer includes treatment of early stage cancer by one or more of surgical removal of cancerous tissue, surgery to remove lymph nodes near to identified colorectal cancer tissue, and chemotherapy (e.g., administration of one or more of 5-FU and leucovorin, oxaliplatin, or capecitabine).

In various embodiments, treatment of colorectal cancer, breast cancer, lung cancer and/or pancreatic cancer includes treatment by one or more of surgical removal of cancerous tissue, surgical removal of lymph nodes near to identified colorectal cancer tissue, chemotherapy (e.g., administration of one or more of 5-FU, leucovorin, oxaliplatin, capecitabine, e.g., in a combination of (i) 5-FU and leucovorin, (ii) 5-FU, leucovorin, and oxaliplatin (e.g., FOLFOX), or (iii) capecitabine and oxaliplatin (e.g., CAPEOX)), and radiation therapy.

In various embodiments, treatment of colorectal cancer, breast cancer, lung cancer and/or pancreatic cancer includes one or more of surgical removal of cancerous tissue, surgical removal of lymph nodes near to identified colorectal cancer tissue, surgical removal of metastases, chemotherapy (e.g., administration of one or more of 5-FU, leucovorin, oxaliplatin, capecitabine, irinotecan, VEGF-targeted therapeutic agent (e.g., bevacizumab, ziv-aflibercept, or ramucirumab), EGFR-targeted therapeutic agent (e.g., cetuximab or panitumumab), Regorafenib, trifluridine, and tipiracil, e.g., in a combination of or including (i) 5-FU and leucovorin, (ii) 5-FU, leucovorin, and oxaliplatin (e.g., FOLFOX), (iii) capecitabine and oxaliplatin (e.g., CAPEOX), (iv) leucovorin, 5-FU, oxaliplatin, and irinotecan (FOLFOXIRI), and (v) trifluridine and tipiracil (Lonsurf)), radiation therapy, hepatic artery infusion (e.g., if cancer has metastasized to liver), ablation of tumors, embolization of tumors, colon stent, colorectomy, colostomy (e.g., diverting colostomy), and immunotherapy (e.g., pembrolizumab).

Those of skill in the art understand that treatments of colorectal cancer, breast cancer, lung cancer and/or pancreatic cancer provided herein can be utilized, e.g., as determined by a medical practitioner, alone or in any combination, in any order, regimen, and/or therapeutic program. Those of skill in the art will further appreciate that advanced treatment options may be appropriate for earlier stage cancers in subjects previously having suffered a cancer.

In some embodiments, methods and compositions for colorectal cancer, breast cancer, lung cancer and/or pancreatic cancer screening provided herein can inform treatment and/or payment (e.g., reimbursement for or reduction of cost of medical care, such as screening or treatment) decisions and/or actions, e.g., by individuals, healthcare facilities, healthcare practitioners, health insurance providers, governmental bodies, or other parties interested in healthcare cost.

In some embodiments, methods and compositions for colorectal cancer, breast cancer, lung cancer and/or pancreatic cancer screening provided herein can inform decision making relating to whether health insurance providers reimburse a healthcare cost payer or recipient (or not), e.g., for (1) screening itself (e.g., reimbursement for screening otherwise unavailable, available only for periodic/regular screening, or available only for temporally- and/or incidentally-motivated screening); and/or for (2) treatment, including initiating, maintaining, and/or altering therapy, e.g., based on screening results. For example, in some embodiments, methods and compositions for colorectal cancer, breast cancer, lung cancer and/or pancreatic cancer screening provided herein are used as the basis for, to contribute to, or support a determination as to whether a reimbursement or cost reduction will be provided to a healthcare cost payer or recipient. In some instances, a party seeking reimbursement or cost reduction can provide results of a screen conducted in accordance with the present specification together with a request for such reimbursement or cost reduction of a healthcare cost. In some instances, a party making a determination as to whether or not to provide a reimbursement or cost reduction of a healthcare cost will reach a determination based in whole or in part upon receipt and/or review of results of a screen conducted in accordance with the present specification.

For the avoidance of any doubt, those of skill in the art will appreciate from the present disclosure that methods and compositions for colorectal cancer, breast cancer, lung cancer and/or pancreatic cancer diagnosis of the present specification are at least for in vitro use. Accordingly, all aspects and embodiments of the present disclosure can be performed and/or used at least in vitro.

Kits

The present disclosure includes, among other things, kits including one or more compositions for use in screening as provided herein, optionally in combination with instructions for use thereof in screening (e.g., screening for a colorectal cancer, breast cancer, lung cancer and/or pancreatic cancer (e.g., early-stage cancer)). In various embodiments, a kit for screening for colorectal cancer, breast cancer, lung cancer and/or pancreatic cancer can include one or more oligonucleotide capture baits (e.g., one or more biotinylated oligonucleotide probes). In certain embodiments, the kit for screening optionally includes one or more bisulfite reagents as disclosed herein. In certain embodiments, the kit for screening optionally includes one or more enzymatic conversion reagents as disclosed herein.

Oligonucleotide capture baits are useful in next generation sequencing (NGS) techniques to target particular regions of interest of DNA. In certain embodiments, one or more capture baits are targeted to capture a region of interest of the DNA corresponding to one or more methylation loci (e.g., methylation loci comprising at least a portion of one or more DMRs, e.g., as found in Tables 14, 7-11 13 and 15).

Oligonucleotide capture baits are intended to enrich the target DNA region, and aid in preparation of a DNA library. The enriched target region will then be sequenced using, for example, an NGS sequencing technique as discussed herein.

In various embodiments, a kit for screening can include one or more of: one or more oligonucleotide primers (e.g., one or more oligonucleotide primer pairs), one or more MSREs, one or more reagents for qPCR (e.g., reagents sufficient for a complete qPCR reaction mixture, including without limitation dNTP and polymerase), and instructions for use of one or more components of the kit for colorectal cancer, breast cancer, lung cancer and/or pancreatic cancer screening. In various embodiments, a kit for screening of colorectal cancer, breast cancer, lung cancer and/or pancreatic cancer can include one or more of: one or more oligonucleotide primers (e.g., one or more oligonucleotide primer pairs e.g., as provided in Tables 3 and 4), one or more bisulfite reagents, one or more reagents for qPCR (e.g., reagents sufficient for a complete qPCR reaction mixture, including without limitation dNTP and polymerase), and instructions for use of one or more components of the kit for colorectal cancer, breast cancer, lung cancer and/or pancreatic cancer screening.

In certain embodiments, a kit of the present disclosure includes at least one oligonucleotide primer pair (e.g., as provided in Tables 3 and 4) for amplification of a methylation locus and/or DMR as disclosed herein (e.g., in Tables 1-4, 7-11, 13 and 15).

In some instances, a kit of the present disclosure includes one or more oligonucleotide primer pairs for amplification of one or more methylation loci of the present disclosure. In some instances, a kit of the present disclosure includes one or more oligonucleotide primer pairs for amplification of one or more methylation loci that are or include all or a portion of one or more genes identified in Tables 1-4, 7-11, 13 and 15. In some particular instances, a kit of the present disclosure includes oligonucleotide primer pairs for a plurality of methylation loci that each are or include all or a portion of a gene identified in Table 1, the plurality of methylation loci including, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 methylation loci, e.g., as provided in Tables 1-4, 7-11 13 and 15.

In some instances, a kit of the present disclosure includes one or more oligonucleotide primer pairs for amplification of one or more DMRs of the present disclosure. In some instances, a kit of the present disclosure includes one or more oligonucleotide primer pairs for amplification of one or more DMRs that are, include all or a portion of, or are within a gene identified in Tables 1-4, 7-11, 13 and 15. In some instances, a kit of the present disclosure includes one or more oligonucleotide primer pairs for amplification of one or more DMRs that are not associated with a presently known gene. In some particular embodiments, a kit of the present disclosure includes oligonucleotide primer pairs for a plurality of DMRs, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 DMRs, e.g., as provided in Tables 1-4, 7-11 13 and 15.

A kit of the present disclosure can further include one or more MSREs individually or in a single solution. In various embodiments, one or more MSREs are selected from the set of MSREs including AciI, Hin6I, HpyCH4IV, and HpaII (e.g., such that the kit includes AciI, Hin6I, and HpyCH4IV, either individually or in a single solution). In certain embodiments, a kit of the present disclosure includes one or more reagents for qPCR (e.g., reagents sufficient for a complete qPCR reaction mixture, including without limitation dNTP and polymerase).

EXAMPLES

The present example includes identification of markers relevant to diagnosis of and/or classification of colorectal cancer, breast cancer, lung cancer and/or pancreatic cancer.
Biomarker Discovery The present Example includes identification of CpG loci that are hypermethylated in one or more of colorectal cancer, breast cancer, lung cancer, and pancreatic cancer as compared to healthy control samples. An initial discovery study included data from The Cancer Genome Atlas (TCGA) Research Network (http://cancergenome.nih.gov/) for colorectal cancer (TCGA-COAD, TCGA-READ), breast cancer (TCGA-BRCA), lung cancer (TCGA-LUAD, TCGA-LUSC), pancreatic cancer (TCGA-PAAD), leukocytes and normal tissue.

For significant marker selection, DNA methylation data from the histologically normal tissues and leukocytes were used to identify CpG methylation sites that lacked tissue-specific DNA methylation (mean b-value <0.25 and b-value >0.3 in no more than five samples across the entire set). From the resulting list of sites, only sites that had a mean b-value difference >0.1 were included. The sites were sorted to determine which sites contributed significantly to separation between normal and cancer samples. The sites were then filtered further based on sorting. As a result of all these filtering steps, 75 breast cancer specific CpG sites, 95 lung cancer specific CpG sites, and 35 pancreatic cancer sites were obtained.

The individual CpG methylation sites serve as markers for cancers as indicated herein. The individual CpG methylation sites are found within the DMRs and loci as described herein.
MSRE-qPCR Validation of Selected Regions The present Example describes an assay for determining the methylation status of colorectal cancer, breast cancer, lung cancer, and pancreatic cancer methylation biomarkers based on circulating cell free DNA (cfDNA). cfDNA is incomplete and fragmented, and the mechanism by which the cfDNA is transmitted from cancer cells to blood (as a portion called circulating tumor DNA) is unknown.

For screening purposes, it is important to allow diagnostic marker detection from a readily obtainable biospecimen, such as blood, urine or stool. Confirming that tissue markers exist in blood, however, is challenging due to low concentration of circulating tumor-derived DNA (0.1-1%) as compared to non-tumor cfDNA background. For blood-based confirmatory testing, Methylation-Sensitive Restriction Enzyme (MSRE)-qPCR technology was utilized. MSRE-qPCR enables detection of <10 copies of targets in highly multiplexed format, making it suitable for use in low tumor derived circulating DNA context. Design of MSRE-qPCR assays is usually less complicated than the design of bisulfite-based assays, as "native" DNA is targeted with no prior chemical alterations required. However, primer selection requires covering a target region (e.g., a DMR) that presents at least one MSRE-cut-site (i.e., an MSRE-cut-site that covers at least one cancer methylation biomarker site, such that cleavage of the MSRE-cut-site is permitted in nucleic acid molecules where all of the at least one cancer methylation biomarker sites are unmethylated and blocked in nucleic acid molecules where at least one of the at least one cancer methylation biomarker sites is methylated).

CpG-rich regions, which are also candidate regions for methylation differences (e.g., as found in, for example, DMRs), are preferred targets for MSRE-qPCR assay design, as they typically contain a large number of MSRE cut-sites and thus normally a high assay development success-rate is expected. Furthermore, the use of more than one MSRE is preferred. In certain embodiments, restriction enzymes including AciI, Hin6I, HpyCH4IV, and HpaII provide a high coverage of CpG-rich sequences. Assays developed to cover tissue-derived CpG targets were then evaluated for their utility for plasma-based marker detection and clinical prediction by using DNA extracted from plasma of patients found to have colorectal cancer, breast cancer, lung cancer, pancreatic cancer and control patients known not to have any cancer-related symptoms.

An exemplary workflow is described herein. As performed in the present example, 4 ml of plasma were collected from plasma samples of 101 patients with colorectal cancer (N=20), breast cancer (N=29), lung cancer (N=37), pancreatic cancer (N=15) and 71 age/gender-matching non-cancer controls using a methylation-sensitive restriction enzyme qPCR approach. Cancer patients who had received curative treatment prior to blood collection were excluded from the study. The non-cancer patients had no clinical symptoms of cancer at the time of recruitment. The sample cohort is further described in Table 5.

cfDNA from plasma samples was extracted with QIAamp MinElute ccfDNA Kit for manual isolation of the samples following protocol defined by manufacturer (QIAamp MinElute ccfDNA Handbook 08/2018, Qiagene).

One-third of the eluted cfDNA volume was directly used for PCR amplification of the target regions and consecutive uQPCR analysis. This reaction functions as a quality control, showing whether a target of interest is detectable and quantifiable from plasma in its native DNA format. The remaining two thirds of the initially eluted cfDNA volume were used for digestion with methylation specific restriction enzymes. MSRE-qPCR assays of the present Examples utilize the MSREs AciI, Hin6I, and HpyCH4IV, which together were found to provide sufficient coverage.

MSRE-qPCR oligonucleotide primer pairs as described herein were successfully developed for amplification of DMRs. DMRs included 1-15 MSRE cut-sites per target to enrich for the methylation-derived signal. Methylation sensitive restriction enzymes detected unmethylated DNA regions. Application of the MSRE enzymes resulted in the digestion and elimination of the unmethylated DNA strand(s) from the sample. The remaining the methylated regions of DNA (e.g., methylated loci including DMRs) were left intact and quantifiable.

TABLE 5

Characteristics for sample cohort used in this study, indicating samples used in (i) the Pilot cohort for initial marker evaluation and prediction model development and (ii) the Validation cohort samples that were used for prediction algorithm validation

| Characteristics | Control (n = 71) | Colorectal Cancer (n = 20) | Pancreatic Cancer (n = 15) | Lung Cancer (n = 30) | Breast Cancer (n = 29) |
|---|---|---|---|---|---|
| Age (years, average (IQR)) | 60 (32-78) | 59 (28-77) | 60 (50-71) | 59 (42-75) | 57 (41-77) |
| Gender (n (%)) | | | | | |
| Female | 36 (51%) | 10 (50%) | 7 (47%) | 12 (32%) | 29 (100%) |
| Male | 35 (49%) | 10 (50%) | 8 (53%) | 25 (68%) | |
| Stage | | | | | |
| Stage I | | 6 | | 15 | 7 |
| Stage II | | 9 | | 4 | 8 |
| Stage III | | 5 | 15 | 17 | 13 |
| Unknown | | | | 1 | 1 |

The qPCR cycle threshold (CT) values were used for the consecutive data analyses. Data normalization was performed by calculating the delta-ct (dCT) value for each marker by subtracting for each marker the CT-value of undigested reaction from the CT-value of digested reaction. The R version 3.3.2 software was used for data analysis.

Pan-cancer detection assay was built in a 2-step classification tree method. In detail, a first level of decision making was implemented to separate control patients from cancer patients, regardless of the cancer location. In the current Example, control patients were used as a reference point. For the first level decision making process, the potential of the methylation markers were evaluated by first ranking the features by using random forest (RF) classification algorithm using Monte-Carlo cross-validation over 50-runs on cancer vs control group. Features with variance of importance (VIP) >2 were then further used for classification model building and testing of the algorithm.

2nd level of decision making was intended for establishing, from which pre-defined tissue the detected cancer could have originated. In this random forest, decision tree building was utilized for comparing 4 cancer types against each other. Decision trees were built in a multi-group setting where each cancer type was compared against the other 3 (e.g., colorectal cancer vs combined lung, breast and pancreatic cancer or lung cancer vs colorectal, breast and pancreatic cancer). 500 Random Forest trees were run for finding the most optimal marker-set that gives lowest out-of-bag (OOB) error, which in return means highest separation between multiple groups that are different cancer types. Accuracy for correct cancer type identification was defined as the fraction of each cancer sample falling under correct, pre-defined cancer type.

Results

As shown in the below table, accuracy was defined as the fraction of correct calls (e.g., the fraction correctly identified as cancer). Specificity indicates an ability to separate control (e.g., non-cancer) patients correctly from all cancer patients. Sensitivity indicates an ability to separate cancer patients from control (e.g., non-cancer) patients.

Random forest cross-validation analysis revealed that with 3 markers an area under curve (AUC) of 76% can be achieved. Increasing the number of markers in a panel to 30 methylation markers (e.g., Table 11) showed pan-cancer detection potential with AUC of 90%, where sensitivity of detecting cancer of any origin was 78% at 87% specificity (Table 6), with 100% of the pancreatic cancer (15/15), 95% of the CRC (19/20), 72% of the breast cancer (21/29) and 65% of lung cancer (24/37) correctly identified as cancer patients. Sensitivity for stage I cancers was 61% (17/28), sensitivity for stage II cancers 67% (14/21) and stage III cancers 92% (46/50) correctly identified.

TABLE 6

Prediction algorithm accuracy estimates according to different marker-combinations for Cancer (colorectal + breast + lung + pancreatic) vs control group

|  | 3 | 5 | 9 | 17 | 30 |
|---|---|---|---|---|---|
| AUC | 0.76 | 0.80 | 0.85 | 0.88 | 0.90 |
| AUC_CI_LOW | 0.74 | 0.78 | 0.84 | 0.87 | 0.89 |
| AUC_CI_HIGH | 0.77 | 0.81 | 0.86 | 0.89 | 0.91 |
| Sensitivity | 0.68 | 0.71 | 0.73 | 0.75 | 0.78 |
| Specificity | 0.71 | 0.74 | 0.81 | 0.85 | 0.87 |
| Accuracy | 0.69 | 0.72 | 0.76 | 0.78 | 0.79 |
| Kappa | 0.36 | 0.41 | 0.49 | 0.55 | 0.57 |

Marker panels showing the best predictive performances can be seen in Tables 7-11.

TABLE 7

3-marker combination

| Gene | chr | start | end | width | annotations | Sequence |
|---|---|---|---|---|---|---|
| HOXA7 | 7 | 27156273 | 27156352 | 80 | HOXA7 | CCCGGGGATGTTTTGG TCGTAGGAGGCGCAG GGCAGGTTGCCGTAGG CGTCGGCGCCCAGGCC GTAGCCGGACGCAAA GG (SEQ ID NO: 91) |

TABLE 7-continued 3-marker combination

| Gene | chr | start | end | width | annotations | Sequence |
|---|---|---|---|---|---|---|
| NA | 10 | 100830555 | 100830658 | 104 | NA | AGCGGCTGAAATTGGT GCGCCTTGTGCTGTGG TCTGGGTGTGTCCCGG AGAGGGCGCGCAGGC GCCTATGTCTGTCGCG GGGCGGTCGGCGGGTT CCTGCATAG (SEQ ID NO: 96) |
| JAM2 | 21 | 25640320 | 25640399 | 80 | JAM2 | CCGCGTGGTCTGGGCT CTGTAGCGTCCCAGCT GAGCCGGCGATATGC AGCGCACTTGTGGGGC GGAGGTGGAGGGAAT TC (SEQ ID NO: 108) |

TABLE 8

5-marker combination

| Gene | chr | start | end | width | Sequence |
|---|---|---|---|---|---|
| KLK10 | 19 | 51019613 | 51019705 | 93 | GCAGGTAGCTTCACCTGGGAGTCGCCG ATAGGAAGGAGGGAGGGGACCCAGAC GTGCCTCTGCCCTGCCTGTGGTCTGCC CTGGTATCCTCT (SEQ ID NO: 83) |
| HOXA7 | 7 | 27156291 | 27156403 | 113 | GTAGGAGGCGCAGGGCAGGTTGCCGTA GGCGTCGGCGCCCAGGCCGTAGCCGGA CGCAAAGGGGCTCTGATAAAGGGGGCT GTTGACATTGTATAAGCCCGGAACGGT CGAGG (SEQ ID NO: 92) |
| NA | 10 | 100830555 | 100830658 | 104 | AGCGGCTGAAATTGGTGCGCCTTGTGC TGTGGTCTGGGTGTGTCCCGGAGAGGG CGCGCAGGCGCCTATGTCTGTCGCGGG GCGGTCGGCGGGTTCCTGCATAG (SEQ ID NO: 96) |
| TXNRD1 | 12 | 104215675 | 104215784 | 110 | GGCTATGACTTCGCTGTTGTCACCGAG CGCCCCGCCCACCGCGTTCTCCGACCC GCGGCCGGCAGGGGGCTCGCGGCCTCC GCCAGGCGTCCTTCGGCTCCGTCAGTTC C (SEQ ID NO: 99) |
| THBD | 20 | 23049354 | 23049500 | 147 | TCTGACTGGCATTGAGGAAGGTCGCGG GGCCCGGGTAGAGCGCGAAGCAGTCGT GCTCGACGCACTGGCTGCCACCCGGCT GCGGCTCTGCGGGTGCGGGGAACCCCA GGCCGGCCAGGGCCAGCGCGCCAAGG ACCAGGACCCAA (SEQ ID NO: 107) |

TABLE 9

9-marker combination

| Gene | chr | start | end | width | Sequence |
|---|---|---|---|---|---|
| HOXD8 | 2 | 176129896 | 176130001 | 106 | GGGGTTTGTAAACCGAGG CCAGAGTGTCCCCGTGGG CCGAGCGCACTTTTTTCTT GTCCGGGTGCGCTCAGTC ACTGGTGCCTGAGAGGAA ACAGTGGAGGCAGCG (SEQ ID NO: 84) |
| SCGN | 6 | 25652114 | 25652232 | 119 | CCCCAAAGCGCAGAGACA GACAGGATCTGCCAGGAC AGCGCGCAGGGCGGGGCG GGGACAGGCGCGCCAGGA |

TABLE 9-continued 9-marker combination

| Gene | chr | start | end | width | Sequence |
|---|---|---|---|---|---|
| | | | | | GCGGGGCGGGCTTCCAGC CGCTGGTTTTGCTGAGGGC TGAGGGACG (SEQ ID NO: 89) |
| HOXA7 | 7 | 27156291 | 27156403 | 113 | GTAGGAGGCGCAGGGCAG GTTGCCGTAGGCGTCGGC GCCCAGGCCGTAGCCGGA CGCAAAGGGGCTCTGATA AAGGGGGCTGTTGACATT GTATAAGCCCGGAACGGT CGAGG (SEQ ID NO: 92) |
| MIR196B | 7 | 27169630 | 27169719 | 90 | CCAAGGAGAGAACCCTGC CATCGCGCCTGGCCCGGC CCAGCCCAGCCCCTAGGC AACCTGCGCCCGCCAGTG CAACAGAGTGCCCCAGGC (SEQ ID NO: 93) |
| NA | 10 | 100830555 | 100830658 | 104 | AGCGGCTGAAATTGGTGC GCCTTGTGCTGTGGTCTGG GTGTGTCCCGGAGAGGGC GCGCAGGCGCCTATGTCT GTCGCGGGGCGGTCGGCG GGTTCCTGCATAG (SEQ ID NO: 96) |
| TXNRD1 | 12 | 104215675 | 104215784 | 110 | GGCTATGACTTCGCTGTTG TCACCGAGCGCCCCGCCC ACCGCGTTCTCCGACCCGC GGCCGGCAGGGGGCTCGC GGCCTCCGCCAGGCGTCCT TCGGCTCCGTCAGTTCC (SEQ ID NO: 99) |
| HAPLN3 | 15 | 88895676 | 88895781 | 106 | GTCTCCAGACTCGCTGGG AACCACCGCAAAGAGGGT GTGCAAGAGTTGAGGCCC TCACGTCTTGGGAAAGGA GAGTAGGGGTGGAATAGG AGAGTTTGGGGAGGGG (SEQ ID NO: 100) |
| THBD | 20 | 23049354 | 23049500 | 147 | TCTGACTGGCATTGAGGA AGGTCGCGGGGCCCGGGT AGAGCGCGAAGCAGTCGT GCTCGACGACTGGCTGC CACCCGGCTGCGGCTCTGC GGGTGCGGGGAACCCCAG GCCGGCCAGGGCCAGCGC GCCAAGGACCAGGACCCC AA (SEQ ID NO: 107) |
| SDC2 | 8 | 96493985 | 96494062 | 78 | CTTCAGAGCAGCCTTCC CGGAGCACCAACTCCGTG TCGGGAGTGCAGAAACCA ACAAGTGAGAGGGCGCCG CGTTC (SEQ ID NO: 109) |

TABLE 10

17-marker combination

| Gene | chr | start | end | width | Sequence |
|---|---|---|---|---|---|
| MAST1 | 19 | 12867716 | 12867820 | 105 | CCCCCTCCATGCAGCA AGCGATTCTCCGCGTC CGAGGCCACTTTTCCTG GAGGGAGAGGCCAGTC |

TABLE 10-continued 17-marker combination

| Gene | chr | start | end | width | Sequence |
|---|---|---|---|---|---|
| | | | | | CCCCTTTGGGCGCCCG CCGCCGTTTCTCGGCGC TGCTGGAG (SEQ ID NO: 82) |
| HOXD8 | 2 | 176129896 | 176130001 | 106 | GGGGTTTGTAAACCGA GGCCAGAGTGTCCCCG TGGGCCGAGCGCACTT TTTTCTTGTCCGGGTGC GCTCAGTCACTGGTGC CTGAGAGGAAACAGTG GAGGCAGCG (SEQ. ID NO: 84) |
| PREX1 | 20 | 48828337 | 48828448 | 112 | TCACCGCGGGCTACGC CACTCCCACCCGGCAC ACGCGACACCCGCCGC GCGCAGGCTCCTGCTT GCAGGTCCGGCCGCTG CTCGGGCCAAGTAAAC ACCGGGCTGGGAAAGC (SEQ ID NO: 86) |
| AMOTL2 | 3 | 134364403 | 134364512 | 110 | CCATGGCTTCCTTTCTT TGGCAGAGTCAGGCTC CAGAAGTCCGCCTTCC TCCACAGGCACCC TAATCTGCCGTGCCCTT GCAGCTTCTCCTCCCCA GACTCCTCAGGGAA (SEQ ID NO: 87) |
| SCGN | 6 | 25652114 | 25652232 | 119 | CCCCAAAGCGCAGAGA CAGACAGGATCTGCCA GGACAGCGCGCAGGGC GGGGCGGGGACAGGCG CGCCAGGAGCGGGGCG GGCTTCCAGCCGCTGG TTTTGCTGAGGGCTGA GGGACG (SEQ ID NO: 89) |
| HOXA7 | 7 | 27155916 | 27156027 | 112 | TCGAACCCATTAATTG GGCCATAAAAAGTTTT ATGAGCCTCATTTACAT ACAATGCTATGGGCTC CACGCAATGGCGCCTC CGCTCCAATTAAAACC AGAAAGGCTGCGCCG (SEQ ID NO: 90) |
| MIR196B | 7 | 27169630 | 27169719 | 90 | CCAAGGAGAGAACCCT GCCATCGCGCCTGGCC CGGCCCAGCCCAGCCC CTAGGCAACCTGCGCC CGCCAGTGCAACAGAG TGCCCCAGGC (SEQ ID NO: 93) |
| TNFRSF10D | 8 | 23163949 | 23164031 | 83 | GGTGGATCGAAAGCGC CAAAAATCAATCAGAA ATCGTCCCCGTAGTTTG TGCGCGTGCAAAGGTT CTCGCAGCTACACTGC CA (SEQ ID NO: 94) |
| NA | 10 | 100830555 | 100830658 | 104 | AGCGGCTGAAATTGGT GCGCCTTGTGCTGTGGT CTGGGTGTGTCCCGGA GAGGGCGCGCAGGCGC CTATGTCTGTCGCGGG GCGGTCGGCGGGTTCC TGCATAG (SEQ ID NO: 96) |

TABLE 10-continued

17-marker combination

| Gene | chr | start | end | width | Sequence |
|---|---|---|---|---|---|
| TXNRDI | 12 | 104215675 | 104215784 | 110 | GGCTATGACTTCGCTGT TGTCACCGAGCGCCCC GCCCACCGCGTTCTCC GACCCGCGGCCGGCAG GGGGCTCGCGGCCTCC GCCAGGCGTCCTTCGG CTCCGTCAGTTCC (SEQ ID NO: 99) |
| HAPLN3 | 15 | 88895676 | 88895781 | 106 | GTCTCCAGACTCGCTG GGAACCACCGCAAAGA GGGTGTGCAAGAGTTG AGGCCCTCACGTCTTG GGAAGGAGAGTAGG GGTGGAATAGGAGAGT TTGGGAGGGG (SEQ ID NO: 100) |
| CYBA | 16 | 88651139 | 88651205 | 67 | CATCTGTAGGGTGCAG GGCTGTCCCGGAGCCT TCTGCCCCCGCCCTCTC TAGCCACGCCGAGGCA TA (SEQ ID NO: 101) |
| ZNF582 | 19 | 56393606 | 56393725 | 120 | TCCGGGAACATAGTC TTTAGGCGTAAAGGCA GCAGCCCGGCCTTGAA GCCGGATCTCGCGATG TTTCAGGGTGAGCCGG ACGCAGGCGTGCCTGC GCAGTGCGCGGAGGAG TGCTGTTC (SEQ ID NO: 103) |
| THBD | 20 | 23049354 | 23049500 | 147 | TCTGACTGGCATTGAG GAAGGTCGCGGGGCCC GGGTAGAGCGCGAAGC AGTCGTGCTCGACGCA CTGGCTGCCACCCGGC TGCGGCTCTGCGGGTG CGGGGAACCCCAGGCC GGCCAGGGCCAGCGCG CCAAGGACCAGGACCC CAA (SEQ ID NO: 107) |
| SDC2 | 8 | 96493985 | 96494062 | 78 | CTTCAGAGAGCAGCCT TCCCGGAGCACCAACT CCGTGTCGGGAGTGCA GAAACCAACAAGTGAG AGGGCGCCGCGTTC (SEQ ID NO: 109) |
| FGF14 | 13 | 102394577 | 102394651 | 75 | CAACGGAAACTTCCCG CGCTACGGCGGCTCCA ACGGGCCGCTTCCGCC GCATTGCGTAGCGAAG CCCCCGGCGAG (SEQ ID NO: 110) |
| CDKN2A | 9 | 21970919 | 21971017 | 99 | GCATCTATGCGGGCAT GGTTACTGCCTCTGGTG CCCCCCGCAGCCGCGC GCAGGTACCGTGCGAC ATCGCGATGGCCCAGC TCCTCAGCCAGGTCCA CG SEQ ID NO: 111) |

TABLE 11

| | | | | | |
|---|---|---|---|---|---|
| 30-marker combination | | | | | |
| Gene | chr | start | end | width | Sequence |
| MAST1 | 19 | 12867716 | 12867820 | 105 | CCCCCTCCATGCAGCAAGCGATTCTCCGCGTCCGAGGCCAGTTTCCTGGAGGGAGAGGCCAGTCCCCCTTTGGGCGCCCGCCGCCGTTTCTCGGCGCTGCTGGAG (SEQ ID NO: 82) |
| KLK10 | 19 | 51019613 | 51019705 | 93 | GCAGGTAGCTTCACCTGGGAGTCGCCGATAGGAAGGAGGGAGGGGACCCAGACGTGCCTCTGCCCTGCCTGTGGTCTGCCGCTGGTATCCTCT (SEQ ID NO: 83) |
| HOXD8 | 2 | 176129896 | 176130001 | 106 | GGGGTTTGTAAACCGAGGCCAGAGTGTCCCCGTGGGCCGAGCGCACTTTTTTCTTGTCCGGGTGCGCTCAGTCACTGGTGCCTGAGAGGAAACAGTGGAGGCAGCG (SEQ ID NO: 84) |
| C2orf88 | 2 | 190180554 | 190180682 | 129 | GCCGGCAGCTGCTTGGTAGTTGCGGGGGCGTGAGGGCGGTGGCCCAGACCAACCGGCTGGCAGCCCAGCTCCGCTCCGCCCGCCCCTGCCTCGGACCCTGCGCCTGAGGAAGTATCGAGGCAACCCTC (SEQ ID NO: 85) |
| PREX1 | 20 | 48828337 | 48828448 | 112 | TCACCGCGGGCTACGCCACTCCCACCCGGCACACGCGACACCCGCCGCGCGCAGGCTCCTGCTTGCAGGTCCGGCCGCTGCTCGGGCCAAGTAAACACCGGGCTGGGAAAGC (SEQ ID NO: 86) |
| AMOTL2 | 3 | 134364403 | 134364512 | 110 | CCATGGCTTCCTTTCTTTGGCAGAGTCAGGCTCCAGAAGTCCGCCTTCCTCCACAGGCACCCTAATCTGCCGTGCCCTTGCAGCTTCTCCTCCCCAGACTCCTCAGGGAA (SEQ ID NO: 87) |
| SOX2OT | 3 | 181719490 | 181719596 | 107 | GGCAAATTGAGGCCGAGCTGACGAGCTCCGGCGGGTGGACCTGACGTCACCGCGGCCCGGGTCACCTCACCCATGGGCTCCCCAAGAAGGTGCTGTGTGGGCTCG (SEQ ID NO: 88) |
| SCGN | 6 | 25652114 | 25652232 | 119 | CCCCAAAGCGCAGAGACAGACAGGATCTGCCAGGACAGCGCGCAGGGCGGGGCGGGACAGGCGCGCCAGGAGCGGGGCGGGCTTCCAGCCGCTGGTTTTGCTGAGGGCTGAGGGACG (SEQ ID NO: 89) |
| HOXA7 | 7 | 27155916 | 27156027 | 112 | TCGAACCCATTAATTGGGCCATAAAAAGTTTTATGAGCCTCATTTACA |

TABLE 11-continued

30-marker combination

| Gene | chr | start | end | width | Sequence |
|---|---|---|---|---|---|
| | | | | | TACAATGCTATGGGCTCCACGCAATGGCGCCTCCGCTCCAATTAAAACCAGAAAGGCTGCGCCG (SEQ ID NO: 90) |
| HOXA7 | 7 | 27156273 | 27156352 | 80 | CCCGGGGATGTTTTGGTCGTAGGAGGCGCAGGGCAGGTTGCCGTAGGCGTCGGCGCCCAGGCCGTAGCCGGACGCAAAGG (SEQ ID NO: 91) |
| HOXA7 | 7 | 27156291 | 27156403 | 113 | GTAGGAGGCGCAGGGCAGGTTGCCGTAGGCGTCGGCGCCCAGGCCGTAGCCGGACGCAAAGGGGCTCTGATAAAGGGGGCTGTTGACATTGTATAAGCCCGGAACGGTCGAGG (SEQ ID NO: 92) |
| MIR196B | 7 | 27169630 | 27169719 | 90 | CCAAGGAGAGAACCCTGCCATCGCGCCTGGCCCGGCCCAGCCCAGCCCCTAGGCAACCTGCGCCCGCCAGTGCAACAGAGTGCCCCAGGC (SEQ ID NO: 93) |
| TNFRSF10D | 8 | 23163949 | 23164031 | 83 | GGTGGATCGAAAGCGCCAAAAATCAATCAGAAATCGTCCCCGTAGTTTGTGCGCGTGCAAAGGTTCTCGCAGCTACACTGCCA (SEQ ID NO: 94) |
| TNFRSF10D | 8 | 23163995 | 23164099 | 105 | TTGTGCGCGTGCAAAGGTTCTCGCAGCTACACTGCCAGAATAGAACGTGCTCCTCCGCTTTTATACCCCGGAAAAAAGGCGTGGTCAGTTGTACTCCCTTCCCGC (SEQ ID NO: 95) |
| NA | 10 | 100830555 | 100830658 | 104 | AGCGGCTGAAATTGGTGCGCCTTGTGCTGTGGTCTGGGTGTGTCCCGGAGAGGGCGCGCAGGCGCCTATGTCTGTCGCGGGGCGGTCGGCGGGTTCCTGCATAG (SEQ ID NO: 96) |
| ME3 | 11 | 86672189 | 86672296 | 108 | AGATCCGGTGCGGGTGACAGCCGGCGCCACCCCTGCCCCCATCCCTGTGAAAAAGAGGCGACTGCGCGGCGAGGGGTCCCCGTACCCCTAATCCCGCGTGGTGGCTTG (SEQ ID NO: 97) |
| ME3 | 11 | 86672338 | 86672429 | 92 | GAGCTGAGGTCTACGCGGTCCCGCTGCGGAGCAGGCGGGGTGAGGAGCTGCGGTCTGTGAGTCCTCTCCCGCCAATGGGTGGACCGCGCTGG (SEQ ID NO: 98) |
| TXNRD1 | 12 | 104215675 | 104215784 | 110 | GGCTATGACTTCGCTGTTGTCACCGAGCGCCCCGCCCACCGCGTTCTCCGACCCGCGGCCGGC |

TABLE 11-continued

30-marker combination

| Gene | chr | start | end | width | Sequence |
|---|---|---|---|---|---|
| | | | | | AGGGGGCTCGCGGCCT CCGCCAGGCGTCCTTC GGCTCCGTCAGTTCC (SEQ ID NO: 99) |
| HAPLN3 | 15 | 88895676 | 88895781 | 106 | GTCTCCAGACTCGCTG GGAACCACCGCAAAG AGGGTGTGCAAGAGTT GAGGCCCTCACGTCTT GGGAAAGGAGAGTAG GGGTGGAATAGGAGA GGTTTGGGGAGGGG (SEQ ID NO: 100) |
| CYBA | 16 | 88651139 | 88651205 | 67 | CATCTGTAGGGTGCAG GGCTGTCCCGGAGCCT TCTGCCCCGCCCTCT CTAGCCACGCCGAGGC ATA (SEQ ID NO: 101) |
| ZNF568 | 19 | 36916284 | 36916453 | 170 | TGTGTTCTGGCCGGAA GTTGAGTGGGGCCGCG GGGCCTGCTGGGAGGT GTTGTCCTCGGAAACG TCGCTGGCGCGGAGG GATGGTTCGGCGCTTT AGGCGTCTGTCACAGA CCTATCTGCGGGTCGC CTTCACCC AGCATCTCAGAAACTG CGCGCGGGATGAACA TTCG (SEQ ID NO: 102) |
| ZNF582 | 19 | 56393606 | 56393725 | 120 | TCCGGGAAACATAGTC TTTAGGCGTAAAGGCA GCAGCCCGGCCTTGAA GCCGGATCTCGCGATG TTTCAGGGTGAGCCGG ACGCAGGCGTGCCTGC GCAGTGCGCGGAGGA GTGCTGTTC (SEQ ID NO: 103) |
| ZNF471 | 19 | 56507527 | 56507675 | 149 | CCCCACGCGTACTCAC ACCGAAGGCTCAGCC GTCGCGCGTTTCCCTC CCAGGCCCCAGGAACT AGTAACTAGGGACGCT TCTGGTCTCTAGGCGA GGAGAGGGGAGAGC GCAATCTTTGCGCCTG CGCACACTCCTGCTCT TACCCGC (SEQ ID NO: 104) |
| ZNF471 | 19 | 56507558 | 56507675 | 118 | GTCGCGCGTTTCCCTC CCAGGCCCCAGGAACT AGTAACTAGGGACGCT TCTGGTCTCTAGGCGA GGAGAGGGGAGAGC GCAATCTTTGCGCCTG CGCACACTCCTGCTCT TACCCGC (SEQ ID NO: 105) |
| ZNF471 | 19 | 56507662 | 56507750 | 89 | CTGCTCTTACCCGCCG GAACCCTGGGCCACGC CCGGCTCGCGTAATCA CGCACTGCGCAGGCAC CGCCCGCTCTGCTCTA AGGTCCCTC (SEQ ID NO: 106) |
| THBD | 20 | 23049354 | 23049500 | 147 | TCTGACTGGCATTGAG GAAGGTCGCGGGGCC CGGGTAGAGCGCGAA |

TABLE 11-continued

30-marker combination

| Gene | chr | start | end | width | Sequence |
|---|---|---|---|---|---|
| | | | | | GCAGTCGTGCTCGACG CACTGGCTGCCACCCG GCTGCGGCTCTGCGGG TGCGGGGAACCCCAG GCCGGCCAGGGCCAG CGCGCCAAGGACCAG GACCCCAA (SEQ ID NO: 107) |
| JAM2 | 21 | 25640320 | 25640399 | 80 | CCGCGTGGTCTGGGCT CTGTAGCGTCCCAGCT GAGCCGGCGATATGC AGCGCACTTGTGGGGC GGAGGTGGAGGGAAT TC (SEQ ID NO: 108) |
| SDC2 | 8 | 96493985 | 96494062 | 78 | CTTCAGAGAGCAGCCT TCCCGGAGCACCAACT CCGTGTCGGGAGTGCA GAAACCAACAAGTGA GAGGGCGCCGCGTTC (SEQ ID NO: 109) |
| FGF14 | 13 | 102394577 | 102394651 | 75 | CAACGGAAACTTCCCG CGCTACGGCGGCTCCA ACGGGCCGCTTCCGCC GCATTGCGTAGCGAAG CCCCCGGCGAG (SEQ ID NO: 110) |
| CDKN2A | 9 | 21970919 | 21971017 | 99 | GCATCTATGCGGGCAT GGTTACTGCCTCTGGT GCCCCCCGCAGCCGCG CGCAGGTACCGTGCGA CATCGCGATGGCCCAG CTCCTCAGCCAGGTCC ACG (SEQ ID NO: 111) |

Individual marker accuracy values are represented in FIGS. 1A-DD as box-plots. FIGS. 1A-DD show detection of methylated markers in plasma. dCt values are plotted for 30 markers for control samples (CNT) and cancer (colorectal, breast, lung, pancreatic) samples (Cancer)

Cancer Location Analysis

Cases that were correctly separated from control group were further evaluated to identify their tissue of origin. A 7 methylation marker panel allowed correct assignment of the tissue of origin to 58% of colorectal cancer (11/19), 71% of lung cancer (17/24), 53% of pancreatic cancer (8/15) and 62% of breast cancer (13/21) cases (Table 12).

TABLE 12

OOB matrix indicating sample classification according to a 7-marker panel. Entries found on the bold, diagonal indicates a correctly classified sample. For example, 13 breast cancer samples were correctly identified as originating from breast cancer tissue samples. Entries in rows indicate false identifications to other cancer types. For example, two breast cancer tissue samples were incorrectly identified as lung cancer samples. BC—breast cancer, CRC—colorectal cancer, LC—lung cancer, PC—pancreatic cancer

| | BC | CRC | LC | PC | class.error | Correct |
|---|---|---|---|---|---|---|
| BC | 13 | 1 | 4 | 3 | 0.381 | 62 |
| CRC | 2 | 11 | 8 | 0 | 0.421 | 58 |
| LC | 1 | 4 | 17 | 2 | 0.292 | 71 |
| PC | 4 | 1 | 2 | 8 | 0.467 | 53 |

Individual markers contributing to the best performing panel are listed in Table 13.

TABLE 13

| 7-marker combination | | | | | |
|---|---|---|---|---|---|
| annotations | chr | start | end | Width | sequence |
| HOXA7 | 7 | 27155916 | 27156027 | 112 | TCGAACCCATTAATTGGGCCATAAAAGTTTTATGAGCCTCATTTACATACAATGCTATGGGCTCCACGCAATGGCGCCTCCGCTCCAATTAAAACCAGAAAGGCTGCGCCG (SEQ ID NO: 90) |
| MIR196B | 7 | 27169630 | 27169719 | 90 | CCAAGGAGAGAACCCTGCCATCGCGCCTGGCCCGGCCCAGCCCAGCCCCTAGGCAACCTGCGCCCGCCAGTGCAACAGAGTGCCCCAGGC (SEQ ID NO: 93) |
| TNFRSF10D | 8 | 23163995 | 23164099 | 105 | TTGTGCGCGTGCAAAGGTTCTCGCAGCTACACTGCCAGAATAGAACGTGCTCCTCCGCTTTTATACCCCGGAAAAAAGGCGTGGTCAGTTGTACTCCCTTCCCGC (SEQ ID NO: 95) |
| DNM3 | 1 | 171841774 | 171841857 | 84 | CAGAGCGCCGGCAAGAGCTCGGTGCTCGAGAACTTCGTGGGCAGGTAAGCGCGCAGGGCGCGGAGTAAGGATGCGGCAGTGGGG (SEQ ID NO: 112) |
| C1orf230 | 1 | 151721583 | 15172167 | 97 | TTAGCGCAGCGCAGCTGGAGCAGCTGCGAAAATTCAAGGTGGGTGCGCCCGCGCCCCCATCCAGCGTCCACCAAAGTGTAGCTGCCCCAGGACTGGG (SEQ ID NO: 115) |
| ZNF568 | 19 | 36916252 | 36916371 | 120 | GCCCAAGCCTCACCCTCACACAGGAAAGCAGATGTGTTCTGGCCGGAAGTTGAGTGGGCCGCGGGGCCTGCTGGGAGGTGTTGTCCTCGGAAACGTCGCTGGCGCGGAGGGATGGTTCG (SEQ ID NO: 118) |
| C9orf50 | 9 | 129620787 | 129620870 | 84 | AGAGTAGCCAATTTGGGGGTTGCTGTGACGTTTAAATGAGCAAGTACATGCCAGTCTTAGAACAGCAAGCTCGGTACAGTGCC (SEQ ID NO: 119) |

A 14 methylation marker panel (Table 15) allowed correct assignment of the tissue of origin to 74% of colorectal cancer (14/19), 79% of lung cancer (19/24), 53% of pancreatic cancer (9/15) and 52% of breast cancer (11/21) cases. (Table 14).

TABLE 14

OOB matrix indicating sample classification according to 14-marker panel. Diagonal line indicates the correct classification and rows indicate false identifications to other cancer types. BC—breast cancer, CRC—colorectal cancer, LC—lung cancer, PC—pancreatic cancer

|     | BC | CRC | LC | PC | class.error | Correct |
|-----|----|----|----|----|-------------|---------|
| BC  | 11 | 0  | 6  | 4  | 0.476       | 52      |
| CRC | 0  | 14 | 3  | 2  | 0.263       | 74      |

TABLE 14-continued

OOB matrix indicating sample classification according to 14-marker panel. Diagonal line indicates the correct classification and rows indicate false identifications to other cancer types. BC—breast cancer, CRC—colorectal cancer, LC—lung cancer, PC—pancreatic cancer

|     | BC | CRC | LC | PC | class.error | Correct |
|-----|----|-----|----|----|-------------|---------|
| LC  | 0  | 3   | 19 | 2  | 0.208       | 79      |
| PC  | 4  | 1   | 1  | 9  | 0.4         | 60      |

Individual markers contributing to a 14-methylation maker panel are listed in Table 15.

TABLE 15

14-marker combination

| annotations | chr | start | end | Width | sequence |
|---|---|---|---|---|---|
| DNM3 | 1 | 171841774 | 171841857 | 84 | CAGAGCGCCGGCAAG AGCTCGGTGCTCGAG AACTTCGTGGGCAGG TAAGCGCGCAGGGCG CGGAGTAAGGATGCG GCAGTGGGG (SEQ ID NO: 112) |
| NA | 5 | 73436635 | 73436710 | 76 | CAGGCTGGGCGGTCT TTGACCCCCGCGCCT CCCGCCCACAGCCGG AGCCCGGCAGCTGGA AGCACCCGCTACCCC (SEQ ID NO: 113) |
| HOXA7 | 7 | 27155916 | 27156027 | 112 | TCGAACCCATTAATT GGGCCATAAAAAGTT TTATGAGCCTCATTTA CATACAATGCTATGG GCTCCACGCAATGGC GCCTCCGCTCCAATTA AAACCAGAAAGGCTG CGCCG (SEQ ID NO: 90) |
| MIR196B | 7 | 27169630 | 27169719 | 90 | CCAAGGAGAGAACCC TGCCATCGCGCCTGG CCCGGCCCAGCCCAG CCCCTAGGCAACCTG CGCCCGCCAGTGCAA CAGAGTGCCCCAGGC (SEQ ID NO: 93) |
| DLX6-AS1 | 7 | 97014186 | 97014266 | 81 | CAAGACCTGGCGCAT CTTTGCAAATTACAG ATAATTGTAAACGTC CAGATTATGATAATA GCATCCTAATCCAGC CTGCAA (SEQ ID NO: 114) |
| TNFRSF10D | 8 | 23163995 | 23164099 | 105 | TTGTGCGCGTGCAAA GGTTCTCGCAGCTAC ACTGCCAGAATAGAA CGTGCTCCTCCGCTTT TATACCCCGGAAAAA AGGCGTGGTCAGTTG TACTCCCTTCCCGC (SEQ ID NO: 95) |
| C1orf230 | 1 | 151721583 | 151721679 | 97 | TTAGCGCAGCGCAGC TGGAGCAGCTGCGAA AATTCAAGGTGGGTG CGCCCGCGCCCCCAT |

TABLE 15-continued

14-marker combination

| annotations | chr | start | end | Width | sequence |
|---|---|---|---|---|---|
| | | | | | CCAGCGTCCACCAAA GTGTAGCTGCCCCAG GACTGGG (SEQ ID NO: 115) |
| DIO3OS, MIR1247 | 14 | 101561395 | 101561505 | 111 | TCCGGGCTCAAGTTG CAAGGGGCGGGCCG GGCCGGAGGTGGAGT CTCCCGCCAATTGAA GCCTCCGCTATAAATT GAACTCCCTGCACTG CTGAAGCCCAGATGC CTCGC (SEQ ID NO: 116) |
| GSG1L | 16 | 28063861 | 28063964 | 104 | CCGAAAGAAATCCGA GCCAGGGTGAGGGTC TGAGACGCAAGGAGA ATCCCAG GCAAGGCGCTCCTGA GAAAAGATCCCCACG GCGGACGTGGGGCA CAAAACC (SEQ ID NO: 117) |
| ZNF568 | 19 | 36916252 | 36916371 | 120 | GCCCAAGCCTCACCC TCACACAGGAAAGCA GATGTGTTCTGGCCG GAAGTTGAGTGGGGC CGCGGGGCCTGCTGG GAGGTGTTGTCCTCG GAAACGTCGCTGGCG CGGAGGGATGGTTCG (SEQ ID NO: 118) |
| C9orf50 | 9 | 129620787 | 129620870 | 84 | AGAGTAGCCAACTTT GGGGGTTGCTGTGAC GTTTAAATGAGCAAG TACATGCCAGTCTTA GAACAGCAAGCTCGG TACAGTGCC (SEQ ID NO: 119) |
| LONRF2 | 2 | 100322387 | 100322463 | 77 | CTCTCAGTCCCGCCG GCTTAGGTAACCCAG GTCGCTGCGGTAACG CAGTGACCGCGCTCC AGGTCCGCGTCTCTTG C (SEQ ID NO: 120) |
| PCDH9 | 13 | 67231171 | 67231265 | 95 | GCGTGCGAAGTCTCC TCTAGCGGAGCGGGA CCGGCCGCGGCGGTG GATCGTGGCGGTCCC TGCACTTCTGCTCCAG CCGCGCCTGGAAACC (SEQ ID NO: 121) |
| GFPT2 | 5 | 180353729 | 180353815 | 87 | CGTAAGGGGCAGAGC GAGGGGTCCGGCATC ACTCGCGCGCTCCGG AAACCC GCGTGAGCCGCTGTT CCTGCCGCGCTCCCAT CTGAG (SEQ ID NO: 122) |

Figure 2A:
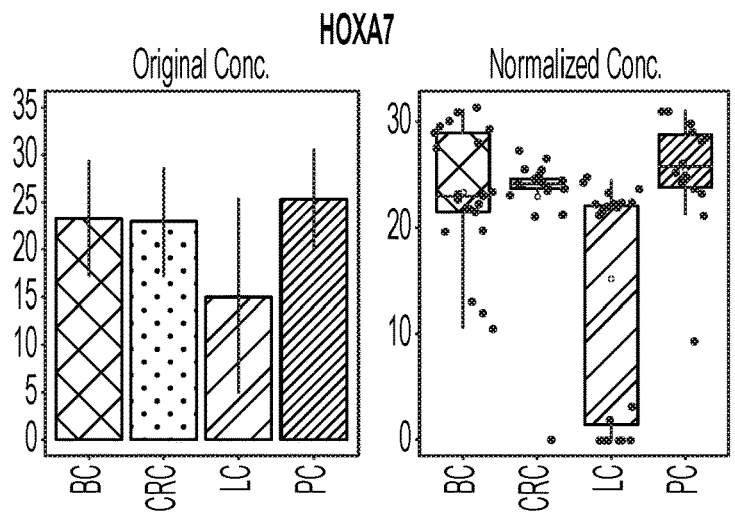
FIGS. 2A-N show detection of methylated markers in plasma. dCt values are plotted for 14 markers that contribute to cancer location identification, i.e., BC—breast cancer, CRC—colorectal cancer, LC—lung cancer, PC—pancreatic cancer.
Figure 2B:
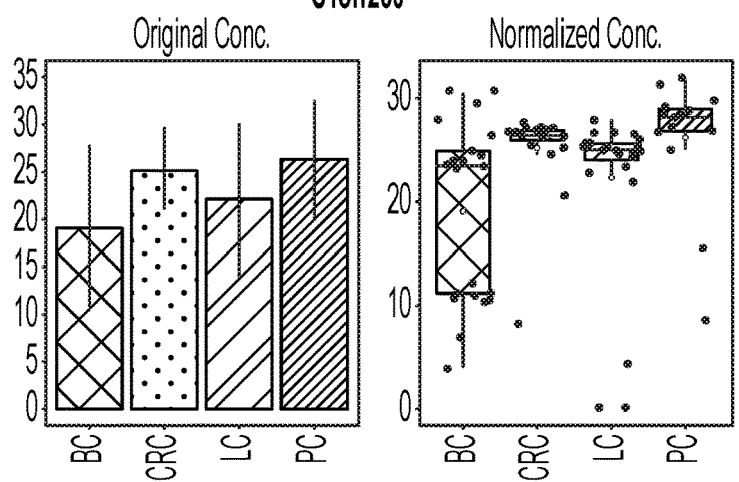
Figure 2C:
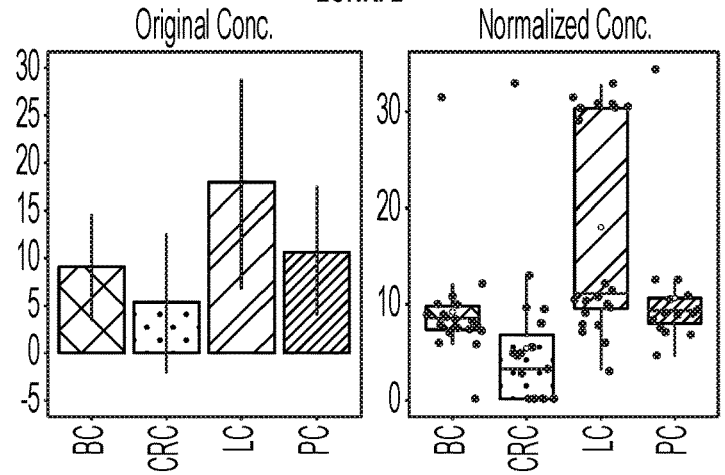
Figure 2D:
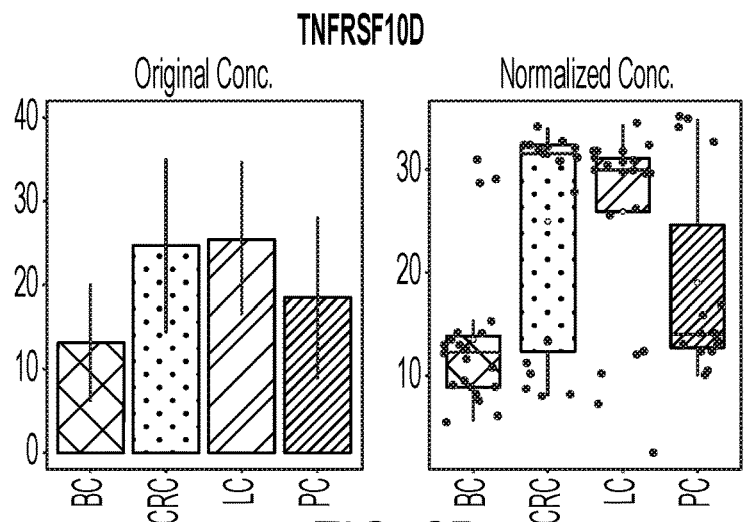
Figure 2E:
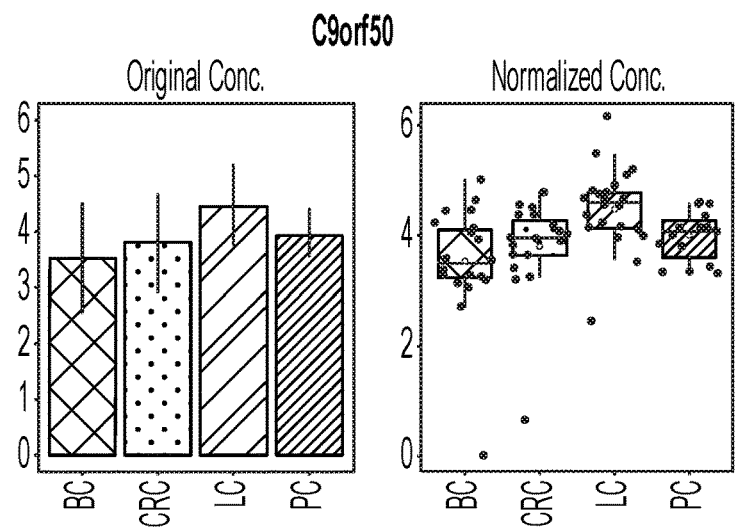
Figure 2F:
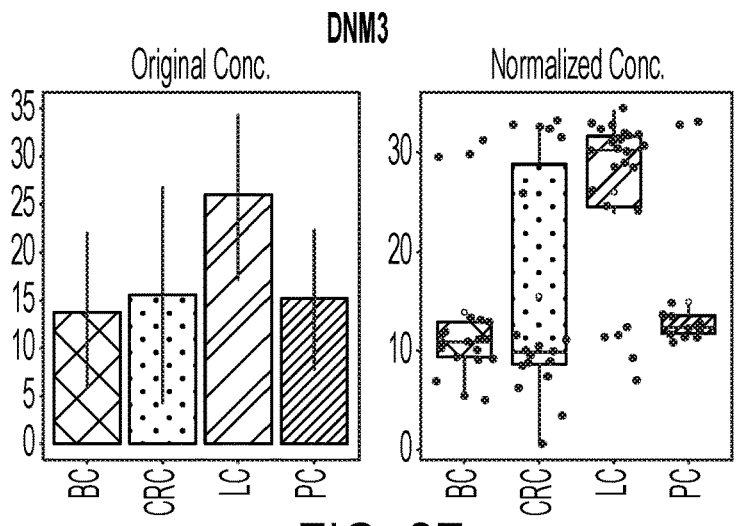
Figure 2G:
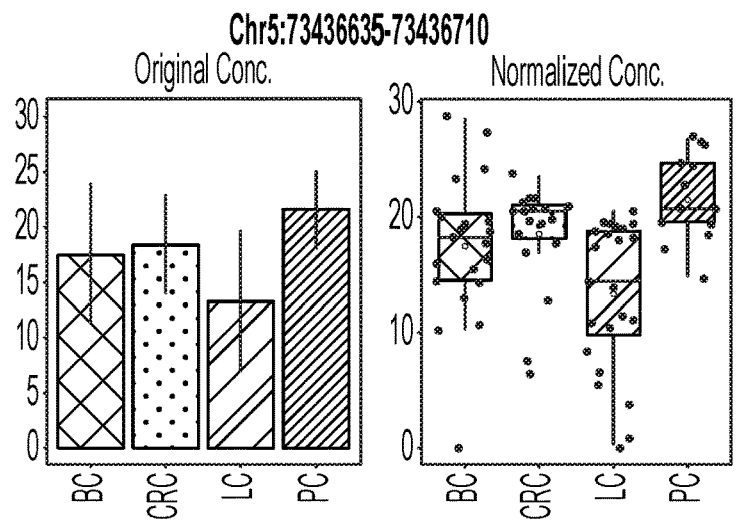
Figure 2H:
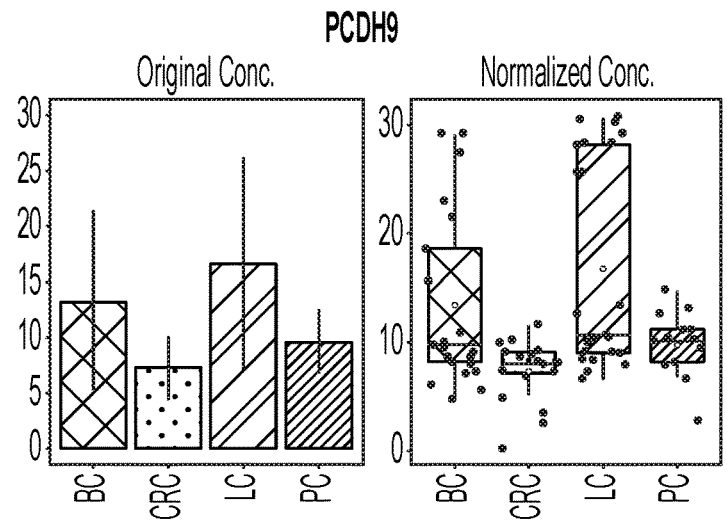
Figure 2I:
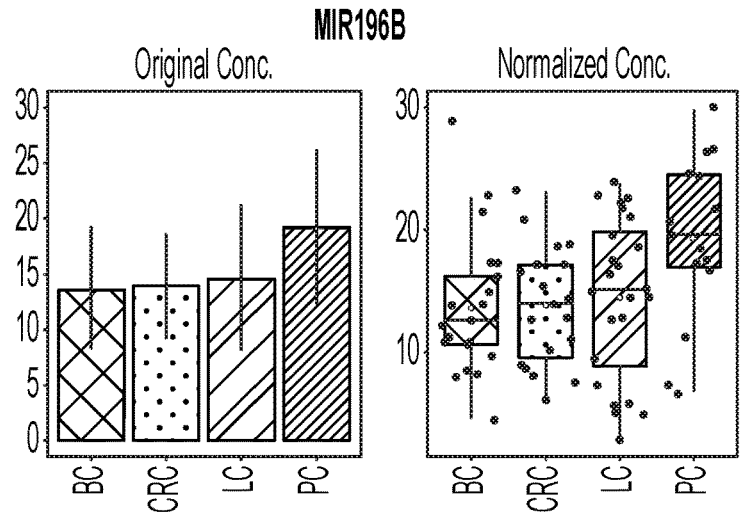
Figure 2J:
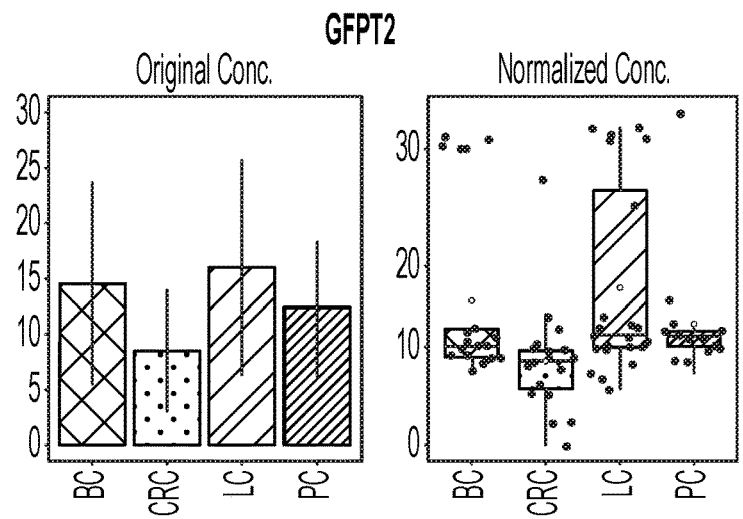
Figure 2K:
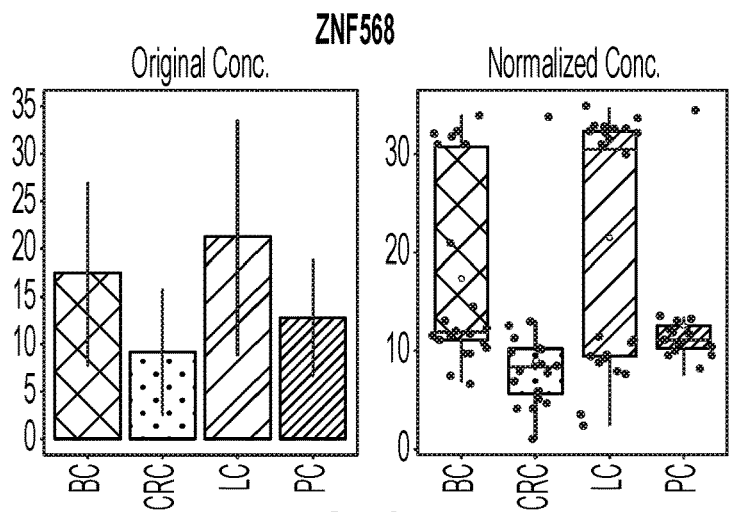
Figure 2L:
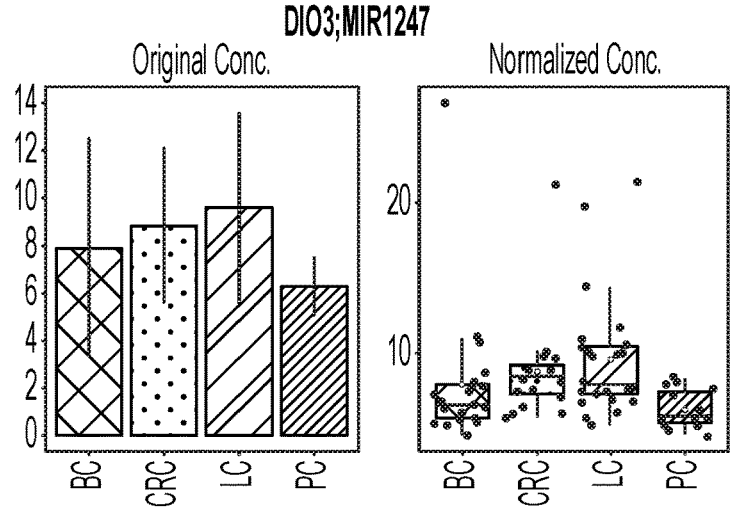
Figure 2M:
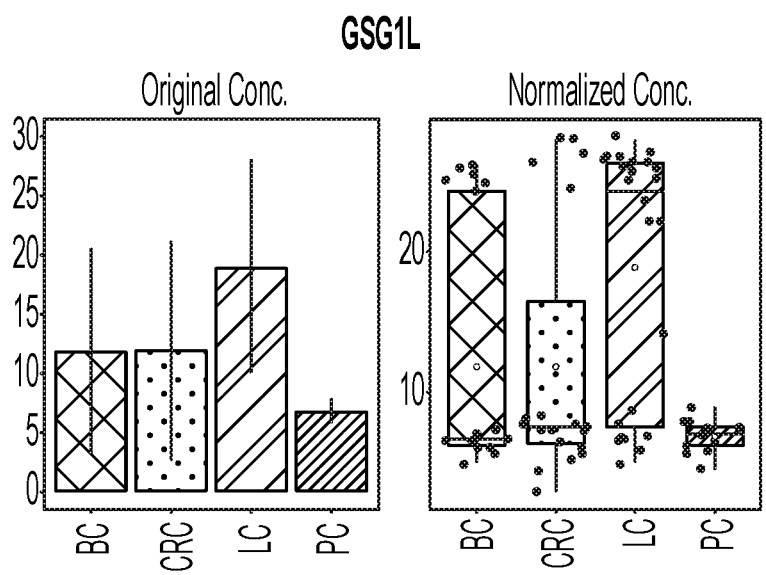
Figure 2N:
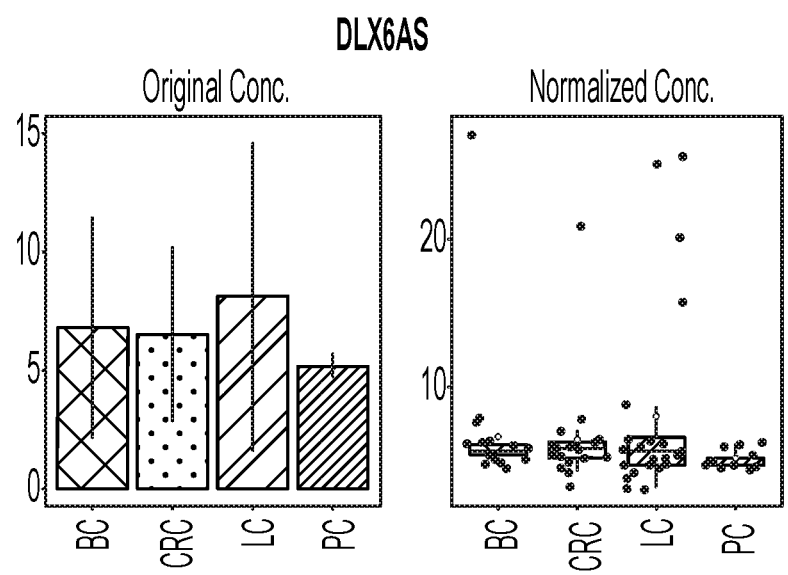

FIGS. 2A-N shows a box-plot representation of each of 14 methylation markers in individual cancer types. dCt values are plotted for 14 markers that contribute to cancer location identification, i.e., BC— breast cancer, CRC-colorectal cancer, LC-lung cancer, PC-pancreatic cancer.

Primer-pairs used for best performing assays are indicated in Tables 3-4. These primer-pairs are designed to amplify DMRs of interest with the condition that at least 1 cut-site for methylation specific restriction enzymes is covered. In most cases 3-15 individual cut-sites are covered.

OTHER EMBODIMENTS

While we have described a number of embodiments, it is apparent that our basic disclosure and examples may provide other embodiments that utilize or are encompassed by the compositions and methods described herein. Therefore, it will be appreciated that the scope of is to be defined by that which may be understood from the disclosure and the appended claims rather than by the specific embodiments that have been represented by way of example.

All references cited herein are hereby incorporated by reference.

SEQUENCE TABLE 1

| uid | Gene | chr | start | end | primer_F | primer_R | width | genome | | Sequence |
| --- | --- | --- | --- | --- | --- | --- | --- | --- | --- | --- |
| 103_1B | MAST1 | 19 | 12867716 | 12867820 | CCCCCT CCATG CAGCA AGC (SEQ ID NO: 29) | CTCCA GCAGC GCCGA GAAAC (SEQ ID NO: 56) | 105 | hg38 | MAST1 | CCCCCTCCATG CAGCAAGCGAT TCTCCGCGTCC GAGGCCAGTTT CCTGGAGGGAG AGGCCAGTCCC CCTTTGGGCGC CCGCCGCCGTT TCTCGGCGCTG CTGGAG (SEQ ID NO: 82) |
| 123_1B | KLK10 | 19 | 51019613 | 51019705 | GCAGG TAGCTT CACCT GGGAG TCG (SEQ ID NO: 30) | AGAGG ATACC AGCGG CAGAC CACA (SEQ ID NO: 57) | 93 | hg38 | KLK10; KLK10; KLK10; KLK10 | GCAGGTAGCTT CACCTGGGAGT CGCCGATAGGA AGGAGGGAGG GGACCCAGACG TGCCTCTGCCC TGCCTGTGGTC TGCCGCTGGTA TCCTCT (SEQ ID NO: 83) |
| 141_1B | HOXD8 | 2 | 176129896 | 176130001 | GGGGT TTGTA AACCG AGGCC AGAG (SEQ ID NO: 31) | CGCTG CCTCC ACTGTT TCCTCT CA (SEQ ID NO: 58) | 106 | hg38 | HOXD8; HOXD8 | GGGGTTTGTAA ACCGAGGCCAG AGTGTCCCCGT GGGCCGAGCGC ACTTTTTTCTTG TCCGGGTGCGC TCAGTCACTGG TGCCTGAGAGG AAACAGTGGA GGCAGCG (SEQ ID NO: 84) |
| 149_1B | C2orf88 | 2 | 190180554 | 190180682 | GCCGG CAGCT GCTTG GTAGT TG (SEQ ID NO: 32) | GAGGG TTGCCT CGATA CTTCCT CA (SEQ ID NO: 59) | 129 | hg38 | C2orf88; C2orf88; C2orf88; C2orf88 | GCCGGCAGCTG CTTGGTAGTTG CGGGGGCGTG AGGGCGGTGGC CCAGACCAACC GGCTGGCAGCC CAGCTCCGCTC CGCCCGCCCCT GCCTCGGACCC TGCGCCTGAGG AAGTATCGAGG CAACCCTC (SEQ ID NO: 85) |
| 175_1B | PREX1 | 20 | 48828337 | 48828448 | TCACC GCGGG CTACG CCACT (SEQ ID NO: 33) | GCTTTC CCAGC CCGGT GTTT (SEQ ID NO: 60) | 112 | hg38 | PREX1 | TCACCGCGGGC TACGCCACTCC CACCCGGCACA CGCGACACCCG CCGCGCGCAGG CTCCTGCTTGC AGGTCCGGCCG |

SEQUENCE TABLE 1-continued

| uid | Gene | chr | start | end | primer_F | primer_R | width | genome | Sequence |
|---|---|---|---|---|---|---|---|---|---|
| | | | | | | | | | CTGCTCGGGCC AAGTAAACACC GGGCTGGGAA AGC (SEQ ID NO: 86) |
| 215_1B | AMOTL2 | 3 | 134364403 | 134364512 | CCATG GCTTCC TTTCTT TGGCA GA (SEQ ID NO: 34) | TTCCCT GAGGA GTCTG GGGAG GAG (SEQ ID NO: 61) | 110 | hg38 | AMOTL2 | CCATGGCTTCC TTTCTTTGGCA GAGTCAGGCTC CAGAAGTCCGC CTTCCTCCACA GGCACCC TAATCTGCCGT GCCCTTGCAGC TTCTCCTCCCC AGACTCCTCAG GGAA (SEQ ID NO: 87) |
| 220_1B | SOX2OT | 3 | 181719490 | 181719596 | GGCAA ATTGA GGCCG AGCTG (SEQ ID NO: 35) | CGAGC CCCAC ACAGC ACCTT (SEQ ID NO: 62) | 107 | hg38 | SOX2OT | GGCAAATTGAG GCCGAGCTGAC GAGCTCCGGCG GGTGGACCTGA CGTCACCGCGG CCCGGGTCACC TCACCCATGGG GCTCCCAAGA AGGTGCTGTGT GGGGCTCG (SEQ ID NO: 88) |
| 236_1B | SCGN | 6 | 25652114 | 25652232 | TCCCC AAAGC GCAGA GACAG A (SEQ ID NO: 36) | CGTCC CTCAG CCCTC AGCAA (SEQ ID NO: 63) | 119 | hg38 | SCGN | CCCCAAAGCGC AGAGACAGAC AGGATCTGCCA GGACAGCGCGC AGGGCGGGGC GGGGACAGGC GCGCCAGGAGC GGGGCGGGCTT CCAGCCGCTGG TTTTGCTGAGG GCTGAGGGACG (SEQ ID NO: 89) |
| 243_1B | HOXA7 | 7 | 27155916 | 27156027 | TCGAA CCCATT AATTG GGCCA TA (SEQ ID NO: 1) | CGGCG CAGCC TTTCTG GTTT (SEQ ID NO: 15) | 112 | hg38 | HOXA7 | TCGAACCCATT AATTGGGCCAT AAAAAGTTTTA TGAGCCTCATT TACATACAATG CTATGGGCTCC ACGCAATGGCG CCTCCGCTCCA ATTAAAACCAG AAAGGCTGCGC CG (SEQ ID NO: 90) |
| 244_1B | HOXA7 | 7 | 27156273 | 27156352 | CCCGG GGATG TTTTGG TCGT (SEQ ID NO: 37) | CCTTTG CGTCC GGCTA CGG (SEQ ID NO: 64) | 80 | hg38 | HOXA7 | CCCGGGGATGT TTTGGTCGTAG GAGGCGCAGG GCAGGTTGCCG TAGGCGTCGGC GCCCAGGCCGT AGCCGGACGCA AAGG (SEQ ID NO: 91) |
| 245_1B | HOXA7 | 7 | 27156291 | 27156403 | GTAGG AGGCG CAGGG CAGGT (SEQ ID NO: 38) | CCTCG ACCGT TCCGG GCTTA (SEQ ID NO: 65) | 113 | hg38 | HOXA7 | GTAGGAGGCGC AGGGCAGGTTG CCGTAGGCGTC GGCGCCCAGGC CGTAGCCGGAC GCAAAGGGGCT CTGATAAAGGG GGCTGTTGACA |

SEQUENCE TABLE 1-continued

| uid | Gene | chr | start | end | primer_F | primer_R | width | genome | Sequence |
|---|---|---|---|---|---|---|---|---|---|
| | | | | | | | | | TTGTATAAGCC CGGAACGGTCG AGG (SEQ ID NO: 92) |
| 253_1B | MIR196B | 7 | 27169630 | 27169719 | CCAAG GAGAG AACCC TGCCA TCG (SEQ ID NO: 2) | GCCTG GGGCA CTCTGT TGCAC T (SEQ ID NO: 16) | 90 | hg38 | MIR196B | CCAAGGAGAG AACCCTGCCAT CGCGCCTGGCC CGGCCCAGCCC AGCCCCTAGGC AACCTGCGCCC GCCAGTGCAAC AGAGTGCCCCA GGC (SEQ ID NO: 93) |
| 279_1B | TNFRSF10D | 8 | 23163949 | 23164031 | GGTGG ATCGA AAGCG CCAAA (SEQ ID NO: 39) | TGGCA GTGTA GCTGC GAGAA CC (SEQ ID NO: 66) | 83 | hg38 | TNFRSF10D; TNFRSF10D | GGTGGATCGAA AGCGCCAAAA ATCAATCAGAA ATCGTCCCCGT AGTTTGTGCGC GTGCAAAGGTT CTCGCAGCTAC ACTGCCA (SEQ ID NO: 94) |
| 281_1B | TNFRSF10D | 8 | 23163995 | 23164099 | TTGTGC GCGTG CAAAG GTTC (SEQ ID NO: 3) | GCGGG AAGGG AGTAC AACTG ACC (SEQ ID NO: 17) | 105 | hg38 | TNFRSF10D | TTGTGCGCGTG CAAAGGTTCTC GCAGCTACACT GCCAGAATAGA ACGTGCTCCTC CGCTTTTATAC CCCGGAAAAA AGGCGTGGTCA GTTGTACTCCC TTCCCGC (SEQ ID NO: 95) |
| 29_1B | NA | 10 | 100830555 | 100830658 | AGCGG CTGAA ATTGG TGCGC C (SEQ ID NO: 40) | CTATG CAGGA ACCCG CCGAC CG (SEQ ID NO: 67) | 104 | hg38 | NA | AGCGGCTGAAA TTGGTGCGCCT TGTGCTGTGGT CTGGGTGTGTC CCGGAGAGGG CGCGCAGGCGC CTATGTCTGTC GCGGGCGGTC GGCGGGTTCCT GCATAG (SEQ ID NO: 96) |
| 44_1B | ME3 | 11 | 86672189 | 86672296 | AGATC CGGTG CGGGT GACAG (SEQ ID NO: 41) | CAAGC CACCA CGCGG GATTA (SEQ ID NO: 68) | 108 | hg38 | ME3; ME3; ME3 | AGATCCGGTGC GGGTGACAGCC GGCGCCACCCC TGCCCCCATCC CTGTGAAAAAG AGGCGACTGCG CGGCGAGGGGT CCCCGTACCCC TAATCCCGCGT GGTGGCTTG (SEQ ID NO: 97) |
| 51_1B | ME3 | 11 | 86672338 | 86672429 | GAGCT GAGGT CTACG CGGTC CC (SEQ ID NO: 42) | CCAGC GCGGT CCACC CATTG (SEQ ID NO: 69) | 92 | hg38 | ME3; ME3; ME3; ME3 | GAGCTGAGGTC TACGCGGTCCC GCTGCGGAGCA GGCGGGGTGA GGAGCTGCGGT CTGTGAGTCCT CTCCCGCCAAT GGGTGGACCGC GCTGG (SEQ ID NO: 98) |

SEQUENCE TABLE 1-continued

| uid | Gene | chr | start | end | primer_F | primer_R | width | genome | Sequence |
|---|---|---|---|---|---|---|---|---|---|
| 69_1B | TXNRD1 | 12 | 104215675 | 104215784 | GGCTATGACTTCGCTGTTGTCACC (SEQ ID NO: 43) | GGAACTGACGGAGCCGAAGGA (SEQ ID NO: 70) | 110 | hg38 | TXNRD1 | GGCTATGACTTCGCTGTTGTCACCCGAGCGCCCCGCCCACCGCGTTCTCCGACCCGCGGCCGGCAGGGGGCTCGCGGCCTCCGCCAGGCGTCCTTCGGCTCCGTCAGTTCC (SEQ ID NO: 99) |
| 87_1B | HAPLN3 | 15 | 88895676 | 8889581 | GTCTCCAGACTCGCTGGGAACCAC (SEQ ID NO: 44) | CCCCTCCCCAAACTCTCCTATTCCA (SEQ ID NO: 71) | 106 | hg38 | HAPLN3 | GTCTCCAGACTCGCTGGGAACCACCGCAAAGAGGGTGTGCAAGAGTTGAGGCCCTCACGTCTTGGGAAAGGAGAGTAGGGGTGGAATAGGAGAGTTTGGGGAGGGG (SEQ ID NO: 100) |
| 93_1B | CYBA | 16 | 88651139 | 88651205 | CATCTGTAGGGTGCAGGGCTGTCC (SEQ ID NO: 45) | TATGCCTCGGCGTGGCTAGAGAGG (SEQ ID NO: 72) | 67 | hg38 | CYBA | CATCTGTAGGGTGCAGGGCTGTCCCGGAGCCTTCTGCCCCGCCCTCTCTAGCCACGCCGAGGCATA (SEQ ID NO: 101) |
| Norm_R1_A133 | ZNF568 | 19 | 36916284 | 36916453 | TGTGTTCTGGCCGGAAGTTGAGTG (SEQ ID NO: 46) | CGAATGTTCATCCCGCGCGCAGTT (SEQ ID NO: 73) | 170 | hg38 | 37407284 | TGTGTTCTGGCCGGAAGTTGAGTGGGGCCGCGGGGCCTGCTGGGAGGTGTTGTCCTCGGAAACGTCGCTGGCGCGGAGGGATGGTTCGGCGCTTAGGCGTCTGTCACAGACCTATCTGCGGGTCGCCTTCACCCAGCATCTCAGAAACTGCGCGCGGGATGAACATTCG (SEQ ID NO: 102) |
| Norm_R1_A151 | ZNF582 | 19 | 56393606 | 56393725 | TCCGGGAAACATAGTCTTTAGGCGT (SEQ ID NO: 47) | GAACAGCACTCCTCCGCGCACTG (SEQ ID NO: 74) | 12 | hg38 | ZNF582 | TCCGGGAAACATAGTCTTTAGGCGTAAAGGCAGCAGCCCGGCCTTGAAGCCGGATCTCGCGATGTTTCAGGGTGAGCCGGACGCAGGCGTGCCTGCGCAGTGCGCGGAGGAGTGCTGTTC (SEQ ID NO: 103) |
| Norm_R1_A156 | ZNF471 | 19 | 56507527 | 56507675 | CCCCACGCGTACTCACACCGAAG (SEQ ID NO: 48) | GCGGGTAAGAGCAGGAGTGTG (SEQ ID NO: 75) | 149 | hg38 | ZNF471 | CCCCACGCGTACTCACACCGAAGGCTCAGCCGTCGCGCGTTTCCCTCCCAGGCCCCAGGAACTAGTAACTAGGGACGCTTCTGGTCTCTAGGCGAGGAGAGGGGGAGAGCGCAATCTTTGCGCCTGCGCA |

SEQUENCE TABLE 1-continued

| uid | Gene | chr | start | end | primer_F | primer_R | width | genome | Sequence |
|---|---|---|---|---|---|---|---|---|---|
| | | | | | | | | | CACTCCTGCTC TTACCCGC (SEQ ID NO: 104) |
| Norm_R1_A157 | ZNF471 | 19 | 56507558 | 56507675 | GTCGC GCGTTT CCCTCC CAG (SEQ ID NO: 49) | GCGGG TAAGA GCAGG AGTGT G (SEQ ID NO: 75) | 118 | hg38 | ZNF471 | GTCGCGCGTTT CCCTCCCAGGC CCCAGGAACTA GTAACTAGGGA CGCTTCTGGTC TCTAGGCGAGG AGAGGGGGAG AGCGCAATCTT TGCGCCTGCGC ACACTCCTGCT CTTACCCGC (SEQ ID NO: 105) |
| Norm_R1_A158 | ZNF471 | 19 | 56507662 | 56507750 | CTGCTC TTACCC GCCGG AACCC TG (SEQ ID NO: 50) | GAGGG ACCTT AGAGC AGAGC GGGC (SEQ ID NO: 76) | 89 | hg38 | ZNF471 | CTGCTCTTACC CGCCGGAACCC TGGGCCACGCC CGGCTCGCGTA ATCACGCACTG CGCAGGCACCG CCCGCTCTGCT CTAAGGTCCCT C (SEQ ID NO: 106) |
| Norm_R1_A171 | THBD | 20 | 23049354 | 23049500 | TCTGA CTGGC ATTGA GGAAG GTCG (SEQ ID NO: 51) | TTGGG GTCCT GGTCC TTGGC GC (SEQ ID NO: 77) | 147 | hg38 | THBD | TCTGACTGGCA TTGAGGAAGGT CGCGGGGCCCG GGTAGAGCGCG AAGCAGTCGTG CTCGACGCACT GGCTGCCACCC GGCTGCGGCTC TGCGGGTGCGG GGAACCCCAGG CCGGCCAGGGC CAGCGCGCCAA GGACCAGGACC CCAA (SEQ ID NO: 107) |
| Norm_R1_A187 | JAM2 | 21 | 25640320 | 25640399 | CCGCG TGGTCT GGGCT CTGTA G (SEQ ID NO: 52) | GAATT CCCTCC ACCTC CGCCC CAC (SEQ ID NO: 78) | 80 | hg38 | JAM2 | CCGCGTGGTCT GGGCTCTGTAG CGTCCCAGCTG AGCCGGCGATA TGCAGCGCAGT TGTGGGCGGA GGTGGAGGGA ATTC (SEQ ID NO: 108) |
| Top50_Assay44 | SDC2 | 8 | 96493985 | 96494062 | CTTCA GAGAG CAGCC TTCCCG G (SEQ ID NO: 53) | GAACG CGGCG CCCTCT CACTT (SEQ ID NO: 79) | 78 | hg38 | SDC2 | CTTCAGAGAGC AGCCTTCCCGG AGCACCAACTC CGTGTCGGAG TGCAGAAACCA ACAAGTGAGA GGGCGCCGCGT TC (SEQ ID NO: 109) |
| Top50_Assay65 | FGF14 | 13 | 102394577 | 102394651 | CAACG GAAAC TTCCCG CGCTA C (SEQ ID NO: 54) | CTCGC CGGGG GCTTC GCTAC (SEQ ID NO: 80) | 75 | hg38 | FGF14 | CAACGGAAACT TCCCGCGCTAC GGCGGCTCCAA CGGGCCGCTTC CGCCGCATTGC GTAGCGAAGCC CCCGCGAG (SEQ ID NO: 110) |
| UDX_230 | CDKN2A | 9 | 21970919 | 21971017 | GCATC TATGC GGGCA TGGTT ACTG | CGTGG ACCTG GCTGA GGAGC TG (SEQ | 99 | hg38 | CDKN2A | GCATCTATGCG GGCATGGTTAC TGCCTCTGGTG CCCCCCGCAGC CGCGCGCAGGT |

SEQUENCE TABLE 1-continued

| uid | Gene | chr | start | end | primer_F | primer_R | width | genome | Sequence |
|-----|------|-----|-------|-----|----------|----------|-------|--------|----------|
| | | | | | (SEQ ID NO: 55) | ID NO: 81) | | | ACCGTGCGACATCGCGATGGCCCAGCTCCTCAGCCAGGTCCACG (SEQ ID NO: 111) |

SEQUENCE TABLE 2

| Gene | chr | start | end | primer_F | primer_R | width | genome | Sequence |
|------|-----|-------|-----|----------|----------|-------|--------|----------|
| HOXA7 | 7 | 27156273 | 27156352 | CCCGGGGATGTTTTGGTCGT (SEQ ID NO: 37) | CCTTTGCGTCCGGCTACGG (SEQ ID NO: 64) | 80 | hg38 | HOXA7 CCCGGGGATGTTTTGGTCGTAGGAGGCGCAGGGCAGGTTGCCGTAGGCGTCGGCGCCCAGGCCGTAGCCGGACGCAAAGG (SEQ ID NO: 91) |
| NA | 10 | 100830555 | 100830658 | AGCGGCTGAAATTGGTGCGCC (SEQ ID NO: 40) | CTATGCAGGAACCCGCCGACCG (SEQ ID NO: 67) | 104 | hg38 | NA AGCGGCTGAAATTGGTGCGCCTTGTGCTGTGGTCTGGGTGTGTCCCGGAGAGGCGCGCAGGCGCCTATGTCTGTCGCGGGGCGGTCGGCGGGTTCCTGCATAG (SEQ ID NO: 96) |
| JAM2 | 21 | 25640320 | 25640399 | CCGCGTGGTCTGGGCTCTGTAG (SEQ ID NO: 52) | GAATTCCCTCCACCTCCGCCCAC (SEQ ID NO: 78) | 80 | hg38 | JAM2 CCGCGTGGTCTGGGCTCTGTAGCGTCCCAGCTGAGCCGGCGATATGCAGCGCACTTGTGGGGCGGAGGTGGAGGGAATTC (SEQ ID NO: 108) |

SEQUENCE TABLE 3

| Gene | chr | start | end | primer_F | primer_R | width | genome | Sequence |
|------|-----|-------|-----|----------|----------|-------|--------|----------|
| KLK10 | 19 | 51019613 | 5109705 | GCAGGTAGCTTCACCTGGGAGTCG (SEQ ID NO: 30) | AGAGGATACCAGCGGCAGACCACA (SEQ ID NO: 57) | 93 | hg38 | KLK10; KLK10; KLK10; KLK10 GCAGGTAGCTTCACCTGGGAGTCGCCGATAGGAAGGAGGGAGGGGACCCAGACGTGCCTCTGCCCTGCCTGTGGTCTGCCGCTGGTATCCTCT (SEQ ID NO: 83) |
| HOXA7 | 7 | 27156291 | 27156403 | GTAGGAGGCGCAGGGCAGGT (SEQ ID NO: 38) | CCTCGACCGTTCCGGGCTTA (SEQ ID NO: 65) | 113 | hg38 | HOXA7 GTAGGAGGCGCAGGGCAGGTTGCCGTAGGCGTCGGCGCCCAGGCCGTAGCCGGACGCAAAGGGGCTCTGATAAAGGGGGCTGTTGACATTGTATAAGCCCGGAACGGTCGAGG (SEQ ID NO: 92) |
| NA | 10 | 100830555 | 100830658 | AGCGGCTGAAATTGGTGCGCC (SEQ ID NO: 40) | CTATGCAGGAACCCGCCGACCG (SEQ ID NO: 67) | 104 | hg38 | NA AGCGGCTGAAATTGGTGCGCCTTGTGCTGTGGTCTGGGTGTGTCCCGGAGAGGGCGCGCAGGCGCCTATGTCTGTCGCGGGGCGGTCGGCGGGTTCCTGCATAG (SEQ ID NO: 96) |
| TXNRD1 | 12 | 104215675 | 104215784 | GGCTATGACTTCGCTGTTGTCACC (SEQ ID NO: 43) | GGAACTGACGGAGCCGAAGGA (SEQ ID NO: 70) | 110 | hg38 | TXNRD1 GGCTATGACTTCGCTGTTGTCACCGAGCGCCCCGACCCACCGCGTTCTCCGACCCGCGGCCGGCAGGGGGCTCGCGGCCTCCGCCAGGCGTCCTTCGGCTCCGTCAGTTCC (SEQ ID NO: 99) |

SEQUENCE TABLE 3-continued

| Gene | chr | start | end | primer_F | primer_R | width | genome | Sequence |
|---|---|---|---|---|---|---|---|---|
| THBD | 20 | 23049354 | 23049500 | TCTGACTGGCATTGAGGAAGGTCG (SEQ ID NO: 51) | TTGGGGTCCTGGTCCTTGGCGC (SEQ ID NO: 77) | 147 | hg38 | THBD | TCTGACTGGCATTGAGGAAGGTCGCGGGGCCCGGGTAGAGCGCGAAGCAGTCGTGCTCGACGCACTGGCTGCCACCCGGCTGCGGCTCTGCGGGTGCGGGAACCCCAGGCCGGCCAGGGCCAGCGCGCCAAGGACCAGGACCCCAA (SEQ ID NO: 107) |

SEQUENCE TABLE 4

| Gene | chr | start | end | primer_F | primer_R | width | genome | Sequence |
|---|---|---|---|---|---|---|---|---|
| HOXD8 | 2 | 176129896 | 176130001 | GGGGTTTGTAAACCGAGGCCAGAG (SEQ ID NO: 31) | CGCTGCCTCCACTGTTTCCTCTCA (SEQ ID NO: 58) | 106 | hg38 | HOXD8; HOXD8 | GGGGTTTGTAAACCGAGGCCAGAGTGTCCCCGTGGGCCGAGCGCACTTTTTTCTTGTCCGGGTGCGCTCAGTCACTGGTGCCTGAGAGGAAACAGTGGAGGCAGCG (SEQ ID NO: 84) |
| SCGN | 6 | 25652114 | 25652232 | TCCCCAAAGCGCAGAGACAGA (SEQ ID NO: 36) | CGTCCCTCAGCCCTCAGCAA (SEQ ID NO: 63) | 119 | hg38 | SCGN | CCCCAAAGCGCAGAGACAGACAGGATCTGCCAGGACAGCGCGCAGGGCGGGGCGGGGACAGGCGCGCCAGGAGCGGGGCGGGCTTCCAGCCGCTGGTTTTGCTGAGGGCTGAGGGACG (SEQ ID NO: 89) |
| HOXA7 | 7 | 27156291 | 27156403 | GTAGGAGGCGCAGGGCAGGT (SEQ ID NO: 38) | CCTCGACCGTTCCGGGCTTA (SEQ ID NO: 65) | 113 | hg38 | HOXA7 | GTAGGAGGCGCAGGGCAGGTTGCCGTAGGCGTCGGCGCCCAGGCCGTAGCCGGACGCAAAGGGGCTCTGATAAAGGGGGCTGTTGACATTGTATAAGCCCGGAACGGTCGAGG (SEQ ID NO: 92) |
| MIR196 | 7 | 27169630 | 27169719 | CCAAGGAGAGAACCCTGCCATCG (SEQ ID NO: 2) | GCCTGGGGCACTCTGTTGCACT (SEQ ID NO: 16) | 90 | hg38 | MIR196B | CCAAGGAGAGAACCCTGCCATCGCGCCTGGCCCGGCCCAGCCCAGCCCTAGGCAACCTGCGCCCGCCAGTGCAACAGAGTGCCCAGGC (SEQ ID NO: 93) |
| NA | 10 | 100830555 | 100830658 | AGCGGCTGAAATTGGTGCGCC (SEQ ID NO: 40) | CTATGCAGGAACCCGCCGACCG (SEQ ID NO: 67) | 104 | 1108 | NA | AGCGGCTGAAATTGGTGCGCCTTGTGCTGTGGTCTGGGTGTGTCCCGGAGAGGGCGCGCAGGCGCCTATGTCTGTCGCGGGGCGGTCGGCGGGTTCCTGCATAG (SEQ ID NO: 96) |
| TXNRD1 | 12 | 104215675 | 104215784 | GGCTATGACTTCGCTGTTGTCACC (SEQ ID NO: 43) | GGAACTGACGGAGCCGAAGGA (SEQ ID NO: 70) | 110 | hg38 | TXNRD1 | GGCTATGACTTCGCTGTTGTCACCGAGCGCCCCGCCCACCGCGTTCTCCGACCCGCGGCCGGCAGGGGCTCGCGGCCTCCGCCAGGCGTCCTTCGGCTCCGTCAGTTCC (SEQ ID NO: 99) |
| HAPLN3 | 15 | 88895676 | 88895781 | GTCTCCAGACTCGCTGGGAACCAC (SEQ ID NO: 44) | CCCCTCCCCAAACTCTCCTATTCCA (SEQ ID NO: 71) | 106 | hg38 | HAPLN3 | GTCTCCAGACTCGCTGGGAACCACCGCAAAGAGGGTGTGCAAGAGTTGAGGCCCTCACGTCTTGGGAAAGGAGAGTAGGGGTGAATAGGAGAGTTTGGGGAGGGG (SEQ ID NO: 100) |
| THBD | 20 | 23049354 | 23049500 | TCTGACTGGCATT | TTGGGGTCCTGG | 147 | hg38 | THBD | TCTGACTGGCATTGAGGAAGGTCGCGGGGCCCGG |

SEQUENCE TABLE 4-continued

| Gene | chr | start | end | primer_F | primer_R | width | genome | Sequence |
|---|---|---|---|---|---|---|---|---|
| | | | | GAGGAA GGTCG (SEQ ID NO: 51) | TCCTTG GCGC (SEQ ID NO: 77) | | | GTAGAGCGCGAAGCAGT CGTGCTCGACGCACTGG CTGCCACCCGGCTGCGG CTCTGCGGGTGCGGGGA ACCCCAGGCCGGCCAGG GCCAGCGCGCCAAGGAC CAGGACCCCAA (SEQ ID NO: 107) |
| SDC2 | 8 | 96493985 | 96494062 | CTTCAGA GAGCAG CCTTCCC GG (SEQ ID NO: 53) | GAACGC GGCGCC CTCTCA CTT (SEQ ID NO: 79) | 78 | hg38 | SDC2 CTTCAGAGAGCAGCCTTC CCGGAGCACCAACTCCG TGTCGGGAGTGCAGAAA CCAACAAGTGAGAGGGC GCCGCGTTC (SEQ ID NO: 109) |

SEQUENCE TABLE 5

| Gene | chr | start | end | primer_F | primer_R | width | genome | Sequence |
|---|---|---|---|---|---|---|---|---|
| MAST1 | 19 | 12867716 | 12867820 | CCCCCTC CATGCA GCAAGC (SEQ ID NO: 29) | CTCCAG CAGCGC CGAGAA AC (SEQ ID NO: 56) | 105 | hg38 | MAST1 CCCCCTCCATGCAGCAA GCGATTCTCCGCGTCCGA GGCCAGTTTCCTGGAGG GAGAGGCCAGTCCCCCT TTGGGCGCCCGCCGCCGT TTCTCGGCGCTGCTGGAG (SEQ ID NO: 82) |
| HOXD8 | 2 | 176129896 | 176130001 | GGGGTTT GTAAAC CGAGGC CAGAG (SEQ ID NO: 31) | CGCTGC CTCCAC TGTTTC CTCTCA (SEQ ID NO: 58) | 106 | hg38 | HOXD8; HOXD8 GGGGTTTGTAAACCGAG GCCAGAGTGTCCCCGTG GGCCGAGCGCACTTTTTT CTTGTCCGGGTGCGCTCA GTCACTGGTGCCTGAGA GGAAACAGTGGAGGCAG CG (SEQ ID NO: 84) |
| PREX1 | 20 | 48828337 | 44828448 | TCACCGC GGGCTA CGCCACT (SEQ ID NO: 33) | GCTTTC CCAGCC CGGTGT TT (SEQ ID NO: 60) | 112 | hg38 | PREX1 TCACCGCGGGCTACGCC ACTCCCACCCGGCACAC GCGACACCCGCCGCGCG CAGGCTCCTGCTTGCAGG TCCGGCCGCTGCTCGGGC CAAGTAAACACCGGGCT GGGAAAGC (SEQ ID NO: 86) |
| AMOTL2 | 3 | 134364403 | 134364512 | CCATGG CTTCCTT TCTTTGG CAGA (SEQ ID NO: 34) | TTCCCT GAGGAG TCTGGG GAGGAG (SEQ ID NO: 61) | 110 | hg38 | AMOTL2 CCATGGCTTCCTTTCTTT GGCAGAGTCAGGCTCCA GAAGTCCGCCTTCCTCCA CAGGCACCC TAATCTGCCGTGCCCTTG CAGCTTCTCCTCCCAGA CTCCTCAGGGAA (SEQ ID NO: 87) |
| SCGN | 6 | 25652114 | 25652232 | TCCCCAA AGCGCA GAGACA GA (SEQ ID NO: 36) | CGTCCC TCAGCC CTCAGC AA (SEQ ID NO: 63) | 119 | hg38 | SCGN CCCCAAAGCGCAGAGAC AGACAGGATCTGCCAGG ACAGCGCGCAGGGCGGG GCGGGGACAGGCGCGCC AGGAGCGGGGCGGGCTT CCAGCCGCTGGTTTTGCT GAGGGCTGAGGGACG (SEQ ID NO: 89) |
| HOXA7 | 7 | 27155916 | 27156027 | TCGAAC CCATTAA TTGGGCC ATA (SEQ ID NO: 1) | CGGCGC AGCCTT TCTGGT TT (SEQ ID NO: 15) | 112 | hg38 | HOXA7 TCGAACCCATTAATTGGG CCATAAAAAGTTTTATGA GCCTCATTTACATACAAT GCTATGGGCTCCACGCA ATGGCGCCTCCGCTCCAA TTAAACCAGAAAGGCT GCGCCG (SEQ ID NO: 90) |
| MIR96B | 7 | 27169630 | 27169719 | CCAAGG AGAGAA CCCTGCC ATCG | GCCTGG GGCACT CTGTTC CACT | 90 | hg38 | MIR196B CCAAGGAGAGAACCCTG CCATCGCGCCTGGCCCG GCCCAGCCCAGCCCCTA GGCAACCTGCGCCCGCC |

SEQUENCE TABLE 5-continued

| Gene | chr | start | end | primer_F | primer_R | width | genome | Sequence |
|---|---|---|---|---|---|---|---|---|
| | | | | (SEQ ID NO: 2) | (SEQ ID NO: 16) | | | AGTGCAACAGAGTGCCC CAGGC (SEQ ID NO: 93) |
| TNFRSF10D | 8 | 23163949 | 23164031 | GGTGGA TCGAAA GCGCCA AA (SEQ ID NO: 39) | TGGCAG TGTAGC TGCGAG AACC (SEQ ID NO: 66) | 83 | hg38 | TNFRSF10D;TNFRSF10D GGTGGATCGAAAGCGCC AAAAATCAATCAGAAAT CGTCCCCGTAGTTTGTGC GCGTGCAAAGGTTCTCG CAGCTACACTGCCA (SEQ ID NO: 94) |
| NA | 10 | 100830555 | 100830658 | AGCGGC TGAAATT GGTGCG CC (SEQ ID NO: 40) | CTATGC AGGAAC CCGCCG ACCG (SEQ ID NO: 67) | 104 | hg38 | NA | AGCGGCTGAAATTGGTG CGCCTTGTGCTGTGGTCT GGGTGTGTCCCGAGAG GGCGCGCAGGCGCCTAT GTCTGTCGCGGGCGGT CGGCGGGTTCCTGCATA G (SEQ ID NO: 96) |
| TXNRD1 | 12 | 104215675 | 104215784 | GGCTAT GACTTCG CTGTTGT CACC (SEQ ID NO: 43) | GGAACT GACGGA GCCGAA GGA (SEQ ID NO: 70) | 110 | hg38 | TXNRD1 | GGCTATGACTTCGCTGTT GTCACCGAGCGCCCGC CCACCGCGTTCTCCGACC CGCGGCCGGCAGGGGC TCGCGGCCTCCGCCAGG CGTCCTTCGGCTCCGTCA GTTCC (SEQ ID NO: 99) |
| HAPLN3 | 15 | 88895676 | 88895781 | GTCTCCA GACTCG CTGGGA ACCAC (SEQ ID NO: 44) | CCCCTC CCCAAA CTCTCC TATTCC A (SEQ ID NO: 71) | 106 | hg38 | HAPLN3 | GTCTCCAGACTCGCTGGG AACCACCGCAAAGAGGG TGTGCAAGAGTTGAGGC CCTCACGTCTTGGGAAA GGAGAGTAGGGGTGAA TAGGAGAGTTTGGGGAG GGG (SEQ ID NO: 100) |
| CYBA | 16 | 88651139 | 88651205 | CATCTGT AGGGTG CAGGGC TGTCC (SEQ ID NO: 45) | TATGCC TCGGCG TGGCTA GAGAGG (SEQ ID NO: 72) | 67 | hg38 | CYBA | CATCTGTAGGGTGCAGG GCTGTCCCGGAGCCTTCT GCCCCGCCCTCTCTAGC CACGCCGAGGCATA (SEQ. NO: 101) |
| ZNF582 | 19 | 56393606 | 56393725 | TCCGGG AAACAT AGTCTTT AGGCGT (SEQ ID NO: 47) | GAACAG CACTCC TCCGCG CACTG (SEQ ID NO: 74) | 120 | hg38 | ZINF582 | TCCGGGAAACATAGTCTT TAGGCGTAAAGGCAGCA GCCCGGCCTTGAAGCCG GATCTCGCGATGTTTCAG GGTGAGCCGGACGCAGG CGTGCCTGCGCAGTGCG CGGAGGAGTGCTGTTC (SEQ ID NO: 103) |
| THBD | 20 | 23049354 | 23049500 | TCTGACT GGCATT GAGGAA GGTCG (SEQ ID NO: 51) | TTGGGG TCCTGG TCCTTG GCGC (SEQ ID NO: 77) | 147 | hg38 | THBD | TCTGACTGGCATTGAGG AAGGTCGCGGGGCCCGG GTAGAGCGCGAAGCAGT CGTGCTCGACGCACTGG CTGCCACCCGGCTGCGG CTCTGCGGGTGCGGGGA ACCCCAGGCCGGCCAGG GCCAGCGCGCCAAGGAC CAGGACCCCAA (SEQ ID NO: 107) |
| SDC2 | 8 | 96493985 | 96494062 | CTTCAGA GAGCAG CCTTCCC GG (SEQ ID NO: 53) | GAACGC GGCGCC CTCTCA CTT (SEQ ID NO: 79) | 78 | hg38 | SDC2 | CTTCAGAGAGCAGCCTTC CCGGAGCACCAACTCCG TGTCGGGAGTGCAGAAA CCAACAAGTGAGAGGGC GCCGCGTTC (SEQ ID NO: 109) |
| FGF14 | 13 | 102394577 | 102394651 | CAACGG AAACTTC CCGCGCT AC (SEQ ID NO: 54) | CTCGCC GGGGGC TTCGCT AC (SEQ ID NO: 80) | 75 | hg38 | FGF14 | CAACGGAAACTTCCCGC GCTACGGCGGCTCCAAC GGGCCGCTTCCGCCGCAT TGCGTAGCGAAGCCCCC GGCGAG (SEQ ID NO: 110) |
| CDKN2A | 9 | 21970919 | 21971017 | GCATCTA TGCGGG CATGGTT | CGTGGA CCTGGC TGAGGA | 99 | hg38 | CDKN2A | GCATCTATGCGGGCATG GTTACTGCCTCTGGTGCC CCCCGCAGCCGCGCA |

SEQUENCE TABLE 5-continued

| Gene | chr | start | end | primer_F | primer_R | width | genome | Sequence |
|---|---|---|---|---|---|---|---|---|
| | | | | ACTG (SEQ ID NO: 55) | GCTG (SEQ ID NO: 81) | | | GGTACCGTGCGACATCG CGATGGCCCAGCTCCICA GCCAGGTCCACG (SEQ ID NO: 111) |

SEQUENCE TABLE 6

| annotations | chr | start | end | Width | genome | primer_F | primer_R | annotations | sequence |
|---|---|---|---|---|---|---|---|---|---|
| DNM3 | 1 | 171841774 | 171841857 | 84 | hg39 | CAGAGCGCC GGCAAGAGC (SEQ ID NO: 4) | CCCCACTGC CGCATCCTT AC (SEQ ID NO: 18) | DNM3 | CAGAGCGCCGGC AAGAGCTCGGTG CTCGAGAACTTCG TGGGCAGGTAAG CGCGCAGGGCGC GGAGTAAGGATG CGGCAGTGGGG (SEQ ID NO: 112) |
| NA | 5 | 73436635 | 73436710 | 76 | hg47 | CAGGCTGGG CGGTCTTTG AC (SEQ ID NO: 8) | GGGGTAGCG GGTGCTTCC AG (SEQ ID NO: 22) | NA | CAGGCTGGGCGG TCTTTGACCCCCC GCGCCTCCCGCCC ACAGCCGGAGCC CGGCAGCTGGAA GCACCCGCTACCC C (SEQ ID NO: 113) |
| HOXA7 | 7 | 27155916 | 27156027 | 112 | hg50 | TCGAACCCA TTAATTGGG CCATA (SEQ ID NO: 1) | CGGCGCAGC CITICTGGT TT (SEQ ID NO: 15) | HOXA7 | TCGAACCCATTAA TTGGGCCATAAA AAGTTTTATGAGC CTCATTTACATAC AATGCTATGGGCT CCACGCAATGGC GCCTCCGCTCCAA TTAAAACCAGAA AGGCTGCGCCG (SEQ ID NO: 90) |
| MIR196B | 7 | 27169630 | 27169719 | 90 | hg53 | CCAAGGAGA GAACCCTGC CATCG (SEQ ID NO: 2) | GCCTGGGGC ACTCTGTTG CACT (SEQ ID NO: 16) | MIR196B | CCAAGGAGAGAA CCCTGCCATCGCG CCTGGCCCGGCCC AGCCCAGCCCCT AGGCAACCTGCG CCGCCAGTGCA ACAGAGTGCCCC AGGC (SEQ ID NO: 93) |
| DLX6-AS1 | 7 | 97014186 | 97014266 | 81 | hg49 | CAAGACCTG GCGCATCTT TGC (SEQ ID NO: 9) | TTGCAGGCT GGATTAGGA TGC (SEQ ID NO: 23) | DLX6-AS1 | CAAGACCTGGCG CATCTTTGCAAAT TACAGATAATTGT AAACGTCCAGAT TATGATAATAGC ATCCTAATCCAGC CTGCAA (SEQ ID NO: 114) |
| TNFRSF10D | 8 | 23163995 | 23164099 | 105 | hg55 | TTGTGCGCG TGCAAAGGT TC (SEQ ID NO: 3) | GCGGGAAG GGAGTACAA CTGACC (SEQ. ID NO: 17) | TNFRSF10D | TTGTGCGCGTGCA AAGGTTCTCGCA GCTACACTGCCA GAATAGAACGTG CTCCTCCGCTTTT ATACCCCGGAAA AAAGGCGTGGTC AGTTGTACTCCCT TCCCGC (SEQ ID NO: 95) |
| C1orf230 | 1 | 151721583 | 151721679 | 97 | hg38 | TTAGCGCAG CGCAGCTGG AG (SEQ ID NO: 5) | CCCAGTCCT GGGGCAGCT ACA (SEQ ID NO: 19) | RIIAD1, CELF3 | TTAGCGCAGCGC AGCTGGAGCAGC TGCGAAAATTCA AGGTGGGTGCGC CCGCGCCCCCATC |

SEQUENCE TABLE 6-continued

| annotations | chr | start | end | Width | genome | primer_F | primer_R | annotations | sequence |
|---|---|---|---|---|---|---|---|---|---|
| | | | | | | | | | CAGCGTCCACCA AAGTGTAGCTGC CCCAGGACTGGG (SEQ ID NO: 115) |
| DIO3OS, MIR1247 | 14 | 101561395 | 101515056 | 111 | hg66 | TCCGGGCTC AAGTTGCAA GG (SEQ ID NO: 10) | GCGAGGCAT CTGGGCTTC AG (SEQ ID NO: 24) | DIO3OS, MIR1247 | TCCGGGCTCAAGT TGCAAGGGGGCG GGCCGGGCCGGA GGTGGAGTCTCCC GCCAATTGAAGC CTCCGCTATAAAT TGAACTCCCTGCA CTGCTGAAGCCC AGATGCCTCGC (SEQ ID NO: 116) |
| GSG1L | 16 | 28063861 | 28063964 | 104 | hg69 | CCGAAAGAA ATCCGAGCC AGGGTGA (SEQ ID NO: 11) | GGTTTTGTT GCCCCACGT CC (SEQ ID NO: 25) | GSG1L | CCGAAAGAAATC CGAGCCAGGGTG AGGGTCTGAGAC GCAAGGAGAATC CCAG GCAAGGCGCTCC TGAGAAAAGATC CCCACGGCGGAC GTGGGGCAACAA AACC (SEQ ID NO: 117) |
| ZNF568 | 19 | 36916252 | 36916371 | 120 | hg77 | GCCCAAGCC TCACCCTCA CACAG (SEQ ID NO: 6) | CGAACCATC CCTCCGCGC CA (SEQ ID NO: 20) | ZNF568 | GCCCAAGCCTCA CCCTCACACAGG AAAGCAGATGTG TTCTGGCCGGAA GTTGAGTGGGGC CGCGGGGCCTGC TGGGAGGTGTTGT CCTCGGAAACGT CGCTGGCGCGGA GGGATGGTTCG (SEQ ID NO: 118) |
| C9orf50 | 9 | 129620787 | 129620870 | 84 | hg57 | AGAGTAGCC AACTTTGGG GGTTGGT (SEQ ID NO: 7) | GGCACTGTA CCGAGCTTG CTGTTCT (SEQ ID NO: 21) | C9orf50 | AGAGTAGCCAAC TTTGGGGGTTGCT GTGACGTTTAAAT GAGCAAGTACAT GCCAGTCTTAGA ACAGCAAGCTCG GTACAGTGCC (SEQ ID NO: 119) |
| LONRF2 | 2 | 100322387 | 100322463 | 77 | hg43 | CTCTCAGTC CCGCCGGCT TAGGTA (SEQ ID NO: 12) | GCAAGAGAC GCGGACCTG GAGC (SEQ ID NO: 26) | LONRF2 | CTCTCAGTCCCGC CGGCTTAGGTAA CCCAGGTCGCTGC GGTAACGCAGTG ACCGCGCTCCAG GTCCGCGTCTCTT GC (SEQ ID No: 120) |
| PCDH9 | 13 | 67231171 | 67231265 | 95 | hg65 | GCGTGCGAA GTCTCCTCT AGCGGA (SEQ ID NO: 13) | CTCAGGTTT CCAGGCGCG GCT (SEQ ID NO: 27) | PCDH9 | GCGTGCGAAGTC TCCTCTAGCGGAG CGGGACCGGCCG CGGCGGTGGATC GTGGCGGTCCCTG CACTTCTGCTCCA GCCGCGCCTGGA AACCTGAG (SEQ ID NO: 121) |
| GFPT2 | 5 | 180353729 | 180353815 | 87 | hg46 | CGTAAGGGG CAGAGCGAG GGGT (SEQ ID NO: 14) | CTCAGATGG GAGCGCGGC AGGAA (SEQ ID NO: 28) | GFPT2 | CGTAAGGGGCAG AGCGAGGGGICC GGCATCACTCGC GCGCTCCGGAAA CCC GCGTGAGCCGCT GTTCCTGCCGCGC TCCCATCTGAG (SEQ ID NO: 122) |

SEQUENCE TABLE 7

| annotations | chr | start | end | Width | genome | primer_F | primer_R | annotations | sequence |
|---|---|---|---|---|---|---|---|---|---|
| HOXA7 | 7 | 27155916 | 27156027 | 112 | hg50 | TCGAACCCA TTAATTGGG CCATA (SEQ ID NO: 1) | CGGCGCAGC CTTTCTGGT TT (SEQ ID NO: 15) | HOXA7 | TCGAACCCATTAATTG GGCCATAAAAAGTTTT ATGAGCCTCATTTACA TACAATGCTATGGGCT CCACGCAATGGCGCCT CCGCTCCAATTAAAAC CAGAAAGGCTGCGCC G (SEQ ID NO: 90) |
| MIR196B | 7 | 27169630 | 27169719 | 90 | hg53 | CCAAGGAGA GAACCCTGC CATCG (SEQ ID NO: 2) | GCCTGGGGC ACTCTGTIG CACT (SEQ ID NO: 16) | MIR196B | CCAAGGAGAGAACCC TGCCATCGCGCCTGGC CCGGCCCAGCCCAGCC CCTAGGCAACCTGCGC CCGCCAGTGCAACAG AGTGCCCCAGGC (SEQ. ID NO: 93) |
| TNFRSF10D | 8 | 23163995 | 23164099 | 105 | hg55 | TTGTGCGCG TGCAAAGGT TC (SEQ ID NO: 3) | GCGGGAAG GGAGTACAA CTGACC (SEQ ID NO: 17) | TNFRSF10D | TTGTGCGCGTGCAAAG GTTCTCGCAGCTACAC TGCCAGAATAGAACGT GCTCCTCCGCTTTTAT ACCCCGGAAAAAAGG CGTGGTCAGTTGTACT CCCTTCCCGC (SEQ ID NO: 95) |
| DNM3 | 1 | 171841774 | 171841857 | 84 | hg39 | CAGAGCGCC GGCAAGAGC (SEQ ID NO: 4) | CCCCACTGC CGCATCCTT AC (SEQ ID NO: 18) | DNM3 | CAGAGCGCCGGCAAG AGCTCGGTGCTCGAGA ACTTCGTGGGCAGGTA AGCGCGCAGGGCGCG GAGTAAGGATGCGGC AGTGGGG (SEQ ID NO: 112) |
| C1orf230 | 1 | 151721583 | 151721679 | 97 | hg38 | TTAGCGCAG CGCAGCTGG AG (SEQ ID NO: 5) | CCCAGTCCT GGGGCAGCT ACA (SEQ ID NO: 19) | RIIAD1, CELF3 | TTAGCGCAGCGCAGCT GGAGCAGCTGCGAAA ATTCAAGGTGGGTGCG CCCGCGCCCCCATCCA GCGTCCACCAAAGTGT AGCTGCCCCAGGACTG GG (SEQ ID NO: 115) |
| ZNF568 | 19 | 36916252 | 36916371 | 120 | hg77 | GCCCAAGCC TCACCCTCA CACAG (SEQ ID NO: 6) | CGAACCATC CCTCCGCGC CA (SEQ ID NO: 20) | ZNF568 | GCCCAAGCCTCACCCT CACACAGGAAAGCAG ATGTGTTCTGGCCGGA AGTTGAGTGGGGCCGC GGGGCCTGCTGGGAG GTGTTGTCCTCGGAAA CGTCGCTGGCGCGGAG GGATGGTTCG (SEQ ID NO: 118) |
| C9orf50 | 9 | 129620787 | 129620870 | 84 | hg57 | AGAGTAGCC AACTTTGGG GGTTGCT (SEQ ID NO: 7) | GGCACTGTA CCGAGCTTG CTGTTCT (SEQ ID NO: 21) | C9orf50 | AGAGTAGCCAACTTM GGGGTTGCTGTGACGT TTAAATGAGCAAGTAC ATGCCAGTCTTAGAAC AGCAAGCTCGGTACA GTGCC (SEQ ID NO: 119) |

---

What is claimed is:

1. A method of detecting methylation markers in a human subject suspected of having cancer, the method comprising:
   determining a methylation status of each of at least three screening markers identified in a sample obtained from the human subject suspected of having cancer, wherein the sample comprises cell-free DNA that is isolated from blood or plasma of the human subject, wherein a first of the at least three screening markers comprises a methylation locus comprising at least a portion of chr19:12867716-12867820 (SEQ ID NO: 82), a second of the at least three screening markers comprises a methylation locus comprising at least a portion of chr20:48828337-48828448 (SEQ ID NO: 86), and a third of the at least three screening markers comprises a methylation locus comprising at least a portion of chr20:23049354-23049500 (SEQ ID NO: 107).

2. The method of claim 1, wherein the subject is suspected having at least one of the cancers selected from the group consisting of: (i) colorectal cancer, (ii) breast cancer, (iii) lung cancer, and (iv) pancreatic cancer.

3. The method of claim 1, wherein each methylation locus comprises at least one CpG dinucleotide.

4. The method of claim 1, further comprising, determining a methylation status of each of at least three cancer-differentiating markers selected from the DMRs of Table 15, said at least three cancer-differentiating markers identified in a sample obtained from the subject.

5. The method of claim 1, further comprising, determining a methylation status of each of at least three cancer-differentiating markers selected from the DMRs of Table 13, said at least three cancer-differentiating markers identified in a sample obtained from the subject.

6. The method of claim 1, wherein methylation status is determined using quantitative polymerase chain reaction (qPCR).

7. The method of claim 1, wherein methylation status is determined using methylation sensitive restriction enzyme quantitative polymerase chain reaction (MSRE-qPCR).

8. The method of claim 1, wherein methylation status is determined using massively parallel sequencing.

9. The method of claim 1, wherein each methylation locus is equal to or less than 5000 bp in length.

10. The method of claim 1, comprising determining the methylation status of each of the one or more screening markers using next generation sequencing (NGS).

11. The method of claim 10, comprising using one or more oligonucleotide capture baits that enrich for a target region to capture one or more corresponding methylation locus/loci.

* * * * *

UNITED STATES PATENT AND TRADEMARK OFFICE
CERTIFICATE OF CORRECTION

| | |
|---|---|
| PATENT NO. | : 11,530,453 B2 |
| APPLICATION NO. | : 17/027194 |
| DATED | : December 20, 2022 |
| INVENTOR(S) | : Marko Bitenc et al. |

It is certified that error appears in the above-identified patent and that said Letters Patent is hereby corrected as shown below:

In the Claims

Column 143, Claim 1, Line 53, please delete "(SEQ ID NO: 107" and insert --(SEQ ID NO: 107)--.

Signed and Sealed this
Thirty-first Day of January, 2023

*Katherine Kelly Vidal*

Katherine Kelly Vidal
*Director of the United States Patent and Trademark Office*